US008563513B2

(12) United States Patent
Xu et al.

(10) Patent No.: US 8,563,513 B2
(45) Date of Patent: Oct. 22, 2013

(54) PARATHYROID HORMONE PEPTIDES AND PARATHYROID HORMONE-RELATED PROTEIN PEPTIDES AND METHODS OF USE

(75) Inventors: Huaqiang Eric Xu, Grand Rapids, MI (US); Augen A. Pioszak, Edmond, OK (US); Thomas J. Gardella, Needham, MA (US)

(73) Assignees: Van Andel Research Institute, Grand Rapids, MI (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 13/260,699

(22) PCT Filed: Mar. 26, 2010

(86) PCT No.: PCT/US2010/028867
§ 371 (c)(1),
(2), (4) Date: Dec. 7, 2011

(87) PCT Pub. No.: WO2010/111617
PCT Pub. Date: Sep. 30, 2010

(65) Prior Publication Data
US 2012/0083448 A1 Apr. 5, 2012

Related U.S. Application Data

(60) Provisional application No. 61/164,284, filed on Mar. 27, 2009.

(51) Int. Cl.
*A61K 38/00* (2006.01)
*A61K 38/16* (2006.01)
*C07K 1/00* (2006.01)

(52) U.S. Cl.
USPC ....... 514/16.9; 514/16.7; 514/21.2; 514/21.3; 530/324; 530/350; 530/402

(58) Field of Classification Search
None
See application file for complete search history.

(56) References Cited

U.S. PATENT DOCUMENTS

| | | | | |
|---|---|---|---|---|
| 5,460,978 | A * | 10/1995 | Martin et al. | 436/518 |
| 5,717,062 | A * | 2/1998 | Chorev et al. | 530/317 |
| 6,756,480 | B2 * | 6/2004 | Kostenuik et al. | 530/387.1 |
| 7,169,567 | B1 | 1/2007 | Gardella et al. | |
| 2002/0160945 | A1 | 10/2002 | Cantor | |
| 2003/0166836 | A1 | 9/2003 | Dong | |
| 2004/0214996 | A1 | 10/2004 | Kostenuik et al. | |
| 2007/0099831 | A1 | 5/2007 | Morley | |
| 2007/0270341 | A1 | 11/2007 | Morley et al. | |
| 2008/0119401 | A1 | 5/2008 | Dong | |

FOREIGN PATENT DOCUMENTS

| | | |
|---|---|---|
| CN | 101138631 A | 3/2008 |
| EP | 822200 A1 | 2/1998 |
| EP | 1619204 A1 | 1/2006 |
| GB | 2269176 A | 2/1994 |
| JP | 7165790 A | 6/1995 |
| WO | WO9401460 A1 | 1/1994 |
| WO | WO9702834 A1 | 1/1997 |
| WO | WO9804591 A1 | 2/1998 |
| WO | WO9830590 A2 | 7/1998 |
| WO | WO9912561 A2 | 3/1999 |
| WO | WO0002905 A2 | 1/2000 |
| WO | WO0020592 A1 | 4/2000 |
| WO | WO0023594 A1 | 4/2000 |
| WO | WO0031137 A1 | 6/2000 |
| WO | WO0031266 A1 | 6/2000 |
| WO | WO0039278 A2 | 7/2000 |
| WO | WO0121643 A2 | 3/2001 |
| WO | WO0123427 A1 | 4/2001 |
| WO | WO0181415 A2 | 11/2001 |
| WO | WO03009804 A2 | 2/2003 |
| WO | WO03105772 A2 | 12/2003 |
| WO | WO2004067021 A1 | 8/2004 |
| WO | WO2008019062 A2 | 2/2008 |
| WO | WO2008068487 A1 | 6/2008 |
| WO | 2009-017809 | 2/2009 |

OTHER PUBLICATIONS

Dean, T., J.-P. Vilardaga, J. T. Potts, and T. J. Gardella. "Altered Selectivity of Parathyroid Hormone (PTH) and PTH-Related Protein (PTHrP) for Distinct Conformations of the PTH/PTHrP Receptor." Molecular Endocrinology 22(1) 156-166. 2007.

Okazaki, M., S. Ferrandon, J.-P. Vilardaga, M. L. Bouxsein, J. T. Potts, and T. J. Gardella. "Prolonged Signaling at the Parathyroid Hormone Receptor by Peptide Ligands Targeted to a Specific Receptor Conformation." Proceedings of the National Academy of Sciences 105 (43)16525-16530. 2008.

Pioszak, A. A., and H. E. Xu. "Molecular Recognition of Parathyroid Hormone by its G Protein-coupled Receptor." Proceedings of the National Academy of Sciences 105 (13) 5034-5039. 2008.

Dean, T., Linglart, A., Mahon, M.J., Bastepe, M., Juppner, H.,John T. Potts, J.T.Jr., and Gardella, T.J., "Mechanisms of Ligand Binding to the Parathyroid Hormone (PTH)/PTH-Related Protein Receptor: Selectivity of a Modified PTH(1-15) Radioligand for Gas-Coupled Receptor Conformations." Molecular Endocrinology 20 (4) 931-943. 2006.

(Continued)

*Primary Examiner* — Shulamith H Shafer
(74) *Attorney, Agent, or Firm* — Honigman Miller Schwartz and Cohn LLP; Douglas H. Siegel; Jonathan P. O'Brien

(57) ABSTRACT

Provided herein are Parathyroid hormone (PTH) peptides and parathyroid hormone-related protein (PTHrP) peptides (e.g., PTH analogs, PTHrP analogs), and related variants, chemical derivatives, fusion polypeptides, multimeric polypeptides, and peptidomimetics, peptoids, the like. Also provided are their use in methods for activating the PTH receptor in a cell (e.g., an osteoblast), methods of treating a subject with bone loss (e.g., by administration of a PTH peptide or PTHrP peptide (e.g., a PTH analog or PTHrP analog)), methods of ameliorating a symptom associated with osteoporosis in a subject, methods of retarding the progression of osteoporosis in a subject, and methods of regenerating bone in a subject.

31 Claims, 10 Drawing Sheets

(56) References Cited

OTHER PUBLICATIONS

Hoare, S. R.J.,Gardella T.J., and Usdin, T.B. "Evaluating the Signal Transduction Mechanism of the Parathyroid Hormone 1 Receptor." The Journal of Biological Chemistry 276 (11) 7741-7753. 2001.
(1994) The CCP4 suite: programs for protein crystallography. Acta crystallographica 50, 760-763.
Bergwitz, C, Gardella, T. J., Flannery, M. R., Potts. J. T., Jr., Kronenberg, H. M., Goldring, S. R., & Juppner, H. (1996) Full activation of chimeric receptors by hybrids between parathyroid hormone and calcitonin. Evidence for a common pattern of ligand-receptor interaction. The Journal of biological chemistry 271, 26469-26472.
Bradford, M. M. (1976) Analytical biochemistry 72, 248-254.
Burtis, W. J., Wu, T., Bunch, C, Wysolmerski, J. J., Insogna, K. L., Weir, E. C, Broadus, A. E., & Stewart, A. F. (1987) Identification of a novel 17,000-dalton parathyroid hormone-like adenylate cyclase-stimulating protein from a tumor associated with humoral hypercalcemia of malignancy. The Journal of biological chemistry 262, 7151-7156.
Dean, T., Linglart, A., Mahon, M. J., Bastepe, M., Juppner, H., Potts, J. T., Jr., & Gardella, T. J. (2006) Mechanisms of ligand binding to the parathyroid hormone (PTH)/PTH-related protein receptor: selectivity of a modified PTH(I-15) radioligand for GalphaS-coupled receptor conformations. Molecular endocrinology (Baltimore, Md 20, 931-943.
Dean, T., Vilardaga, J. P., Potts, J. T., Jr., & Gardella, T. J. (2008) Altered selectivity of parathyroid hormone (PTH) and PTH-related protein (PTHrP) for distinct conformations of the PTH/PTHrP receptor. Molecular endocrinology (Baltimore, Md 22, 156-166.
Gardella, T. J. & Juppner, H. (2000) Interaction of PTH and PTHrP with their receptors. Reviews in endocrine & metabolic disorders 1, 317-329.
Gensure, R. C, Gardella, T. J., & Juppner, H. (2005) Parathyroid hormone and parathyroid hormone-related peptide, and their receptors. Biochemical and biophysical research communications 328, 666-678.
Gensure, R. C, Shimizu, N., Tsang, J., & Gardella, T. J. (2003) Identification of a contact site for residue 19 of parathyroid hormone (PTH) and PTH-related protein analogs in transmembrane domain two of the type 1 PTH receptor. Molecular endocrinology (Baltimore, Md 17, 2647-2658.
Grauschopf, U., Lille, H., Honold, K., Wozny, M., Reusch, D., Esswein, A., Schafer, W., Rucknagel, K. P., & Rudolph, R. (2000) The N-terminal fragment of human parathyroid hormone receptor 1 constitutes a hormone binding domain and reveals a distinct disulfide pattern. Biochemistry 39, 8878-8887.
Hoare, S. R., Clark, J. A., & Usdin, T. B. (2000) Molecular determinants of tuberoinfundibular peptide of 39 residues (TIP39) selectivity for the parathyroid hormone-2 (PTH2) receptor. N-terminal truncation of TIP39 reverses PTH2 receptor/PTHI receptor binding selectivity. The Journal of biological chemistry 275, 27274-27283.
Hoare, S. R., Gardella, T. J., & Usdin, T. B. (2001) Evaluating the signal transduction mechanism of the parathyroid hormone 1 receptor. Effect of receptor-G-protein interaction on the ligand binding mechanism and receptor conformation. The Journal of biological chemistry 276, 7741-7753.
Horwitz, M. J., Tedesco, M. B., Gundberg, C, Garcia-Ocana, A., & Stewart, A. F. (2003) Short-term, high-dose parathyroid hormone-related protein as a skeletal anabolic agent for the treatment of postmenopausal osteoporosis. The Journal of clinical endocrinology and metabolism 88, 569-575.
Jilka, R. L. (2007) Molecular and cellular mechanisms of the anabolic effect of intermittent PTH. Bone 40, 1434-1446.
Juppner, H., Abou-Samra, A. B., Freeman, M., Kong, X. F., Schipani, E., Richards, J., Kolakowski, L. F., Jr., Hock, J., Potts, J. T., Jr., Kronenberg, H. Mv et al. (1991) A G protein-linked receptor for parathyroid hormone and parathyroid hormone-related peptide. Science (New York, N.Y25A, 1024-1026.
Karaplis, A. C, Luz, A., Glowacki, J., Bronson, R. T., Tybulewicz, V. L., Rronenberg, H. M., & Mulligan, R. C. (1994) Lethal skeletal dysplasia from targeted disruption of the parathyroid hormone-related peptide gene. Genes & development 8, 277-289.
Klein, R. F., Strewler, G. J., Leung, S. C, & Nissenson, R. A. (1987) Parathyroid hormone-like adenylate cyclase-stimulating activity from a human carcinoma is associated with bone-resorbing activity. Endocrinology 120, 504-511.
Kleywegt, G. J. & Jones, T. A. (1997) Model building and refinement practice. Methods in enzymology 277, 208-230.
Lanske, B., Karaplis, A. C, Lee, K., Luz, A., Vortkamp, A., Pirro, A., Karperien, M., Defize, L. H., Ho, C, Mulligan, R. C, et al. (1996) PTH/PTHrP receptor in early development and Indian hedgehog-regulated bone growth. Science (New York, N.Y 273, 663-666.
Laskowski, R. A., MacArthur, M. W., Moss, D. S., & Thornton, J. M. (1993) Procheck: a program to check the stereochemical quality of protein structures. Journal of Applied Crystallography 26, 283-291.
Lawrence, M. C. & Colman, P. M. (1993) Shape complementarity at protein/protein interfaces. Journal of molecular biology 234, 946-950.
Luck, M. D., Carter, P. H., & Gardella, T. J. (1999) The (1-14) fragment of parathyroid hormone (PTH) activates intact and amino-terminally truncated PTH-I receptors. Molecular endocrinology (Baltimore, Md 13, 670-680.
Mann, R., Wigglesworth, M. J., & Donnelly, D. (2008) Ligand-receptor interactions at the parathyroid hormone receptors: subtype binding selectivity is mediated via an interaction between residue 23 on the ligand and residue 41 on the receptor. Molecular pharmacology 74, 605-613.
Marx, U. C, Adermann, K., Bayer, P., Forssmann, W. G., & Rosch, P. (2000) Solution structures of human parathyroid hormone fragments hPTH(I-34) and hPTH(I-39) and bovine parathyroid hormone fragment bPTH(I-37). Biochemical and biophysical research communications 267, 213-220.
McCoy, A. J., Grosse-Kunstleve, R. W., Adams, P. D., Winn, M. D., Storoni, L. C, & Read, R. J. (2007) Phaser Crystallographic Software. Journal of Applied Crystallography 40, 658-674.
Moseley, J. M., Kubota, M., Diefenbach-Jagger, H., Wettenhall, R. E., Kemp. B. E., Suva, L. J., Rodda, C. P., Ebeling, P. R., Hudson, P. J., Zajac, J. D., et al. (1987) Parathyroid hormone-related protein purified from a human lung cancer cell line. Proceedings of the National Academy of Sciences of the United States of America 84, 5048-5052.
Murray, T. M., Rao, L. G., Divieti, P., & Bringhurst, F. R. (2005) Parathyroid hormone secretion and action: evidence for discrete receptors for the carboxyl-terminal region and related biological actions of carboxyl-terminal ligands. Endocrine reviews 26, 78-113.
Murshudov, G. N., Vagin, A. A., & Dodson, E. J. (1997) Refinement of macromolecular structures by the maximum-likelihood method. Acta crystallographica 53, 240-255.
Neer, R. M., Arnaud, C. D., Zanchetta, J. R., Prince, R., Gaich, G. A., Reginster, J. Y., Hodsman, A. B., Eriksen, E. F., Ish-Shalom, S., Genant, H. K., et al. (2001) Effect of parathyroid hormone (1-34) on fractures and bone mineral density in postmenopausal women with osteoporosis. The New England journal of medicine 344, 1434-1441.
Okazaki, M., Ferrandon, S., Vilardaga, J. P.. Bouxsein, M. L., Potts, J. T., Jr., & Gardella, T. J. (2008) Prolonged signaling at the parathyroid hormone receptor by peptide ligands targeted to a specific receptor conformation. Proceedings of the National Academy of Sciences of the United States of America 105, 16525-16530.
Otwinowski, Z. & Minor, W. (1997) Processing of X-ray diffraction data collected in oscillation mode. Methods in enzymology 276 (Pt A), 307-326.
Parthier, C, Kleinschmidt, M., Neumann, P., Rudolph, R., Manhart, S., Schlenzig, D., Fanghanel, J., Rahfeld, J. U., Demuth, H. U., & Stubbs, M. T. (2007) Crystal structure of the incretin-bound extracellular domain of a G protein-coupled receptor. Proceedings of the National Academy of Sciences of the United States of America 104, 13942-13947.
Penel, S. & Doig, A. J. (2001) Rotamer strain energy in protein helices-quantification of a major force opposing protein folding. Journal of molecular biology 305, 961-968.

(56) References Cited

OTHER PUBLICATIONS

Pioszak, A. A., Parker, N. R., Suino-Powell, K., & Xu, H. E. (2008) Molecular recognition of corticotropin-releasing factor by its G-protein-coupled receptor CRFRI. The Journal of biological chemistry 283, 32900-32912.

Pioszak, A. A. & Xu, H. E. (2008) Molecular recognition of parathyroid hormone by its G protein-coupled receptor. Proceedings of the National Academy of Sciences of the United States of America 105, 5034-5039.

Pioszak, A. A. & Xu, H. E. (2008) Proceedings of the National Academy of Sciences of the United States of America 105, 5034-5039.

Plotkin, H., Gundberg, C, Mitnick, M., & Stewart, A. F. (1998) Dissociation of bone formation from resorption during 2-week treatment with human parathyroid hormone-related peptide-(I-36) in humans: potential as an anabolic therapy for osteoporosis. The Journal of clinical endocrinology and metabolism 83, 2786-2791.

Potts, J. T. (2005) Parathyroid hormone: past and present. The Journal of endocrinology 187, 311-325.

Potts, J. T. & Gardella, T. J. (2007) Progress, paradox, and potential: parathyroid hormone research over five decades. Annals of the New York Academy of Sciences 1117, 196-208.

Rkronenberg, H. M. (2006) PTHrP and skeletal development. Annals of the New York Academy of Sciences 1068, 1-13.

Runge, S., Thogersen, H., Madsen, K., Lau, J., & Rudolph, R. (2008) Crystal structure of the ligand-bound glucagon-like peptide-1 receptor extracellular domain. The Journal of biological chemistry 283, 11340-11347.

Suva, L. J., Winslow, G. A., Wettenhall, R. E., Hammonds, R. G., Moseley, J. M., Diefenbach-Jagger, H., Rodda, C. P., Kemp, B. E., Rodriguez, H., Chen, E. Y., et al. (1987) A parathyroid hormone-related protein implicated in malignant hypercalcemia: cloning and expression. Science (New York, N.Y 237, 893-896.

Weidler, M., Marx, U. C, Seidel, G., Schafer, W., Hoffmann, E., Esswein, A., & Rosch, P. ( 1999) The structure of human parathyroid hormone -related protein(I-34) in near-physiological solution. FEBS letters 444, 239-244.

Winn, M. D., Isupov, M. N., & Murshudov, G. N. (2001) Use of TLS parameters to model anisotropic displacements in macromolecular refinement. Acta crystallographica 57, 122-133.

Yang, D., Singh, R., Divieti, P., Guo, J., Bouxsein, M. L., & Bringhurst, F. R. (2007) Contributions of parathyroid hormone (PTH)/PTH-related peptide receptor signaling pathways to the anabolic effect of PTH on bone. Bone 40, 1453-1461.

Gensure: "Multiple Sites of Contact between the Carboxyl-terminal Binding Domain of PTHrP-(1-36) Analogs and the Amino-terminal Extracellular Domain of the Photoaffinity Cross-linking"; Journal of Biological Chemistry; May 21, 2001; pp. 28650-28658, vol. 276, No. 31.

Schievano et al: "Conformational studies of parathyroid hormone (PTH)/PTH-related protein (PTHrP) chimeric peptides"; Biopolymers; Jan. 11, 2000; pp. 429-447; vol. 54, No. 6.

\* cited by examiner

US 8,563,513 B2

PARATHYROID HORMONE PEPTIDES AND PARATHYROID HORMONE-RELATED PROTEIN PEPTIDES AND METHODS OF USE

CROSS REFERENCE TO RELATED APPLICATIONS

This application is the U.S. National phase of PCT Application Serial No. PCT/US2010/028867, filed Mar. 26, 2010, which claims the priority of U.S. Provisional Patent Application Ser. No. 61/164,284 filed Mar. 27, 2009, both of which documents are incorporated herein by reference in their entirety.

INCORPORATION BY REFERENCE OF MATERIAL SUBMITTED ELECTRONICALLY

Incorporated by reference in its entirety is a computer-readable sequence listing submitted concurrently herewith and identified as follows: One 44.9 KB ASCII (Text) file named "VAN067FP409WOSequenceListing.txt," created on Mar. 26, 2010.

FIELD OF THE INVENTION

The invention is in the field of biochemistry and medicine and relates to peptides or polypeptides that activate the parathyroid hormone receptor and methods of using these peptides or polypeptides to enhance bone growth (e.g., treat osteoporosis) or treat cancer.

BACKGROUND OF THE INVENTION

The parathyroid hormone receptor (PTH1R) is a class B G protein-coupled receptor (GPCR) that transduces signals from two related signaling molecules that have distinct functions in bone biology: parathyroid hormone (PTH) and parathyroid hormone-related protein (PTHrP) [(1); reviewed in (2, 3)]. PTH is an 84-amino acid polypeptide endocrine hormone that is produced by the parathyroid glands and secreted into the circulation in response to low calcium levels [reviewed in (4-6)]. The classical actions of PTH are mediated by PTH1R expressed in bone and kidney tissues and include stimulation of osteoclastic bone resorption to maintain calcium homeostasis, and stimulation of calcium reabsorption, synthesis of 1,25-dihydroxyvitamin D3, and phosphate excretion in kidney. Paradoxically, PTH also has stimulatory effects on osteoblastic cells resulting in bone formation [reviewed in (7)], providing the molecular basis for the clinical use of PTH as an anabolic therapy for osteoporosis (8). Anabolic PTH therapy requires intermittent administration to avoid the bone resorptive effects that predominate with sustained elevation of PTH in the circulation.

PTHrP is a 141-amino acid polypeptide that was originally isolated as the factor responsible for humoral hypercalcemia of malignancy (9-12) and was subsequently shown to be a critical developmental factor that regulates endochondral bone formation [(13, 14); reviewed in (15)]. PTHrP is produced locally and functions in a paracrine/autocrine fashion to activate PTH1R expressed on chondrocytes to regulate their proliferation and differentiation. PTHrP also has anabolic effects when administered to osteoporosis patients (16), but appears to be more purely anabolic than PTH by uncoupling bone formation from bone resorption (17).

PTH and PTHrP can activate several downstream signaling pathways through PTH1R to mediate their effects, but activation of the cAMP/PKA pathway via $G\alpha_s$-coupling predominates and is responsible for the bone anabolic effect (18). The N-terminal 34-residue peptide fragments of PTH and PTHrP are sufficient to bind and activate PTH1R to the same extent as the native molecules, and PTH- and PTHrP-(1-34) are equally potent for activating cAMP signaling (1). Their interaction with the receptor follows a "two-domain" model. Residues 1-14 interact with the 7-transmembrane (7-TM) helical domain embedded in the membrane and residues 15-34 interact with the N-terminal extracellular domain (ECD) of the receptor (19, 20). The 1-14 fragments of PTH and PTHrP have eight amino acid sequence identities reflecting the critical role this fragment plays in activating the receptor (20). The 15-34 fragments impart high affinity binding to the receptor, but this portion of PTH and PTHrP is less conserved with only three amino acid identities. PTH and PTHrP form similar α-helical structures in solution (21, 22).

Despite their shared two-domain receptor binding mechanism, common secondary structure, and equipotent activation of signaling, PTH and PTHrP differ in their abilities to bind to two pharmacologically distinct PTH1R conformations that are distinguished by the presence or absence of G protein-coupling. The peptides bind with similar high affinity to the G protein-coupled receptor (RG conformational state), but in the absence of G protein coupling (R0 conformational state) PTHrP binding is significantly diminished whereas PTH binding is only slightly decreased (23-25). Thus, PTHrP is more RG-selective than PTH. The different R0/RG selectivity profiles of PTH and PTHrP correlate with distinct temporal effects on cAMP signaling. PTH elicits a longer lasting cAMP signal after ligand wash-out than PTHrP (23). Divergent residue 5 (Ile in PTH, His in PTHrP) is a key determinant of the R0/RG selectivity differences of the peptides (23, 25), but the 15-34 fragment of PTH contributes to its strong R0 binding (23, 26) suggesting that interactions with the ECD contribute to the duration of cAMP signaling. Importantly, temporal differences in cAMP signaling can have dramatic effects in vivo. Compared to wild type PTH, PTH analogs that exhibit increased R0 binding induce sustained cAMP responses in cells and result in increased trabecular bone volume and increased cortical bone resorption in mice receiving daily injections (26). These studies indicate that the R0/RG selectivity profiles of PTH and PTHrP contribute to the different physiological and therapeutic actions of the peptides, and highlight the importance of a detailed understanding of the structural basis of how the binding of PTH and PTHrP to the receptor differs.

The inventors previously developed methodology that allowed them to determine the high resolution crystal structure of the PTH1R ECD in complex with the C-terminally amidated 15-34 fragment of PTH [PTH(15-34)NH2] (27). The ECD was expressed in E. coli as a fusion protein linked to the C-terminus of bacterial maltose binding protein (MBP). MBP solubilizes the ECD during an in vitro disulfide shuffling reaction required to properly form three disulfide bonds and facilitates crystallization of the fusion protein. The PTH1R ECD forms a fold that is conserved among class B GPCR ECDs (28-30) and consists of an N-terminal α-helix followed by two anti-parallel β-sheets and a short C-terminal α-helix, all held together by the three disulfide bonds. PTH (15-34)NH2 forms an amphipathic α-helix that binds to a hydrophobic groove at the interface of the secondary structure elements.

BRIEF SUMMARY OF THE INVENTION

The inventors have developed a high resolution crystal structure of PTHrP bound to the extracellular domain (ECD)

of PTH1R and compared it to the PTH-PTH1R ECD complex. PTHrP forms an amphipathic α-helix that binds to a hydrophobic groove in the ECD similar to PTH, but whereas PTH forms a continuous, straight helix, the PTHrP helix curves gently and "unwinds" at the C-terminus, causing significantly different contacts between the C-termini of the peptides and the ECD. The receptor accommodates the different binding modes by changing the conformation of two residues at the peptide binding site. Guided by the structures, the inventors designed hybrid peptides containing swaps of the PTH and PTHrP residues at positions that determine the different binding modes; those that exhibited diminished ECD-binding also had decreased affinity for the G protein-uncoupled conformation (R0) of PTH1R in cell membranes, but retained normal binding to the G protein-coupled conformation (RG). The RG-selective peptides potently stimulated cAMP accumulation in cells, but generated shorter-lived responses after ligand wash-out, suggesting that they may have therapeutic value by providing a potent, but pulsatile action at the receptor.

The inventors have demonstrated that PTH and PTHrP bind to the ECD with similar affinities and they present the high resolution crystal structure of the C-terminally amidated 12-34 fragment of PTHrP [PTHrP(12-34)NH2] in complex with the MBP-PTH1R ECD fusion protein. Comparison of the PTH- and PTHrP-bound structures reveals significant differences in the ECD-binding modes of the peptides, primarily at the C-termini of the peptides.

The inventors used the PTH- and PTHrP-bound structures as a guide to design PTH and PTHrP peptide analogs, some of which are hybrid PTH/PTHrP peptides containing swaps of the residues at positions that determine the different ECD-binding modes, allowing them to obtain RG-selective peptides that potently stimulate cAMP signaling with temporally shorter responses. These analogs may have therapeutic potential as more purely anabolic PTH analogs lacking hypercalcemic side effects by providing a potent, but pulsatile action at the receptor.

In accordance with the foregoing, the present invention provides PTH peptides comprising the amino acid sequence of wild-type PTH (SEQ ID NO: 9) with amino acid substitutions at positions within the C-terminal half of the peptide (e.g., amino acids 15-34 of SEQ ID NO: 9). As shown herein for the first time, the PTH peptides of the present disclosures exhibit altered biological properties (e.g., decreased affinity for the G protein-uncoupled conformation (R0) of PTH1R, as compared to the affinity of wild-type PTH to the R0 conformation of PTH1R, while the PTH peptide retains binding to the G protein-coupled conformation (RG) of PTH1R, and is able to stimulates cAMP accumulation in cells; diminished binding to the ECD of the PTH1R), as compared to wild-type PTH. Such altered biological properties are believed to increase the therapeutic potential of these PTH peptides.

In some aspects, the PTH peptide comprises the amino acid sequence of wild-type PTH (SEQ ID NO: 9) with an amino acid substitution at one or more of the amino acids positions 12, 14, 16, 17, and 27, or an analog thereof comprising a disulfide bond.

In some aspects, the PTH peptide comprises the C-terminal half of wild-type PTH (amino acids 15-34 of SEQ ID NO: 9) with an amino acid substitution at one or more of positions 23, 27, 28, and 31 of SEQ ID NO: 9. In some embodiments, the PTH peptide exhibits decreased affinity for the G protein-uncoupled conformation (R0) of Parathyroid Hormone Receptor (PTH1R), as compared to the affinity of wild-type PTH (SEQ ID NO: 9) for the R0 conformation of PTH1R, yet retains binding to the G protein-coupled conformation (RG) of PTH1R, and stimulates cAMP accumulation in cells.

In yet other aspects, the PTH peptide comprises amino acids 15-34 of SEQ ID NO: 9, with an amino acid substitution at one or more of positions 20, 21, 23, 24, 27, 28, and 34. In specific embodiments, the PTH peptide exhibits diminished binding to the extracellular domain (ECD) of PTH1R, as compared to the binding of wild-type PTH to the ECD of PTH1R.

Further provided herein are PTHrP peptides comprising the amino acid sequence of wild-type PTHrP (SEQ ID NO: 79) with amino acid substitutions at positions within the C-terminal half of the peptide (e.g., amino acids 12-34 of SEQ ID NO: 79). As shown herein for the first time, the PTHrP peptides of the present disclosures exhibit altered biological properties (e.g., decreased affinity for the G protein-uncoupled conformation (R0) of PTH1R, as compared to the affinity of wild-type PTHrP to the R0 conformation of PTH1R, while the PTHrP peptide retains binding to the G protein-coupled conformation (RG) of PTH1R, and is able to stimulate cAMP accumulation in cells; diminished binding to the ECD of the PTH1R), as compared to wild-type PTHrP. Such altered biological properties are believed to increase the therapeutic potential of these PTHrP peptides.

In some aspects, the PTHrP peptide comprises the C-terminal half of wild-type PTHrP (amino acids 12-34 of SEQ ID NO: 79) with an amino acid substitution at one or more of positions 23, 27, 28, and 31 or SEQ ID NO: 79. In specific aspects, the PTHrP peptide exhibits decreased affinity for the G protein-uncoupled conformation (R0) of PTH1R, as compared to the affinity of wild-type PTHrP (SEQ ID NO: 79) for the R0 conformation of PTH1R, yet retains binding to the G protein-coupled conformation (RG) of PTH1R, and stimulates cAMP accumulation in cells.

In certain aspects, the PTHrP peptide comprises amino acids 12-34 of SEQ ID NO: 79, with an amino acid substitution at one or more of positions 20, 21, 23, 24, 27, 28, 32, and 33. In specific aspects, the PTHrP peptide exhibits diminished binding to the ECD of PTH1R, as compared to the binding of wild-type PTHrP to the ECD or PTH1R.

In specific embodiments, the PTH peptides and PTHrP peptides (or polypeptide analogs) described herein comprise the amino acid sequence of any of SEQ ID NOs: 1-101. Further provided herein are variants, fusion proteins, multimeric peptides, peptidomimetics, peptoids, and chemical derivatives thereof. Such a PTH or PTHrP peptide or polypeptide fusion protein may include one of the PTH or PTHrP peptide or polypeptide analogs, optionally, a linker region; and a second polypeptide that is linked to the PTH or PTHrP peptide or polypeptide analog, or to the linker region, which second polypeptide is not natively linked to the PTH or PTHrP peptide or polypeptide analog. Also, the PTH or PTHrP peptide or polypeptide analog may be linked an additional peptide that promotes entry into cells.

In exemplary embodiments, the PTH peptide (or polypeptide analog) comprises an amino acid sequence of any of SEQ ID NOs: 1-78, and variants, fusion proteins, multimeric peptides, peptidomimetics, peptoids, and chemical derivatives thereof. In specific embodiments, the PTH peptide comprises the amino acid sequence of SEQ ID NO: 55.

In other exemplary embodiments, the PTHrP peptide (or polypeptide analog) comprises an amino acid sequence of any of SEQ ID NOs: 79-101, and variants, fusion proteins, multimeric peptides, peptidomimetics, peptoids, and chemical derivatives thereof. In specific embodiments, the PTH peptide comprises the amino acid sequence of SEQ ID NO: 81.

The invention furthermore provides a kit for treating osteoporosis. In some aspects, the kit comprises a peptide selected from the group consisting of a PTH peptide or analog as described herein and a PTHrP peptide described herein, and instructions for administration thereof to a subject having osteoporosis.

The PTH peptides, PTHrP peptides, and analogs, chemical derivatives, fusion polypeptides, multimeric peptides described herein can be used in the preparation of a medicament for the treatment of osteoporosis. Accordingly, the present invention additionally provides compositions, e.g., pharmaceutical compositions, comprising a PTH or PTHrP peptide as described herein (or polypeptide analog, analog, chemical derivative, fusion polypeptide, multimeric peptide, and the like) and a pharmaceutically acceptable carrier or excipient.

Also included is an inventive method for activating a PTH receptor in a cell, comprising introducing into a cell the above-mentioned PTH or PTHrP peptide or polypeptide analog, such that the peptide or polypeptide causes said PTH receptor to be activated. This method may be carried out in a live animal, the cell may be an osteoblast, and the introducing may be by oral delivery or injection.

Further, the present invention includes a method for treating a mammalian subject having a disease or condition associated with undesired bone loss, comprising administering to a subject having undesired bone loss an effective amount of the above-mentioned pharmaceutical composition, thereby treating said subject. With this method, the subject may be a human, and the disease may be osteoporosis.

The invention moreover provides a method of ameliorating a symptom associated with osteoporosis in a subject, a method of retarding the progression of osteoporosis in a subject, and a method of regenerating bone in a subject, each of which, comprise administering to the subject a pharmaceutical composition as described herein in an amount effective to ameliorate a symptom associated with osteoporosis in the subject, retard the progression of osteoporosis in the subject, or regenerate bone in the subject.

Further aspects and embodiments of the invention are described in more detail herein.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings and tables, certain embodiment(s) which are presently preferred. It should be understood, however, that the invention is not limited to the precise arrangements and instrumentalities shown.

FIGS. 1A and 1B show the ability of the indicated PTH (FIG. 1A) or PTHrP (FIG. 1B) peptides to compete with the association of N-terminally biotinylated PTH (7-34)NH2 (23 nM) and the MBP-PTH1R ECD fusion protein (23 nM) was assessed with an AlphaScreen luminescent proximity assay. The data represent the average of duplicate samples. FIGS. 1C and 1D show steady-state analysis of real-time binding data obtained with the Octet Red system. Biotinylated PTH1R ECD was immobilized on streptavidin sensor tips and PTH(1-34)NH2 (FIG. 1C) and PTHrP(1-34)NH2 (FIG. 1D) binding was assessed. The plots in the panels FIGS. 1C and 1D show the response vs. peptide concentration curves derived from the raw binding data (FIG. 6). The Kd values for PTH and PTHrP are 2.8 µM and 0.99 µM, respectively.

FIG. 2A shows an overall view of the PTHrP-ECD complex with the ECD in slate-blue and PTHrP in magenta. Residues 57-101 were not observed in the electron density maps. MBP is not shown for clarity. FIG. 2B reveals the molecular surface of the ECD showing the hydrophobic groove contacted by F23', L24', L27', and I28' of PTHrP. The surface is colored according to atom type: grey for carbon, blue for nitrogen, and red for oxygen. FIG. 2C are omit electron density maps for PTHrP. The $F_o$-$F_c$ omit map is shown as a green mesh contoured at 3σ and the $2F_o$-$F_c$ omit map is shown as a blue mesh contoured at 1σ. FIG. 2D shows a detailed view of the PTHrP-ECD interface. PTHrP is shown as a magenta coil and selected side chains are shown as sticks. The dashed red lines indicate hydrogen bonds and the red sphere is a water molecule. FIG. 2E is a close-up view of the hydrogen bond network involving residues 32-34 of PTHrP. FIG. 2F shows a structural alignment of the PTHrP-ECD complex and the PTH-ECD complex (PDB code 3C4M). The PTHrP-ECD complex is colored as above, PTH is yellow, and the PTH-bound ECD is green. Selected side chains are shown as sticks. Hydrogen bonds are depicted as red dashes for the PTHrP-ECD complex and green dashes for the PTH-ECD complex. FIG. 2G is an amino acid sequence alignment of human PTH and PTHrP residues 1-34 with the length of the α-helices designated above and below the sequence. FIG. 2H shows the results of an AlphaScreen single point competition assay assessing the ability of PTH(15-34)NH2 alanine-scan peptides (20 µM) to compete with the interaction of biotin-PTH (23 nM) and MBP-PTH1R-ECD (23 nM). The results are the average of duplicate samples. FIG. 2I shows the results of an AlphaScreen assay as in panel FIG. 2H except with PTHrP(12-34)NH2 alanine-scan peptides.

FIG. 3A shows the results of an AlphaScreen single point competition assay assessing the ability of hybrid peptides in the PTH(15-34)NH2 scaffold (20 µM) to compete with the interaction of biotin-PTH (23 nM) and MBP-PTH1R-ECD (23 nM). The results are the average of duplicate samples. FIG. 3B shows the results of an AlphaScreen assay as in panel FIG. 3A except with hybrid peptides in the PTHrP(12-34)NH2 scaffold. FIG. 3C is a close-up view of the van der Waals contacts formed by W23' and K27' in the PTH-ECD structure. FIG. 3D is a close-up view of the van der Waals contacts formed by F23' and L27' in the PTHrP-ECD structure.

FIG. 4A shows the binding of the indicated hybrid peptides in the PTH(1-34)NH2 scaffold to the R0 and RG receptor states. FIG. 4B shows the binding of the indicated hybrid peptides in the PTHrP(1-34)NH2 scaffold to the R0 and RG receptor states.

FIG. 5A shows the results of a dose-response assay for cAMP accumulation. COS cells transiently expressing PTH1R were stimulated with the indicated peptides for 30 min at 37° C. after which the cells were lysed and cAMP content was assessed. The data are the average of duplicate samples and are normalized to the maximal cAMP level observed in the presence of wt PTH(1-34)NH2. Basal cAMP was 0.24 pmol per well and maximal cAMP induced by PTH was 6.1 pmol per well. The EC50 values for PTH, PTH(W23'F/V31'I), PTHrP, and PTHrP (L27K) were 71.6 pM, 41.5 pM, 67.7 pM, and 44.4 pM, respectively. FIG. 5B shows the results of a ligand wash-out assay. The cells were stimulated with the indicated peptide for 10 min at room temperature, the ligand was washed out, and cAMP accumulation was assessed at the indicated times after wash out. The results are the average of duplicate samples and are normalized to the level of cAMP induced during the initial stimulation. Basal cAMP was ~0.24 pmol per well and maximal cAMP induced by the initial stimulation was ~2.9 pmol per well.

FIG. 6A shows biotinylated PTH1R ECD was immobilized on streptavidin sensor tips and the binding of PTH(1-34)NH$_2$ was assessed at the following concentrations: 156.25 nM, 312.5 nM, 625 nM, 1.25 µM, 2.5 µM, 5 µM, 10 µM. FIG. 6B shows the same panel as FIG. 6A, except the binding of PTHrP(1-34)NH$_2$ was assessed.

In FIGS. 7A and 7B (0.1 nM and 0.03 nM) each PTH analog is identified by ##-##-SBSL (e.g. "07-12-18-40-SBSL" is represented as "18-40").

DETAILED DESCRIPTION OF THE INVENTION

General Considerations

Figures 1A, 1B, 1C, 1D:
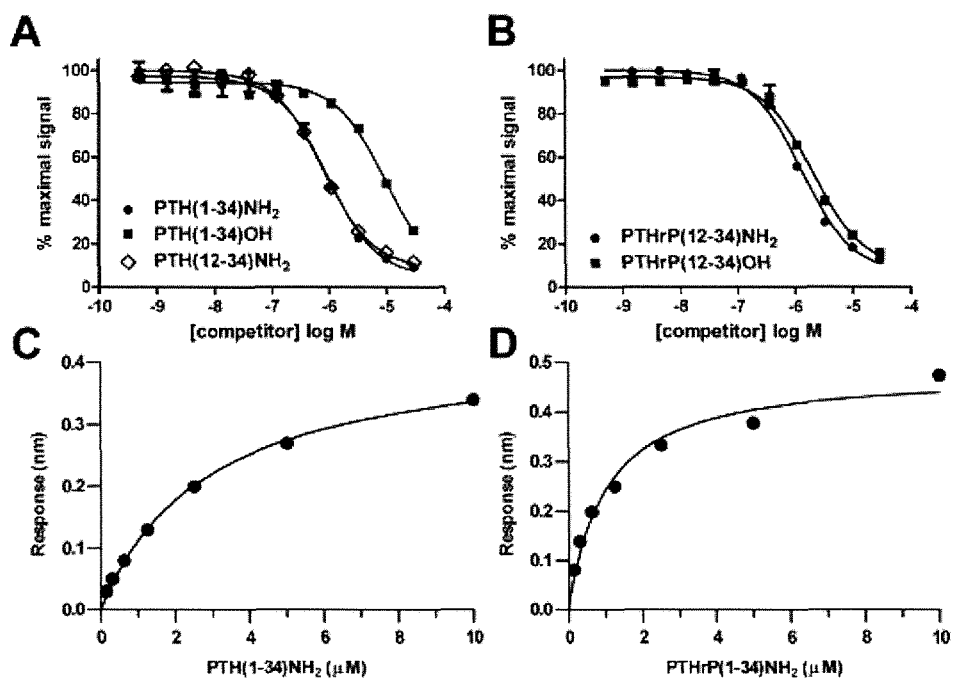
FIGS. 1A-1D demonstrate PTH and PTHrP binding to the PTH1R ECD.

It is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Unless defined otherwise, all technical and scientific terms used herein have the meaning commonly understood by one of ordinary skill in the art to which this invention belongs. Generally, the nomenclature used herein and the laboratory procedures in cell culture, molecular genetics, organic chemistry and nucleic acid chemistry described below are those well known and commonly employed in the art. Although any methods, devices and materials similar or equivalent to those described herein can be used in the practice or testing of the invention, the preferred methods, devices and materials are now described.

In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All references, patents, patent publications, articles, and databases, referred to in this application are incorporated herein by reference in their entirety, as if each were specifically and individually incorporated herein by reference. Such patents, patent publications, articles, and databases are incorporated for the purpose of describing and disclosing the subject components of the invention that are described in those patents, patent publications, articles, and databases, which components might be used in connection with the presently described invention. The information provided herein is not admitted to be prior art to the present invention, but is provided solely to assist the understanding of the reader.

The details of one or more embodiments of the invention are set forth in the accompanying drawings and the description below. Other features, embodiments, and advantages of the invention will be apparent from the description and drawings, Examples, Sequence Listing, and from the claims. The preferred embodiments of the present invention may be understood more readily by reference to the following detailed description of the specific embodiments, the Examples, and the Sequence Listing included hereafter.

For clarity of disclosure, and not by way of limitation, the detailed description of the invention is divided into the subsections that follow.

PTH Peptides and PTHrP Peptides

PTH and PTHrP elicit distinct biological actions by activating their common receptor, PTH1R. A high resolution structural understanding of how the peptides bind the receptor is important to elucidate the biochemical mechanisms responsible for the regulation of mineral ion homeostasis and bone remodeling by PTH and bone development by PTHrP, and also has practical application for aiding the rational design of peptide analogs for therapeutic purposes. The inventors have resolved a structure of PTHrP in complex with the PTH1R ECD. Combined with their previous structure of the PTH-PTH1R ECD complex (27), the inventors have a complete picture of the structural mechanisms used by the PTH1R ECD to recognize PTH and PTHrP. The peptides bind to the ECD as amphipathic α-helices that contact the hydrophobic groove in the ECD. Two of the three invariant residues in the 15-34 fragments, R20' and L24', anchor the interactions. After residue L24' the peptides diverge such that their C-termini make significantly different contacts to the ECD (FIG. 2F), a result foreshadowed by our ECD-binding data showing that the C-terminal amide group of PTH, but not PTHrP, is important for ECD-binding (FIG. 1). The third invariant residue in the 15-34 fragments, H32', provides a critical hydrogen bond to the receptor in the PTHrP-bound structure, but is solvent exposed in the PTH-bound structure. Interestingly, R20' and L24' are conserved in TIP39, a peptide that activates the PTH type 2 receptor (36), but H32' is not, consistent with the inventors observations that the N-terminal portion of the 15-34 fragments provides the anchor point of the peptide-ECD interactions and the C-terminal portions vary in their interaction with the receptor.

Figures 3A, 3B, 3C, 3D:
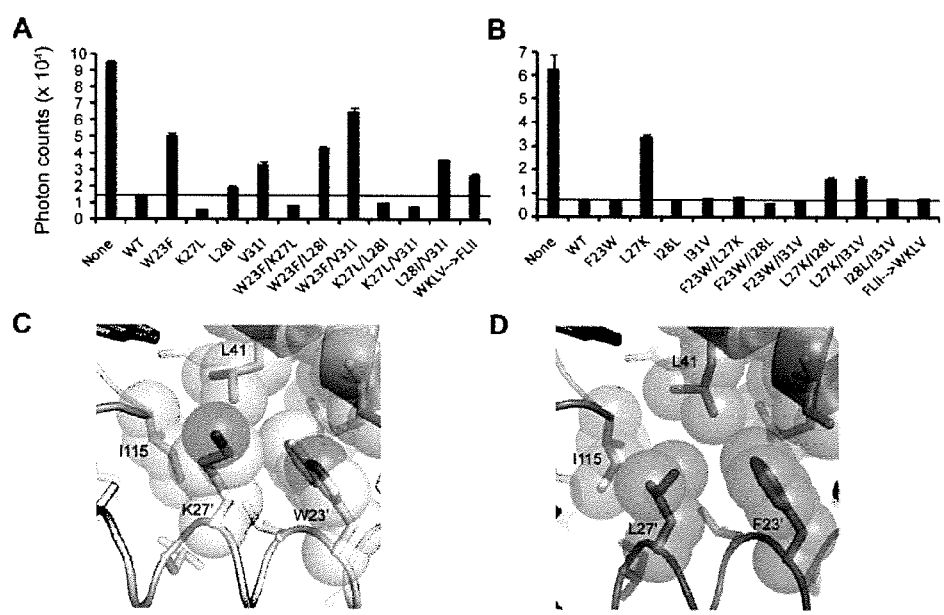
FIGS. 3A-3D demonstrate the binding of hybrid PTH/PTHrP peptides to the MBP-PTH1R ECD protein.

The receptor accommodates the slightly different binding modes with relatively minor changes including the shift in Ile 115 in response to the PTHrP curvature and the L41 rotamer toggle switch mechanism to maintain van der Waals contact with the ligands despite their different side chain volumes at position 23 (FIGS. 3C and 3D).

PTHrP was generally more tolerant to alteration than PTH with respect to ECD binding. Three out of the four single swap mutants of PTHrP retained normal binding to the ECD, but only one of the PTH single swap mutants did the same. The PTH interaction is probably more sensitive to the conservative substitutions because of its higher surface complementarity to the ECD and larger buried surface area, which leave less room for adjustments to the interface in response to mutation. This suggests that PTHrP may provide a better scaffold in which to introduce alterations for therapeutic analog development.

Initially the inventors suspected that the different ECD-binding modes of PTH and PTHrP might contribute to their different R0/RG selectivity profiles. While this does not appear to be the case, the availability of the high resolution structures did guide their rational design of the swap alterations that ultimately allowed them to obtain peptides highly selective for the G protein-coupled receptor. Surprisingly, RG-selectivity was enhanced by the swap mutations that diminished ECD binding. However, R0/RG selectivity is more complicated than just ECD affinity. PTH(1-28), which exhibits decreased ECD binding, was more RG-selective than PTH(1-34), but also had diminished RG affinity compared to PTH(1-34) (26). Clearly, residues 29-34 must contribute to the ability of the RG-selective hybrid PTH/PTHrP(1-34) peptides to retain normal RG binding. Thus, there are at least two different ways to alter the R0/RG selectivity profile of a given PTH or PTHrP peptide. RG-selectivity can be enhanced by His at position 5—presumably via interaction with the 7-TM domain of the receptor—and also by diminished ECD-binding by the C-terminal portion of the peptides, but residues 29-34 are important to retain normal RG binding.

The RG-selective peptides potently stimulated cAMP accumulation, but with a shorter signaling lifetime (FIG. 5), suggesting that these peptides provide a pulsatile action at the receptor. Although the underlying biochemical mechanisms responsible for the shorter duration of signaling are unclear, these peptides might act pharmacologically as "biased" agents that might induce the anabolic effects on bone while limiting the bone resorptive effects resulting from sustained stimulation of the receptor. Indeed, PTHrP appears to be a more purely anabolic agent than PTH, lacking adverse hypercalcemic side effects (17). If the decreased R0 affinity of PTHrP contributes to this effect, then the RG-selective peptides presented here, particularly PTHrP(1-34) [L27K], may have therapeutic potential as more purely anabolic analogs for treating osteoporosis.

In accordance with the foregoing, the present invention provides PTH peptides comprising the amino acid sequence of wild-type PTH (SEQ ID NO: 9) with amino acid substitutions at positions within the C-terminal half of the peptide (e.g., amino acids 15-34 of SEQ ID NO: 9). As shown herein for the first time, the PTH peptides of the present disclosures exhibit altered biological properties (e.g., decreased affinity for the G protein-uncoupled conformation (R0) of PTH1R, as compared to the affinity of wild-type PTH to the R0 conformation of PTH1R, while the PTH peptide retains binding to the G protein-coupled conformation (RG) of PTH1R, and is able to stimulates cAMP accumulation in cells; diminished binding to the ECD of the PTH1R), as compared to wild-type PTH. Such altered biological properties are believed to increase the therapeutic potential of these PTH peptides.

In some aspects, the PTH peptide provided herein comprises the amino acid sequence of wild-type PTH (SEQ ID NO: 9) with an amino acid substitution at one or more of the amino acids positions 12, 14, 16, 17, and 27 of SEQ ID NO: 9, or an analog thereof comprising a disulfide bond.

In some embodiments, the amino acid substitution at one or more of the specified positions of SEQ ID NO: 9 is a conservative amino acid substitution of the amino acid which is native to SEQ ID NO: 9. In specific embodiments, the conservative amino acid substitution is one which accords with the teachings described herein. See "Variant peptides." In exemplary embodiments, the conservative amino acid substitution is an exchange of one amino acid with another amino acid within one of the following groups:

I. Small aliphatic, nonpolar or slightly polar residues:
Ala, Ser, Thr, Pro, Gly;
II. Polar, negatively charged residues and their amides and esters:
Asp, Asn, Glu, Gln, cysteic acid and homocysteic acid;
III. Polar, positively charged residues:
His, Arg, Lys; Ornithine (Orn)
IV. Large, aliphatic, nonpolar residues:
Met, Leu, Ile, Val, Cys, Norleucine (Nle), homocysteine
V. Large, aromatic residues:
Phe, Tyr, Trp, acetyl phenylalanine In other embodiments, the amino acid substitution is a not a conservative amino acid substitution, e.g., is a non-conservative amino acid substitution.

Accordingly, in specific embodiments, the PTH peptide of the present disclosures comprises the sequence of SEQ ID NO: 53, wherein the amino acid at position 12 is Gly, Val, Ala, or a conservative substitution thereof, wherein the amino acid at position 14 is His, Phe, Leu, or a conservative substitution thereof, wherein the amino acid at position 16 is Asn, Thr, or a conservative substitution thereof, wherein the amino acid at position 17 is Ser, Asp, Asn, or a conservative substitution thereof, and wherein the amino acid at position 27 is Lys, Leu, or a conservative substitution thereof. In more specific embodiments, the PTH peptide of the present disclosures comprises the amino acid sequence of any of SEQ ID NOs: 1-10, and 13-20.

In some aspects, the PTH peptide of the present disclosures comprises the C-terminal half of wild-type PTH (amino acids 15-34 of SEQ ID NO: 9) with an amino acid substitution at one or more of positions 23, 27, 28, and 31 of SEQ ID NO: 9. In some embodiments, the PTH peptide exhibits decreased affinity for the G protein-uncoupled conformation (R0) of Parathyroid Hormone Receptor (PTH1R), as compared to the affinity of wild-type PTH (SEQ ID NO: 9) for the R0 conformation of PTH1R, yet retains binding to the G protein-coupled conformation (RG) of PTH1R, and stimulates cAMP accumulation in cells. In some embodiments, the PTH peptide additionally exhibits diminished binding to the extracellular domain (ECD) of PTH1R, as compared to the binding of wild-type PTH to the ECD of PTH1R.

In specific embodiments, the amino acid at one or more of positions 23, 27, 28, and 31 of SEQ ID NO: 9 is replaced with the amino acid at the corresponding position of SEQ ID NO: 79. For example, a replacement of the amino acid at position 23 of SEQ ID NO: 9 with the amino acid at the corresponding position of SEQ ID NO: 79 is a replacement of Trp with the amino acid at position 23 of SEQ ID NO: 79 (Phe). Likewise, for example, a replacement of the amino acid at position 19 of SEQ ID NO: 9 with the amino acid at the corresponding position of SEQ ID NO: 79 is a replacement of Glu with the amino acid at position 19 of SEQ ID NO: 79 (Arg).

In some embodiments, the PTH peptide comprises amino acids 15-34 of SEQ ID NO: 9 with an amino acid substitution at one or more of positions 23, 27, 28, and 31 of SEQ ID NO: 9 and further comprises amino acids 1-14 of SEQ ID NO: 9 at the N-terminus of the PTH peptide. In such embodiments, the PTH peptides comprises amino acids 1-34 of SEQ ID NO: 9 with an amino acid substitution at one or more of positions 23, 27, 28, and 31 of SEQ ID NO: 9. Accordingly, in some embodiments, the PTH peptide comprises the amino acid sequence of any of SEQ ID NOs: 57-66.

In some aspects, the PTH peptide comprises amino acids 15-34 of SEQ ID NO: 9, with an amino acid substitution at one or more of positions 20, 21, 23, 24, 27, 28, and 34. In specific embodiments, the PTH peptide exhibits diminished binding to the extracellular domain (ECD) of PTH1R, as compared to the binding of wild-type PTH to the ECD of PTH1R. In some embodiments, the PTH peptide exhibits decreased affinity for the G protein-uncoupled conformation (R0) of PTH1R, as compared to the affinity of wild-type PTH (SEQ ID NO: 9) for the R0 conformation of PTH1R, wherein the PTH peptide retains binding to the G protein-coupled conformation (RG) of PTH1R, and wherein the PTH peptide stimulates cAMP accumulation in cells. In some embodiments, PTH peptide comprises an amino acid substitution at position 23 or 28, or at both positions 23 and 28. In some embodiments, the PTH peptide additionally comprises an amino acid substitution at one or more of positions 21, 27, and 34.

In some embodiments, the PTH peptide comprises amino acids 15-34 of SEQ ID NO: 9, with an amino acid substitution at one or more of positions 20, 21, 23, 24, 27, 28, and 34 of SEQ ID NO: 9 and further comprises amino acids 1-14 of SEQ ID NO: 9 at the N-terminus of the PTH peptide. In such embodiments, the PTH peptides comprises amino acids 1-34 of SEQ ID NO: 9, with an amino acid substitution at one or more of positions 20, 21, 23, 24, 27, 28, and 34.

The amino acid substitutions at the specified positions may be conservative or non-conservative amino acid substitutions, in accordance with the descriptions thereof herein. In specific embodiments, the amino acid substitution is a replacement of the amino acid of the native amino acid at the specified position(s) with Ala. Accordingly, in specific embodiments, the PTH peptide comprises an Ala at one or more of positions 20, 21, 23, 24, 27, 28, and 34. As such, in some embodiments, the PTH peptide comprises the amino acid sequence of any of SEQ ID NOs: 68-71, 73, 74, and 78.

In addition to the PTH peptides described herein, the invention further provides PTHrP peptides comprising the amino acid sequence of wild-type PTHrP (SEQ ID NO: 79) with amino acid substitutions at positions within the C-terminal half of the peptide (e.g., amino acids 12-34 of SEQ ID NO: 79). As shown herein for the first time, the PTHrP peptides of the present disclosures exhibit altered biological properties (e.g., decreased affinity for the G protein-uncoupled conformation (R0) of PTH1R, as compared to the affinity of wild-type PTHrP to the R0 conformation of PTH1R, while the PTHrP peptide retains binding to the G protein-coupled conformation (RG) of PTH1R, and is able to stimulate cAMP accumulation in cells; diminished binding to the ECD of the PTH1R), as compared to wild-type PTHrP. Such altered biological properties are believed to increase the therapeutic potential of these PTHrP peptides.

In some aspects, the PTHrP peptide comprises the C-terminal half of wild-type PTHrP (amino acids 12-34 of SEQ ID NO: 79) with an amino acid substitution at one or more of positions 23, 27, 28, and 31 or SEQ ID NO: 79. In specific aspects, the PTHrP peptide exhibits decreased affinity for the G protein-uncoupled conformation (R0) of PTH1R, as compared to the affinity of wild-type PTHrP (SEQ ID NO: 79) for the R0 conformation of PTH1R, yet retains binding to the G protein-coupled conformation (RG) of PTH1R, and stimulates cAMP accumulation in cells. In some embodiments, the PTHrP peptide additionally exhibits diminished binding to the ECD of PTH1R, as compared to the binding of wild-type PTHrP to the ECD or PTH1R.

In specific embodiments, the amino acid at one or more of positions 23, 27, 28, and 31 of SEQ ID NO: 79 is replaced with the amino acid at the corresponding position of SEQ ID NO: 9. For example, a replacement of the amino acid at position 23 of SEQ ID NO: 79 with the amino acid at the corresponding position of SEQ ID NO: 9 is a replacement of Phe with the amino acid at position 23 of SEQ ID NO: 9 (Trp). Likewise, for example, a replacement of the amino acid at position 5 of SEQ ID NO: 79 with the amino acid at the corresponding position of SEQ ID NO: 9 is a replacement of His with the amino acid at position 5 of SEQ ID NO: 9 (Ile).

In some embodiments, the PTHrP peptide comprises amino acids 12-34 of SEQ ID NO: 79) with an amino acid substitution at one or more of positions 23, 27, 28, and 31 or SEQ ID NO: 79 and further comprises amino acids 1-11 of SEQ ID NO: 79 at the N-terminus of the PTHrP peptide. In such embodiments, the PTHrP peptide comprises amino acids 1-34 of SEQ ID NO: 79 with an amino acid substitution at one or more of positions 23, 27, 28, and 31 of SEQ ID NO: 79. Accordingly, in some embodiments, the PTHrP peptide comprises the amino acid sequence of any of SEQ ID NOs: 80-90.

In some aspects, the PTHrP peptide comprises amino acids 12-34 of SEQ ID NO: 79, with an amino acid substitution at one or more of positions 20, 21, 23, 24, 27, 28, 32, and 33. In specific aspects, the PTHrP peptide exhibits diminished binding to the ECD of PTH1R, as compared to the binding of wild-type PTHrP to the ECD or PTH1R. In some embodiments, the PTH peptide exhibits decreased affinity for the G protein-uncoupled conformation (R0) of PTH1R, as compared to the affinity of wild-type PTHrP (SEQ ID NO: 79) to the R0 conformation of PTH1R, wherein the PTHrP peptide retains binding to the G protein-coupled conformation (RG) of PTH1R, and wherein the PTHrP peptide stimulates cAMP accumulation in cells. In some embodiments, the PTHrP peptide comprises an amino acid substitution at position 22 or 27, or at both positions 22 and 27.

In some embodiments, the PTHrP peptide comprises amino acids 12-34 of SEQ ID NO: 79, with an amino acid substitution at one or more of positions 20, 21, 23, 24, 27, 28, 32, and 33 and further comprises amino acids 1-11 of SEQ ID NO: 79 at the N-terminus of the PTHrP peptide. In such embodiments, the PTHrP peptide comprises amino acids 1-34 of SEQ ID NO: 79 with an amino acid substitution at one or more of positions 20, 21, 23, 24, 27, 28, 32, and 33 of SEQ ID NO: 79.

The amino acid substitutions at the specified positions may be conservative or non-conservative amino acid substitutions, in accordance with the descriptions thereof herein. In specific embodiments, the amino acid substitution is a replacement of the amino acid of the native amino acid at the specified position(s) with Ala. Accordingly, in specific embodiments, the PTHrP peptide comprises an Ala at one or more of positions 20, 21, 23, 24, 27, 28, 32, and 33. As such, in some embodiments, the PTHrP peptide comprises the amino acid sequence of any of SEQ ID NOs: 93-98, 100, and 101.

Activity of the PTH Peptides and PTHrP Peptides

In some aspects of the present disclosures, the PTH peptides, analogs thereof, and PTHrP peptides are potent agonists of the PTH1R. In exemplary embodiments, the PTH peptides, analogs thereof, and PTHrP peptides exhibit an EC50 at the PTH1R of at least or about the same as wild-type PTH or PTHrP at the PTH1R receptor. In some embodiments, the potency of the PTH peptide or PTHrP peptide of the present disclosures (which is calculated by dividing the EC50 of wild-type PTH or PTHrP at the PTH1R by the EC50 of the PTH peptide or PTHrP peptide of the present disclosures and then multiplying this number by 100%) is at least or about 10%, at least or about 15%, at least or about 20%, at least or about 25%, at least or about 30%, at least or about 35%, at least or about 40%, at least or about 45%, at least or about 50%, at least or about 55%, at least or about 60%, at least or about 65%, at least or about 70%, at least or about 75%, at least or about 80%, at least or about 85%, at least or about 90%, at least or about 95%, at least or about 100%, at least or about 200%, at least or about 500%, at least or about 1000%.

As discussed herein, activation of the PTH1R by PTH and PTHrP lead to cAMP accumulation in cells, e.g., osteoblasts. In some aspects of the present disclosures, the PTH peptides, analogs thereof, and PTHrP peptides are potent agonists of the PTH1R and lead to significant cAMP accumulation in cells. In specific embodiments, the response at the PTH1R stimulated by the PTH peptides and PTHrP peptides, or analogs thereof, is shorter-lived cAMP response as compared to the cAMP response of wild-type PTH (SEQ ID NO: 9) or wild-type PTHrP (SEQ ID NO: 79). In some specific embodiments, the PTH peptide comprises SEQ ID NO: 64. In some specific embodiments, the PTHrP peptide comprises SEQ ID NO: 81.

Analogs of PTH Peptides and PTHrP Peptides

Further provided herein are analogs of the PTH peptides described herein (e.g., a PTH peptide comprising the amino acid sequence of wild-type PTH (SEQ ID NO: 9) with an amino acid substitution at one or more of the amino acids positions 12, 14, 16, 17, and 27) which analogs comprise an intramolecular bridge which links two non-consecutive amino acids. In specific embodiments, the intramolecular bridge is a disulfide bond. In some embodiments, in which the analog comprises a disulfide bond, the PTH peptide comprises further amino acid substitutions in which the amino acid native to SEQ ID NO: 9 is substituted with a sulfur-containing amino acid (e.g., Cys (e.g., L-Cys, D-Cys), cysteic acid, homocysteic acid, and the like).

Accordingly, in some embodiments, the analog comprises the amino acid sequence of any of SEQ ID NOs: 54-56, wherein two of the amino acids at positions 19, 22, and 25 are linked by a disulfide bond. In specific embodiments, the disulfide bond links the amino acid at position 19 to the amino acid at position 22. In yet more specific embodiments, the amino acid at position 19 is D-Cys and the amino acid at position 22 is Cys. In other specific embodiments, the disulfide bond of the analog links the amino acid at position 22 to the amino acid at position 25, and in more specific embodiments, each of the amino acids at positions 22 and 25 is Cys. In accordance with the foregoing, in certain embodiments, the analog comprises the amino acid sequence of any of SEQ ID NOs: 11, 12, and 21-52.

Also provided herein are analogs of the PTHrP peptides described herein (e.g., a PTHrP peptide comprising the amino acid sequence of wild-type PTHrP (SEQ ID NO: 79) with an amino acid substitution at one or more of the amino acids within the C-terminal portion of the PTHrP peptide (amino acids 12-34 of SEQ ID NO: 79), which analogs comprise an intramolecular bridge which links two non-consecutive amino acids. In specific embodiments, the intramolecular bridge is a disulfide bond. In some embodiments, in which the analog comprises a disulfide bond, the PTHrP peptide comprises further amino acid substitutions in which the amino acid native to SEQ ID NO: 79 is substituted with a sulfur-containing amino acid (e.g., Cys (e.g., L-Cys, D-Cys), cysteic acid, homocysteic acid, and the like). In some embodiments, the analog comprises a disulfide bond at positions 19 and 22 or at positions 22 and 25.

Variant Peptides

A "variant" of the PTH or PTHrP peptide or polypeptide analog refers to a molecule that is substantially identical to either the peptide or polypeptide analog in which one or more amino acid residues have been replaced (substitution variant) or which has one or more residues deleted (deletion variant) or added (addition variant). Preferably such substitution, addition, or deletion results in improved biological activity or improved clinical properties without significantly diminishing the desired biological or biochemical effect. It is within the skill in the art to assess whether a proposed substitution, addition, or deletion of one or more residues will have the desired impact on the peptide. For a detailed description of protein chemistry and structure, see Schulz, G. E. et al., Principles of Protein Structure, Springer-Verlag, New York, 1979, and Creighton, T. E., Proteins: Structure and Molecular Principles, W.H. Freeman & Co., San Francisco, 1984, which are hereby incorporated by reference. The types of substitutions which may be made in the peptide molecule of the present invention are conservative substitutions and are defined herein as exchanges within one of the following groups: 1. Small aliphatic, nonpolar or slightly polar residues: e.g., Ala, Ser, Thr, Gly; 2. Polar, negatively charged residues and their amides: e.g., Asp, Asn, Glu, Gln; 3. Polar, positively charged residues: e.g., His, Arg, Lys; Pro, because of its unusual geometry, tightly constrains the chain. Substantial changes in functional properties are made by selecting substitutions that are less conservative, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain. Most substitutions according to the present invention are those which do not produce radical changes in the characteristics of the peptide molecule. Even when it is difficult to predict the exact effect of a substitution in advance of doing so, one skilled in the art will appreciate that the effect can be evaluated by routine screening assays, preferably the biological and biochemical assays described herein. Modifications of peptide properties including redox or thermal stability, hydrophobicity, susceptibility to proteolytic degradation or the tendency to aggregate with carriers or into multimers are assayed by methods well known to the ordinarily skilled artisan.

A variant may have 50% sequence identity to one of the present PTH or PTHrP peptide or polypeptide analogs, or 60%, 70%, 80%, 90%, 95%, 96%, 97%, 98%, or 99% sequence identity to PTH or PTHrP peptide or polypeptide analog.

Additional Modifications of PTH Peptides or PTHrP Peptides

Also included are peptides and polypeptides wherein one or more L-amino acids has/have been substituted for one or more D-amino acids. Additionally, modified amino acids or chemical derivatives of amino acids may be provided such that the peptide contains additional chemical moieties or modified amino acids not normally a part of a natural protein. Such derivatized moieties may improve the solubility, absorption, biological half life, and the like. Moieties capable of mediating such effects are disclosed, for example, in Remington's Pharmaceutical Sciences, 16th ed., Mack Publishing Co., Easton, Pa. (1980). Chemical derivatives are described further herein. See "Chemical Derivatives."

The peptides described herein can be glycosylated, amidated, carboxylated, phosphorylated, esterified, N-acylated, cyclized via, e.g., a disulfide bridge, or converted into an acid addition salt and/or optionally dimerized or polymerized, or conjugated.

C-Terminal Amidation

As further discussed herein, the PTH peptide, PTHrP peptide, or analog thereof, of the present disclosures in some embodiments comprises a C-terminal amide group in place of a C-terminal carboxylic acid. In such cases, the backbone of the C-terminal residue comprises $N-C_{alpha}-CONH_2$.

Salts

In some embodiments, the PTH peptide or PTHrP peptide (including analog or variant thereof) is in the form of a salt, e.g., a pharmaceutically acceptable salt. As used herein the term "pharmaceutically acceptable salt" refers to salts of compounds that retain the biological activity of the parent compound, and which are not biologically or otherwise undesirable. Such salts can be prepared in situ during the final isolation and purification of the analog, or separately prepared by reacting a free base function with a suitable acid. Many of the compounds disclosed herein are capable of forming acid and/or base salts by virtue of the presence of amino and/or carboxyl groups or groups similar thereto.

Pharmaceutically acceptable acid addition salts may be prepared from inorganic and organic acids. Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenyl-propionate, picrate, pivalate, propionate, succinate, tartrate, thiocyanate, phosphate, glutamate, bicarbonate, p-toluenesulfonate, and undecanoate. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Examples of acids which can be employed to form pharmaceutically acceptable acid addition salts include, for example, an inorganic acid, e.g., hydrochloric acid, hydrobromic acid, sulphuric acid, and phosphoric acid, and an organic acid, e.g., oxalic acid, maleic acid, succinic acid, and citric acid.

Basic addition salts also can be prepared in situ during the final isolation and purification of the source of salicylic acid, or by reacting a carboxylic acid-containing moiety with a suitable base such as the hydroxide, carbonate, or bicarbonate of a pharmaceutically acceptable metal cation or with ammonia or an organic primary, secondary, or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, and ethylammonium, amongst others. Other representative organic amines useful for the formation of base addition salts include, for example, ethylenediamine, ethanolamine, diethanolamine, piperidine, piperazine, and the like. Salts derived from organic bases include, but are not limited to, salts of primary, secondary and tertiary amines.

Further, basic nitrogen-containing groups can be quaternized with the PTH peptide or PTHrP peptide of the present disclosure as lower alkyl halides such as methyl, ethyl, propyl, and butyl chlorides, bromides, and iodides; long chain halides such as decyl, lauryl, myristyl, and stearyl chlorides, bromides, and iodides; arylalkyl halides like benzyl and phenethyl bromides and others. Water or oil-soluble or dispersible products are thereby obtained.

Chemical Derivatives

A "chemical derivative" of the PTH or PTHrP peptide or polypeptide analog refers to a molecule that contains additional chemical moieties not normally a part of the PTH or PTHrP protein. Covalent modifications of the protein are included within the scope of this invention. Such modifications may be introduced into the molecule by reacting targeted amino acid residues with an organic derivatizing agent that is capable of reacting with selected side chains or terminal residues. Such chemically derivatized moieties may improve the protein's solubility, absorption, biological half life, and the like. These changes may eliminate or attenuate undesirable side effects of the PTH or PTHrP peptide or polypeptide analog in vivo. Moieties capable of mediating such effects are disclosed, for example, in Remington's Pharmaceutical Sciences, Mack Publishing Company, Easton Pa. (Gennaro 18th ed. 1990). Capped peptides discussed below are examples of preferred chemical derivatives of a "natural" uncapped peptide. Any of the present combination of substitution, addition, or deletion variants may be capped with any of the capping groups disclosed herein.

Chemical Moieties

The chemical moiety which is a part of the chemical derivative can be any chemical moiety, including naturally-occurring or non-naturally-occurring, biological molecules, chemical compounds, e.g., small M.W. compounds, which in some embodiments, are chemically inert to the PTH peptide or PTHrP peptide. Generally, the chemical moiety is one which does not decrease the activity of the peptide. Alternatively, the chemical moiety is one which alters (e.g., improves or enhances) the properties of the PTH peptide or PTHrP peptide, e.g., increases stability, solubility, and/or potency of the peptide, decreases duration of action at the PTH1R, increases selectivity for RG, decreases the affinity for R0. In a specific embodiments, the chemical moiety is a polymer, a carbohydrate, an amino acid, a peptide, or a lipid, e.g., a fatty acid or a steroid.

In some embodiments, the chemical moiety is an amino acid. The amino acid may be any of the 20 common amino acids known in the art (Ala, Cys, Asp, Glu, Phe, Gly, His, Ile, Lys, Leu, Met, Asn, Pro, Arg, Ser, Thr, Val, Trp, Tyr) or any known non-naturally-occurring amino acids. Suitable synthetic amino acids for purposes herein include but not limited to β-alanine (β-Ala), N-α-methyl-alanine (Me-Ala), aminobutyric acid (Abu), γ-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl) alanine, α-tert-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met(O$_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-NO$_2$)), 4-cyanophenylalanine ((Phe(4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid. The amino acid may be a D-isomer of the amino acid or the L-isomer.

In some embodiments, the chemical moiety is a peptide, e.g., a peptide of 50 amino acids or less, e.g., a dipeptide, a tripeptide, a 4-mer, 5-mer, 6-mer, 7-mer, 8-mer, 9-mer, 10-mer, 15-mer, 20-mer, 25-mer, 30-mer, 35-mer, 40-mer, 45-mer, 50-mer. The peptide may comprise any of the amino acids known in the art, such as any of those described herein.

The polymer may be any polymer. The polymer may be a derivatized polymer of any of: polyamides, polycarbonates, polyalkylenes and derivatives thereof including, polyalkylene glycols, polyalkylene oxides, polyalkylene terepthalates, polymers of acrylic and methacrylic esters, including poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

The polymer can be a biodegradable polymer, including a synthetic biodegradable polymer (e.g., polymers of lactic acid and glycolic acid, polyanhydrides, poly(ortho)esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

The polymer can be a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In some embodiments, the polymer is a water-soluble polymer. Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof.

The carbohydrate may be any carbohydrate. The carbohydrate may be for example a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

The lipid may be any lipid, for example, a fatty acid (e.g., a C4-C30 fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, a polyketide, oil, wax, cholesterol, sterol, fat-soluble vitamin, monoglyceride, diglyceride, triglyceride, a phospholipid.

The peptide can be linked to the chemical moiety via direct covalent linkage by reacting targeted amino acid residues of the peptide with an organic derivatizing agent that is capable of reacting with selected side chains or the N- or C-terminal residues of these targeted amino acids. Reactive groups on the peptide or chemical moiety include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art.

Cysteinyl residues are most commonly are reacted with α-haloacetates (and corresponding amines), such as chloroacetic acid, chloroacetamide to give carboxymethyl or carboxyamidomethyl derivatives. Cysteinyl residues also are derivatized by reaction with bromotrifluoroacetone, alpha-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are derivatized with succinic or other carboxylic acid anhydrides. Derivatization with a cyclic carboxylic anhydride has the effect of reversing the charge of the lysinyl residues. Other suitable reagents for derivatizing .quadrature.-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl side groups, aspartyl or glutamyl, may be selectively modified by reaction with carbodiimides (R—N.dbd. C.dbd.N—R') such as 1-cyclohexyl-3-(2-morpholinyl-(4-ethyl)carbodiimide or 1-ethyl-3-(4-azonia-4,4-dimethylpentyl)carbodiimide. Furthermore, aspartyl and glutamyl residues can be converted to asparaginyl and glutaminyl residues by reaction with ammonia.

Other modifications include hydroxylation of proline and lysine, phosphorylation of hydroxyl groups of seryl or threonyl residues, methylation of the amino group of lysine (Creighton, supra, pp. 79-86), acetylation of the N-terminal amine, and amidation of the C-terminal carboxyl groups.

Another type of covalent modification involves chemically or enzymatically coupling glycosides to the peptide. Sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

The chemical moiety can be linked to the peptide indirectly through a linker. As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups. In some embodiments, the linker is an intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

Fusion Proteins

The present invention includes a "fusion protein" comprising the PTH or PTHrP peptide or polypeptide analog (variant or chemical derivative) that is fused to another peptide or polypeptide that confers useful properties on the fusion protein. For example, the PTH or PTHrP peptide or polypeptide analog can be fused to a polypeptide that promotes uptake of the PTH or PTHrP peptide or polypeptide analog by a cell.

In some embodiments, the PTH or PTHrP peptide or polypeptide analog (variant or chemical derivative) is directly fused to the other peptide or polypeptide. In specific embodiments, the PTH or PTHrP peptide or polypeptide analog (variant or chemical derivative) is positioned N-terminal to the other peptide or polypeptide. In other embodiments, the PTH or PTHrP peptide or polypeptide analog (variant or chemical derivative) is positioned C-terminal to the other peptide or polypeptide.

In some embodiments, the PTH or PTHrP peptide or polypeptide analog (variant or chemical derivative) is fused to the other peptide or polypeptide via a linker. Suitable linkers are known in the art, and include, but not limited to an amino acid (e.g., any of the amino acids described herein) and a peptide (a dipeptide, a tripeptide, a 4-mer, 5-mer, 6-mer, 7-mer, 8-mer, 9-mer, 10-mer, 15-mer, 20-mer, 25-mer, 30-mer, 35-mer, 40-mer, 45-mer, 50-mer). Suitable amino acids and peptides include those known in the art (e.g., any of those described herein in "*Chemical Moieties.*"

The other peptide to which the PTH peptide or PTHrP (or analog or variant thereof) is fused may be a plasma protein, a secretion signal, a targeting moiety, a cytokine, a soluble factor, or an immunoglobulin or portion thereof (e.g. variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC).

For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In a related embodiments, the Fc region may comprise one or more native or modified constant regions from an immunoglobulin heavy chain, other than CH1, for example, the CH2 and CH3 regions of IgG and IgA, or the CH3 and CH4 regions of IgE.

Suitable other peptides to which the PTH peptide or PTHrP peptide is fused to include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain.

Some may or may not include FcγR binding site(s). FcγR are responsible for ADCC and CDC. Examples of positions within the Fc region that make a direct contact with FcγR are amino acids 234-239 (lower hinge region), amino acids 265-269 (B/C loop), amino acids 297-299 (C'/E loop), and amino acids 327-332 (F/G) loop (Sondermann et al., Nature 406:267-273, 2000). The lower hinge region of IgE has also been implicated in the FcRI binding (Henry, et al., Biochemistry 36, 15568-15578, 1997). Residues involved in IgA receptor binding are described in Lewis et al., (J Immunol. 175:6694-701, 2005). Amino acid residues involved in IgE receptor binding are described in Sayers et al. (J Biol Chem. 279(34):35320-5, 2004).

Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J Biol Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591). Amino acid modifications at positions 233-236 of IgG1 have been made that reduce binding to FcγRs (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety.

Multimers

The present invention also includes "multimeric peptides", i.e., longer peptides or polypeptides in which the basic peptidic sequence of a PTH or PTHrP peptide or polypeptide analog is repeated from about two to about 100 times, with or without intervening spacers or linkers. In one embodiment, a multimer of the peptide SEQ ID NO: 10 (referred to symbolically in this section as "JJJ" where J, J and J do not represent single amino acids) is shown by the following formulaic example:

(JJJ-$X_m$)$_n$-JJJ wherein m=0 or 1, n=1-100. X is a spacer group, preferably $C_1$-$C_{20}$ alkyl, $C_1$-$C_{20}$ alkenyl, $C_1$-$C_{20}$ alkynyl, $C_1$-$C_{20}$ polyether containing up to 9 oxygen atoms or Glyz. (z=1-10).

It is understood that such multimers may be built from any of the peptides or polypeptides described herein. Moreover, such a multimer may comprise different combinations of peptide monomers and the disclosed variants thereof. Such oligomeric or multimeric peptides can be made by chemical synthesis or by recombinant DNA techniques as discussed herein. When produced chemically, the oligomers preferably have from 2-8 repeats of the basic peptide sequence. When produced recombinantly, the multimers may have as many repeats as the expression system permits, for example from two to about 100 repeats.

Peptidomimetics

Another class of compounds useful in this regard are low molecular weight "peptidomimetic compounds" (which term also includes peptidomimetic). Such peptidomimetics may be identified by structural studies which compare the co-crystallization of one of the PTH or PTHrP peptide or polypeptide analogs with the PTH receptor in the presence or absence of a candidate peptidomimetic.

A peptidomimetic of a PTH or PTHrP peptide or polypeptide analog mimics the biological effect of one of the PTH or PTHrP peptide or polypeptide analogs. A peptidomimetic agent may be an unnatural peptide or a non-peptide agent which has the stereochemical properties of the PTH or PTHrP peptide or polypeptide analog such that it has the binding activity or biological activity of the peptide. Hence, this invention includes compounds wherein a peptidomimetic compound is coupled to another peptide.

A peptidomimetic agent may be an unnatural peptide or a non-peptide agent which recreates the stereospatial properties of the binding elements of the PTH or PTHrP peptide or polypeptide analog such that it has the binding activity or biological activity of the PTH or PTHrP peptide or polypeptide analog. Similar to the linear peptides corresponding to the PTH or PTHrP peptide or polypeptide analogs, a peptidomimetic might have a binding face (which interacts with the PTH receptor) and a non-binding face. Again, similar to the linear peptides of the PTH or PTHrP peptide or polypeptide analogs, the non-binding face of a peptidomimetic might contain functional groups which can be modified by various therapeutic moieties without modifying the binding face of the peptidomimetic. One embodiment of a peptidomimetic might contain an aniline on the non-binding face of the molecule. The $NH_2$-group of an aniline has a $pK_a$ of about 4.5 and could therefore be modified by any $NH_2$-selective reagent without modifying any $NH_2$ functional groups on the binding face of the peptidomimetic. Other peptidomimetics might not have any $NH_2$ functional groups on their binding face and therefore, any $NH_2$, without regard for $pK_a$ could be displayed on the non-binding face as a site for conjugation. In addition other modifiable functional groups, such as —SH and —COOH could be incorporated into the non-binding face of a peptidomimetic as a site of conjugation. A therapeutic moiety could also be directly incorporated during the synthesis of a peptidomimetic and preferentially be displayed on the non-binding face of the molecule.

This invention also includes compounds which retain partial peptide characteristics. For example, any proteolytically unstable bond within a peptide of the invention could be selectively replaced by a non-peptidic element such as an isostere (N-methylation; D-amino acid at the S1 site) or a reduced peptide bond while the rest of the molecule retains its peptide nature.

Peptidomimetic compounds, either agonists, substrates or inhibitors, have been described for a number of bioactive peptides such as opioid peptides, VIP, thrombin, HIV protease, etc. Methods for designing and preparing peptidomimetic compounds are known in the art (Hruby, V. J., Biopolymers 33:1073-1082 (1993); Wiley, R. A. et al., Med. Res. Rev. 13:327-384 (1993); Moore et al., Adv. in Pharmacol 33:91-141 (1995); Giannis et al., Adv. in Drug Res. 29:1-78 (1997), which references are incorporated by reference in their entirety). These methods are used to make peptidomimetics that possess at least the binding capacity and specificity of the cyclic peptides and preferably also possess the biological activity. Knowledge of peptide chemistry and general organic chemistry available to those skilled in the art are sufficient, in view of the present disclosure, for designing and synthesizing such compounds. For example, such peptidomimetics may be identified by inspection of the cystallographically-derived three-dimensional structure of a peptide of the invention either free or bound in complex with the PTH receptor. Alternatively, the structure of a peptide of the invention bound to the PTH receptor can be gained by using nuclear magnetic resonance spectroscopy. The better knowledge of the stereochemistry of the interaction of a peptide with its binding partner will permit the rational design of such peptidomimetic agents.

Peptoids

The present invention also includes "peptoids" which are oligomers of N-substituted glycines (Simon R J et al., Proc Natl Acad Sci USA, 1992 89:9367-9371). The 'peptoid' approach to the design of non-peptide, small molecule agonists and antagonists are also described by Horwell D C, Trends Biotechnol, 1995, 13:132-134. A peptoid of an PTH or PTHrP peptide or polypeptide analog would include substitution with, or addition of one or more such N-substituted glycines. The substituting group may be 4-aminophenol, isobutylamine, butyldiamine ($NH_2$ $(CH_2)_3NH_2$), cyclohexanemethylamine, aminomethylcyclopropane, benzylamine, methylamine, isopropylamine, R(+)-(L-methylbenzylamine), 5-(–1-alpha.-methylbenzylamine, N-3-guanidinopropyl, etc. Such substituents have previously been demonstrated to lead to increased bioactivity of SH3-binding peptoids by Nguyen. J. T. et al., Science 1998, 282:2088-2092. However, the substituting group can be virtually any substituent that can be substituted at the N position in glycine as long as the N-glycine product can be further coupled in a peptoid.

A PTH or PTHrP peptide or polypeptide analog of the present invention, e.g., the peptide of SEQ ID NO. 10, may be blocked or capped at its amino and carboxyl termini, e.g., with acetyl bound to the amino-terminal N ("Ac") and amido (—$NH_2$ bound to the C-terminal carboxyl group ("Am")), respectively. This peptide may be referred to in single letter code indicating the blocking groups as Ac and Am groups: Ac—the residues of SEQ ID No. 10-Am.

The N-terminal capping function is preferably linked to the terminal amino function and may be selected from the group consisting of: formyl; alkanoyl, having from 1 to 10 carbon atoms, such as acetyl, propionyl, butyryl; alkenyl, having from 1 to 10 carbon atoms, such as hex-3-enoyl; alkynoyl, having from 1 to 10 carbon atoms, such as hex-5-ynoyl; aroyl, such as benzoyl or 1-naphthoyl; heteroaroyl, such as 3-pyrroyl or 4-quinoloyl; alkylsulfonyl, such as methanesulfonyl; arylsulfonyl, such as benzenesulfonyl or sulfanilyl; heteroarylsulfonyl, such as pyridine-4-sulfonyl; substituted alkanoyl, having from 1 to 10 carbon atoms, such as 4-aminobutyryl; substituted alkenoyl, having from 1 to 10 carbon atoms, such as 6-hydroxy-hex-3-enoyl; substituted alkynoyl, having from 1 to 10 carbon atoms, such as 3-hydroxy-hex-5-ynoyl; substituted aroyl, such as 4-chlorobenzoyl or 8-hydroxy-naphth-2-oyl; substituted heteroaroyl, such as 2,4-dioxo-1,2,3,4-tetrahydro-3-methyl-quinazolin-6-oyl; substituted alkylsulfonyl, such as 2-aminoethanesulfonyl; substituted arylsulfonyl, such as 5-dimethylamino-1-naphthalenesulfonyl; substituted heteroarylsulfonyl, such as 1-methoxy-6-isoquinolinesulfonyl; carbamoyl or thiocarbamoyl; substituted carbamoyl (R'—NH—CO) or substituted thiocarbamoyl (R'—NH—CS) wherein R' is alkyl, alkenyl, alkynyl, aryl, heteroaryl, substituted alkyl, substituted alkenyl, substituted alkynyl, substituted aryl, or substituted heteroaryl; substituted carbamoyl (R'—NH—CO) or substituted thiocarbamoyl (R'—NH—CS) wherein R' is alkanoyl, alkenoyl, alkynoyl, aroyl, heteroaroyl, substituted alkanoyl, substituted alkenoyl, substituted alkynoyl, substituted aroyl, or substituted heteroaroyl, all as above defined; The C-terminal capping function can either be in an amide bond with the terminal carboxyl or in an ester bond with the terminal carboxyl. Capping functions that provide for an amide bond are designated as $NR^1R^2$ wherein $R^1$ and $R^2$ may be independently drawn from the following group: hydrogen; alkyl, preferably having from 1 to 10 carbon atoms, such as methyl, ethyl, isopropyl; alkenyl, preferably having from 1 to 10 carbon atoms, such as prop-2-enyl; alkynyl, preferably having from 1 to 10 carbon atoms, such as prop-2-ynyl; substituted alkyl having from 1 to 10 carbon atoms, such as hydroxyalkyl, alkoxyalkyl, mercaptoalkyl, alkylthioalkyl, halogenoalkyl, cyanoalkyl, aminoalkyl, alkylaminoalkyl, dialkylaminoalkyl, alkanoylalkyl, carboxyalkyl, carbamoylalkyl; substituted alkenyl having from 1 to 10 carbon atoms, such as hydroxyalkenyl, alkoxyalkenyl, mercaptoalkenyl, alkylthioalkenyl, halogenoalkenyl, cyanoalkenyl, aminoalkenyl, alkylaminoalkenyl, dialkylaminoalkenyl, alkanoylalkenyl, carboxyalkenyl, carbamoylalkenyl; substituted alkynyl having from 1 to 10 carbon atoms, such as hydroxyalkynyl, alkoxyalkynyl, mercaptoalkynyl, alkylthioalkynyl, halogenoalkynyl, cyanoalkynyl, aminoalkynyl, alkylaminoalkynyl, dialkylaminoalkynyl, alkanoylalkynyl, carboxyalkynyl, carbamoylalkynyl; aroylalkyl having up to 10 carbon atoms, such as phenacyl or 2-benzoylethyl; aryl, such as phenyl or 1-naphthyl; heteroaryl, such as 4-quinolyl; alkanoyl having from 1 to 10 carbon atoms, such as acetyl or butyryl; aroyl, such as benzoyl; heteroaroyl, such as 3-quinoloyl; OR' or NR'R" where R' and R" are independently hydrogen, alkyl, aryl, heteroaryl, acyl, aroyl, sulfonyl, sulfinyl, or SO2-R''' or SO—R''' where R''' is substituted or unsubstituted alkyl, aryl, heteroaryl, alkenyl, or alkynyl.

All the foregoing variants, fusion proteins, multimeric peptides, peptidomimetics, peptoids, and chemical derivatives of the PTH or PTHrP peptide or polypeptide analogs, as defined herein, must have the biological or biochemical activity of a PTH or PTHrP peptide or polypeptide analog as follows: at least about 20%, 30%, 40%, 50%, 60, 70%, 80%, 90%, 95%, 96%, 97%, 98%, or 99% of the activity of the PTH or PTHrP peptide or polypeptide analog in an in assay as identified in the Examples hereinbelow. Alternatively, or in addition, the foregoing variants, fusion proteins, multimeric peptides, peptidomimetics, peptoids, and chemical derivatives of the PTH or PTHrP peptide or polypeptide analogs should compete with labeled PTH or PTHrP peptide or polypeptide analogs for binding to the PTH receptor, when tested in a binding assay with whole cells, cell fractions, an isolated PTH receptor binding domain-containing protein or peptide, or any other binding molecule.

Retroinverso Peptides

For every peptide and polypeptide sequence disclosed herein, this invention includes the corresponding retro-inverso sequence wherein the direction of the peptide chain has been inverted and wherein all the amino acids belong to the D-series. The complete range of N-terminal capping groups and the complete range C-terminal capping groups specified for the L-series peptides are also intended for the D-series peptides.

Construction Methods

The peptides and polypeptides of the invention may be prepared using recombinant DNA technology. They also may be prepared using solid-phase synthesis, such as that generally described by Merrifield, J. Amer. Chem. Soc., 85:2149-54 (1963), although other equivalent chemical syntheses known in the art are also useful. Solid-phase peptide synthesis may be initiated from the C-terminus of the peptide by coupling a protected alpha-amino acid to a suitable resin. Such a starting material can be prepared by attaching an alpha-amino-protected amino acid by an ester linkage to a chloromethylated resin or to a hydroxymethyl resin, or by an amide bond to a BHA resin or MBHA resin.

The preparation of the hydroxymethyl resin is described by Bodansky et al., Chem. Ind., 38:1597-98 (1966). Chloromethylated resins are commercially available from BioRad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, 1-6. BHA and MBHA resin supports are commercially available and are generally used only when the desired polypeptide being synthesized has an unsubstituted amide at the C-terminus.

The amino acids can be coupled to the growing peptide chain using techniques well known in the art for the formation of peptide bonds. For example, one method involves converting the amino acid to a derivative that will render the carboxyl group of the amino acid more susceptible to reaction with the free N-terminal amino group of the growing peptide chain. Specifically, the C-terminal of the protected amino acid can be converted to a mixed anhydride by the reaction of the C-terminal with ethyl chloroformate, phenyl chloroformate, sec-butyl chloroformate, isobutyl chloroformate, or pivaloyl chloride or the like acid chlorides. Alternatively, the C-terminal of the amino acid can be converted to an active ester, such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole. Another coupling method involves the use of a suitable coupling agent, such as N,N'-dicyclohexylcarbodiimide or N,N'-diisopropylcarbodiimide. Other appropriate coupling agents, apparent to those skilled in the art, are disclosed in Gross et al., The Peptides: Analysis, Structure, Biology, Vol. I, "Major Methods of Peptide Bond Formation" (Academic Press 1979).

The alpha-amino group of each amino acid employed in the peptide synthesis must be protected during the coupling reaction to prevent side reactions involving their active alpha-amino function. Certain amino acids contain reactive side-chain functional groups (e.g., sulfhydryl, amino, carboxyl, and hydroxyl) and such functional groups must also be protected with suitable protecting groups to prevent a chemical reaction from occurring at either (1) the alpha-amino group site or (2) a reactive side chain site during both the initial and subsequent coupling steps.

In the selection of a particular protecting group to be used in synthesizing the peptides, the following general rules are typically followed. Specifically, an alpha-amino protecting group (1) should render the alpha-amino function inert under the conditions employed in the coupling reaction, (2) should be readily removable after the coupling reaction under conditions that will not remove side-chain protecting groups and will not alter the structure of the peptide fragment, and (3) should substantially reduce the possibility of racemization upon activation, immediately prior to coupling. On the other hand, a side-chain protecting group (1) should render the side chain functional group inert under the conditions employed in the coupling reaction, (2) should be stable under the conditions employed in removing the .alpha.-amino protecting group, and (3) should be readily removable from the desired fully-assembled peptide under reaction conditions that will not alter the structure of the peptide chain.

It will be apparent to those skilled in the art that the protecting groups known to be useful for peptide synthesis vary in reactivity with the agents employed for their removal. For example, certain protecting groups, such as triphenylmethyl and 2-(p-biphenyl)isopropyloxycarbonyl, are very labile and can be cleaved under mild acid conditions. Other protecting groups, such as t-butyloxycarbonyl (BOC), t-amyloxycarbonyl, adamantyl-oxycarbonyl, and p-methoxybenzyloxycarbonyl, are less labile and require moderately strong acids for their removal, such as trifluoroacetic, hydrochloric, or boron trifluoride in acetic acid. Still other protecting groups, such as benzyloxycarbonyl (CBZ or Z), halobenzyloxycarbonyl, p-nitrobenzyloxycarbonyl cycloalkyloxycarbonyl, and isopropyloxycarbonyl, are even less labile and require even stronger acids, such as hydrogen fluoride, hydrogen bromide, or boron trifluoroacetate in trifluoroacetic acid, for their removal. Suitable protecting groups, known in the art are described in Gross et al., The Peptides: Analysis, Structure, Biology, Vol. 3: "Protection of Functional Groups in Peptide Synthesis" (Academic Press 1981).

Some alpha-amino protecting groups are BOC and FMOC. For the side chain amino group present in Lys, protection may be by any of the groups mentioned above in (1) such as BOC, 2-chlorobenzyloxycarbonyl and the like. For the guanidino group of Arg, protection may be provided by nitro, tosyl, CBZ, adamantyloxycarbonyl, 2,2,5,7,8-pentamethylchroman-6-sulfonyl, 2,3,6-trimethyl-4-methoxyphenylsulfonyl, or BOC groups. For the hydroxyl group of Ser or Thr, protection may be, for example, by t-butyl; benzyl (BZL); or substituted BZL, such as p-methoxybenzyl, p-nitrobenzyl, p-chlorobenzyl, o-chlorobenzyl, and 2,6-dichlorobenzyl. For the carboxyl group of Asp or Glu, protection may be, for example, by esterification using such groups as BZL, t-butyl, cyclohexyl, cyclopentyl, and the like. For the imidazole nitrogen of His, the benzyloxymethyl (BOM) or tosyi moiety is suitably employed as a protecting group. For the phenolic hydroxyl group of Tyr, a protecting group such as tetrahydropyranyl, tert-butyl, trityl, BZL, chlorobenzyl, 4-bromobenzyl, and 2,6-dichlorobenzyl are suitably employed. The preferred protecting group is bromobenzyloxycarbonyl. For the side chain amino group of Asn or Gln, xanthyl (Xan) is preferably employed. For Met, the amino acid is preferably left unprotected. For the thio group of Cys, p-methoxybenzyl is typically employed.

Other standard alpha-amino group de-protecting reagents, such as HCl in dioxane, and conditions for the removal of specific .alpha.-amino protecting groups are within the skill of those working in the art, such as those described in Lubke et al., Chemie und Biochemie der Aminosauren, Peptide und Proteine I, Chapter II-1, 102-117 (Georg Thieme Verlag Stuttgart 1975). Following the removal of the alpha-amino protecting group, the unprotected alpha-amino group, generally still side-chain protected, can be coupled in a stepwise manner in the intended sequence.

An alternative to the stepwise approach is the fragment condensation method in which pre-formed peptides of short length, each representing part of the desired sequence, are coupled to a growing chain of amino acids bound to a solid phase support. For this stepwise approach, a particularly suitable coupling reagent is N,N'-dicyclohexylcarbodiimide or diisopropylcarbodiimide. Also, for the fragment approach, the selection of the coupling reagent, as well as the choice of the fragmentation pattern needed to couple fragments of the desired nature and size are important for success and are known to those skilled in the art.

Each protected amino acid or amino acid sequence is usually introduced into the solid-phase reactor in amounts in excess of stoichiometric quantities, and the coupling is suitably carried out in an organic solvent, such as dimethylformamide (DMF), CH2Cl2 or mixtures thereof. If incomplete coupling occurs, the coupling procedure is customarily repeated before removal of the N-amino protecting group in preparation for coupling to the next amino acid. Following the removal of the .alpha.-amino protecting group, the remaining .alpha.-amino and side-chain-protected amino acids can be coupled in a stepwise manner in the intended sequence. The success of the coupling reaction at each stage of the synthesis may be monitored. A preferred method of monitoring the synthesis is by the ninhydrin reaction, as described by Kaiser et al., Anal. Biochem., 34:595 (1970). The coupling reactions can also be performed automatically using well-known commercial methods and devices, for example, a Beckman 990 Peptide Synthesizer.

Upon completion of the desired peptide sequence, the protected peptide must be cleaved from the resin support, and all protecting groups must be removed. The cleavage reaction and removal of the protecting groups is suitably accomplished concomitantly or consecutively with de-protection reactions. When the bond anchoring the peptide to the resin is an ester bond, it can be cleaved by any reagent that is capable of breaking an ester linkage and of penetrating the resin matrix. One useful method is by treatment with liquid anhydrous hydrogen fluoride. This reagent will usually not only cleave the peptide from the resin, but will also remove all acid-labile protecting groups and, thus, will directly provide the fully de-protected peptide. When additional protecting groups that are not acid-labile are present, additional de-protection steps must be carried out. These steps can be performed either before or after the hydrogen fluoride treatment described above, according to specific needs and circumstances.

When it is desired to cleave the peptide without removing protecting groups, the protected peptide-resin can be subjected to methanolysis, thus yielding a protected peptide in which the C-terminal carboxyl group is methylated. This methyl ester can be subsequently hydrolyzed under mild alkaline conditions to give the free C-terminal carboxyl group. The protecting groups on the peptide chain can then be removed by treatment with a strong acid, such as liquid hydrogen fluoride. A particularly useful technique for methanolysis is that of Moore et al., Peptides, Proc. Fifth Amer. Pept. Symp., 518-521 (Goodman et al., eds., 1977), in which the protected peptide-resin is treated with methanol and potassium cyanide in the presence of a crown ether.

Other methods for cleaving a protected peptide from the resin when a chloromethylated resin is employed include (1) ammonolysis and (2) hydrazinolysis. If desired, the resulting C-terminal amide or hydrazide can be hydrolyzed to the free C-terminal carboxyl moiety, and the protecting groups can be removed conventionally. The protecting group present on the N-terminal .alpha.-amino group may be removed either before, or after, the protected peptide is cleaved from the support. Purification of the peptides of the invention is typically achieved using chromatographic techniques, such as preparative HPLC (including reverse phase HPLC), gel permeation, ion exchange, partition chromatography, affinity chromatography (including monoclonal antibody columns), and the like, or other conventional techniques such as countercurrent distribution or the like.

Pharmaceutical Compositions, Formulations, Routes, and Doses

A pharmaceutical composition according to this invention comprises the PTH or PTHrP peptide or polypeptide analog (and the variant, fusion protein, multimeric peptide, peptidomimetic, peptoid, and chemical derivative thereof) in a formulation that, as such, is known in the art. The pharmaceutical preparations of the present invention are manufactured in a manner which is known, for example, by means of conventional mixing, granulating, dissolving, or lyophilizing processes. Suitable excipients may include fillers binders, disintegrating agents, auxiliaries and stabilizers, all of which are known in the art. Suitable formulations for parenteral administration include aqueous solutions of the proteins in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension. It is imperative that the vehicle, carrier or excipient, as well as the conditions for formulating the composition are such that do not adversely affect the biological or pharmaceutical activity of the PTH or PTHrP peptide or polypeptide analog.

The compositions may be in the form of a lyophilized particulate material, a sterile or aseptically produced solution, a tablet, an ampule, etc. Vehicles, such as water (preferably buffered to a physiologically acceptable pH, as for example, in phosphate buffered saline) or other inert solid or liquid material such as normal saline or various buffers may be present. The particular vehicle is not critical, and those skilled in the art will know which vehicle to use for any particular utility described herein.

Other pharmaceutically acceptable carriers according to the present invention are liposomes, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension.

The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

The pharmaceutical formulation for systemic administration according to the invention may be formulated for enteral, parenteral or topical administration, and all three types of formulation may be used simultaneously to achieve systemic administration of the active ingredient.

In addition to the pharmacologically active peptide or polypeptide analog, the pharmaceutical compositions in some aspects contain suitable pharmaceutically acceptable carriers comprising excipients and auxiliaries which facilitate processing of the active compounds into preparations which can be used pharmaceutically as is well known in the art. Suitable solutions for administration by injection or orally, may contain from about 0.01 to 99 percent, active compound(s) together with the excipient.

The phrase "pharmaceutically acceptable" refers to molecular entities and compositions that are physiologically tolerable and do not typically produce an allergic or similar untoward reaction, such as gastric upset, dizziness and the like, when administered to a human Preferably, as used herein, the term "pharmaceutically acceptable" means approved by a regulatory agency of the Federal or a state government or listed in the U S Pharmacopeia or other generally recognized pharmacopeia for use in animals, and more particularly in humans. The pharmaceutical compositions of the present invention may be administered by any means that achieve their intended purpose. Amounts and regimens for the administration of can be determined readily by those with ordinary skill in the clinical art of treating any of the particular diseases. Preferred amounts are described below.

The present methods include administration by parenteral routes, including subcutaneous (s.c.) intravenous (i.v.), intramuscular, intraperitoneal, intrathecal, transdermal, topical or inhalation routes. A preferred route is by injection. Alternatively, or concurrently, administration may be by the oral route. The dosage administered will be dependent upon the age, health, and weight of the recipient, kind of concurrent treatment, if any, frequency of treatment, and the nature of the effect desired.

In the present method, the composition can be given one time but may be administered six to twelve times (or even more, as is within the skill of the art to determine empirically). The treatments can be performed daily but may be carried out every two to three days or as infrequently as once a week, depending on the beneficial and any toxic effects observed in the subject.

The pharmaceutical formulations disclosed herein may be designed to be short-acting, fast-releasing, long-acting, or sustained-releasing as described below. The pharmaceutical formulations may also be formulated for immediate release, controlled release or for slow release. The instant compositions may further comprise, for example, micelles or liposomes, or some other encapsulated form, or may be administered in an extended release form to provide a prolonged storage and/or delivery effect. The disclosed pharmaceutical formulations may be administered according to any regime including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi-monthly.

In accordance with some embodiments, a pharmaceutical composition is provided comprising any of the PTH peptides, PTHrP peptides (or related analogs or variants or chemical derivatives, fusion polypeptides, multimeric polypeptides, peptidomimetics, peptoids, retroinverso peptides) disclosed herein, preferably sterile and preferably at a purity level of at least 90%, 91%, 92%, 93%, 94%, 95%, 96%, 97%, 98% or 99%, and a pharmaceutically acceptable diluent, carrier or excipient. Such compositions may contain a PTH peptide or PTHrP peptide at a concentration of at least A, wherein A is 0.001 mg/ml, 0.01 mg/ml, 0.1 mg/ml, 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In other embodiments, such compositions may contain a PTH peptide or PTHrP peptide at a concentration of at most B, wherein B is 30 mg/ml, 25 mg/ml, 24 mg/ml, 23, mg/ml, 22 mg/ml, 21 mg/ml, 20 mg/ml, 19 mg/ml, 18 mg/ml, 17 mg/ml, 16 mg/ml, 15 mg/ml, 14 mg/ml, 13 mg/ml, 12 mg/ml, 11 mg/ml 10 mg/ml, 9 mg/ml, 8 mg/ml, 7 mg/ml, 6 mg/ml, 5 mg/ml, 4 mg/ml, 3 mg/ml, 2 mg/ml, 1 mg/ml, or 0.1 mg/ml. In some embodiments, the compositions may contain a PTH peptide or PTHrP peptide at a concentration range of A to B mg/ml, for example, 0.001 to 30.0 mg/ml. In one embodiment the pharmaceutical compositions comprise aqueous solutions that are sterilized and optionally stored within various containers. The PTH peptides or PTHrP peptides of the present disclosures can be used in accordance with one embodiment to prepare pre-formulated solutions ready for injection. In other embodiments the pharmaceutical compositions comprise a lyophilized powder. The pharmaceutical compositions can be further packaged as part of a kit, as further described herein, that includes a disposable device for administering the composition to a patient. The containers or kits may be labeled for storage at ambient room temperature or at refrigerated temperature.

The pharmaceutical composition can comprise any pharmaceutically acceptable ingredient, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents.

In some embodiments, the pharmaceutical composition comprises any one or a combination of the following components: acacia, acesulfame potassium, acetyltributyl citrate, acetyltriethyl citrate, agar, albumin, alcohol, dehydrated alcohol, denatured alcohol, dilute alcohol, aleuritic acid, alginic acid, aliphatic polyesters, alumina, aluminum hydroxide, aluminum stearate, amylopectin, α-amylose, ascorbic acid, ascorbyl palmitate, aspartame, bacteriostatic water for injection, bentonite, bentonite magma, benzalkonium chloride, benzethonium chloride, benzoic acid, benzyl alcohol, benzyl benzoate, bronopol, butylated hydroxyanisole, butylated hydroxytoluene, butylparaben, butylparaben sodium, calcium alginate, calcium ascorbate, calcium carbonate, calcium cyclamate, dibasic anhydrous calcium phosphate, dibasic dehydrate calcium phosphate, tribasic calcium phosphate, calcium propionate, calcium silicate, calcium sorbate, calcium stearate, calcium sulfate, calcium sulfate hemihydrate, canola oil, carbomer, carbon dioxide, carboxymethyl cellulose calcium, carboxymethyl cellulose sodium, β-carotene, carrageenan, castor oil, hydrogenated castor oil, cationic emulsifying wax, cellulose acetate, cellulose acetate phthalate, ethyl cellulose, microcrystalline cellulose, powdered cellulose, silicified microcrystalline cellulose, sodium carboxymethyl cellulose, cetostearyl alcohol, cetrimide, cetyl alcohol, chlorhexidine, chlorobutanol, chlorocresol, cholesterol, chlorhexidine acetate, chlorhexidine gluconate, chlorhexidine hydrochloride, chlorodifluoroethane (HCFC), chlorodifluoromethane, chlorofluorocarbons (CFC) chlorophenoxyethanol, chloroxylenol, corn syrup solids, anhydrous citric acid, citric acid monohydrate, cocoa butter, coloring agents, corn oil, cottonseed oil, cresol, m-cresol, o-cresol, p-cresol, croscarmellose sodium, crospovidone, cyclamic acid, cyclodextrins, dextrates, dextrin, dextrose, dextrose anhydrous, diazolidinyl urea, dibutyl phthalate, dibutyl sebacate, diethanolamine, diethyl phthalate, difluoroethane (HFC), dimethyl-β-cyclodextrin, cyclodextrin-type compounds such as Captisol®, dimethyl ether, dimethyl phthalate, dipotassium edetate, disodium edetate, disodium hydrogen phosphate, docusate calcium, docusate potassium, docusate sodium, dodecyl gallate, dodecyltrimethylammonium bromide, edentate calcium disodium, edtic acid, eglumine, ethyl alcohol, ethylcellulose, ethyl gallate, ethyl laurate, ethyl maltol, ethyl oleate, ethylparaben, ethylparaben potassium, ethylparaben sodium, ethyl vanillin, fructose, fructose liquid, fructose milled, fructose pyrogen-free, powdered fructose, fumaric acid, gelatin, glucose, liquid glucose, glyceride mixtures of saturated vegetable fatty acids, glycerin, glyceryl behenate, glyceryl monooleate, glyceryl monostearate, self-emulsifying glyceryl monostearate, glyceryl palmitostearate, glycine, glycols, glycofurol, guar gum, heptafluoropropane (HFC), hexadecyltrimethylammonium bromide, high fructose syrup, human serum albumin, hydrocarbons (HC), dilute hydrochloric acid, hydrogenated vegetable oil, type II, hydroxyethyl cellulose, 2-hydroxyethyl-β-cyclodextrin, hydroxypropyl cellulose, low-substituted hydroxypropyl cellulose, 2-hydroxypropyl-β-cyclodextrin, hydroxypropyl methylcellulose, hydroxypropyl methylcellulose phthalate, imidurea, indigo carmine, ion exchangers, iron oxides, isopropyl alcohol, isopropyl myristate, isopropyl palmitate, isotonic saline, kaolin, lactic acid, lactitol, lactose, lanolin, lanolin alcohols, anhydrous lanolin, lecithin, magnesium aluminum silicate, magnesium carbonate, normal magnesium carbonate, magnesium carbonate anhydrous, magnesium carbonate hydroxide, magnesium hydroxide, magnesium lauryl sulfate, magnesium oxide, magnesium silicate, magnesium stearate, magnesium trisilicate, magnesium trisilicate anhydrous, malic acid, malt, maltitol, maltitol solution, maltodextrin, maltol, maltose, mannitol, medium chain triglycerides, meglumine, menthol, methylcellulose, methyl methacrylate, methyl oleate, methylparaben, methylparaben potassium, methylparaben sodium, microcrystalline cellulose and carboxymethylcellulose sodium, mineral oil, light mineral oil, mineral oil and lanolin alcohols, oil, olive oil, monoethanolamine, montmorillonite, octyl gallate, oleic acid, palmitic acid, paraffin, peanut oil, petrolatum, petrolatum and lanolin alcohols, pharmaceutical glaze, phenol, liquified phenol, phenoxyethanol, phenoxypropanol, phenylethyl alcohol, phenylmercuric acetate, phenylmercuric borate, phenylmercuric nitrate, polacrilin, polacrilin potassium, poloxamer, polydextrose, polyethylene glycol, polyethylene oxide, polyacrylates, polyethylene-polyoxypropylene-block polymers, polymethacrylates, polyoxyethylene alkyl ethers, polyoxyethylene castor oil derivatives, polyoxyethylene sorbitol fatty acid esters, polyoxyethylene stearates, polyvinyl alcohol, polyvinyl pyrrolidone, potassium alginate, potassium benzoate, potassium bicarbonate, potassium bisulfite, potassium chloride, potassium citrate, potassium citrate anhydrous, potassium hydrogen phosphate, potassium metabisulfite, monobasic potassium phosphate, potassium propionate, potassium sorbate, povidone, propanol, propionic acid, propylene carbonate, propylene glycol, propylene glycol alginate, propyl gallate, propylparaben, propylparaben potassium, propylparaben sodium, protamine sulfate, rapeseed oil, Ringer's solution, saccharin, saccharin ammonium, saccharin calcium, saccharin sodium, safflower oil, saponite, serum proteins, sesame oil, colloidal silica, colloidal silicon dioxide, sodium alginate, sodium ascorbate, sodium benzoate, sodium bicarbonate, sodium bisulfite, sodium chloride, anhydrous sodium citrate, sodium citrate dehydrate, sodium chloride, sodium cyclamate, sodium edentate, sodium dodecyl sulfate, sodium lauryl sulfate, sodium metabisulfite, sodium phosphate, dibasic, sodium phosphate, monobasic, sodium phosphate, tribasic, anhydrous sodium propionate, sodium propionate, sodium sorbate, sodium starch glycolate, sodium stearyl fumarate, sodium sulfite, sorbic acid, sorbitan esters (sorbitan fatty esters), sorbitol, sorbitol solution 70%, soybean oil, spermaceti wax, starch, corn starch, potato starch, pregelatinized starch, sterilizable maize starch, stearic acid, purified stearic acid, stearyl alcohol, sucrose, sugars, compressible sugar, confectioner's sugar, sugar spheres, invert sugar, Sugartab, Sunset Yellow FCF, synthetic paraffin, talc, tartaric acid, tartrazine, tetrafluoroethane (HFC), theobroma oil, thimerosal, titanium dioxide, alpha tocopherol, tocopheryl acetate, alpha tocopheryl acid succinate, beta-tocopherol, delta-tocopherol, gamma-tocopherol, tragacanth, triacetin, tributyl citrate, triethanolamine, triethyl citrate, trimethyl-β-cyclodextrin, trimethyltetradecylammonium bromide, tris buffer, trisodium edentate, vanillin, type I hydrogenated vegetable oil, water, soft water, hard water, carbon dioxide-free water, pyrogen-free water, water for injection, sterile water for inhalation, sterile water for injection, sterile water for irrigation, waxes, anionic emulsifying wax, carnauba wax, cationic emulsifying wax, cetyl ester wax, microcrystalline wax, nonionic emulsifying wax, suppository wax, white wax, yellow wax, white petrolatum, wool fat, xanthan gum, xylitol, zein, zinc propionate, zinc salts, zinc stearate, or any excipient in the *Handbook of Pharmaceutical Excipients,* Third Edition, A. H. Kibbe (Pharmaceutical Press, London, UK, 2000), which is incorporated by reference in its entirety. *Remington's Pharmaceutical Sciences,* Sixteenth Edition, E. W. Martin (Mack Publishing Co., Easton, Pa., 1980), which is incorporated by reference in its entirety, discloses various components used in formulating pharmaceutically acceptable compositions and known techniques for the preparation thereof. Except insofar as any conventional agent is incompatible with the pharmaceutical compositions, its use in pharmaceutical compositions is contemplated. Supplementary active ingredients also can be incorporated into the compositions.

In some embodiments, the foregoing component(s) may be present in the pharmaceutical composition at any concentration, such as, for example, at least A, wherein A is 0.0001% w/v, 0.001% w/v, 0.01% w/v, 0.1% w/v, 1% w/v, 2% w/v, 5% w/v, 10% w/v, 20% w/v, 30% w/v, 40% w/v, 50% w/v, 60% w/v, 70% w/v, 80% w/v, or 90% w/v. In some embodiments, the foregoing component(s) may be present in the pharmaceutical composition at any concentration, such as, for example, at most B, wherein B is 90% w/v, 80% w/v, 70% w/v, 60% w/v, 50% w/v, 40% w/v, 30% w/v, 20% w/v, 10% w/v, 5% w/v, 2% w/v, 1% w/v, 0.1% w/v, 0.001% w/v, or 0.0001%. In other embodiments, the foregoing component(s) may be present in the pharmaceutical composition at any concentration range, such as, for example from about A to about B. In some embodiments, A is 0.0001% and B is 90%.

The pharmaceutical compositions may be formulated to achieve a physiologically compatible pH. In some embodiments, the pH of the pharmaceutical composition may be at least 5, at least 5.5, at least 6, at least 6.5, at least 7, at least 7.5, at least 8, at least 8.5, at least 9, at least 9.5, at least 10, or at least 10.5 up to and including pH 11, depending on the formulation and route of administration. In certain embodiments, the pharmaceutical compositions may comprise buffering agents to achieve a physiological compatible pH. The buffering agents may include any compounds capable of buffering at the desired pH such as, for example, phosphate buffers (e.g. PBS), triethanolamine, Tris, bicine, TAPS, tricine, HEPES, TES, MOPS, PIPES, cacodylate, MES, and others. In certain embodiments, the strength of the buffer is at least 0.5 mM, at least 1 mM, at least 5 mM, at least 10 mM, at least 20 mM, at least 30 mM, at least 40 mM, at least 50 mM, at least 60 mM, at least 70 mM, at least 80 mM, at least 90 mM, at least 100 mM, at least 120 mM, at least 150 mM, or at least 200 mM. In some embodiments, the strength of the buffer is no more than 300 mM (e.g. at most 200 mM, at most 100 mM, at most 90 mM, at most 80 mM, at most 70 mM, at most 60 mM, at most 50 mM, at most 40 mM, at most 30 mM, at most 20 mM, at most 10 mM, at most 5 mM, at most 1 mM).

Routes of Administration

The following discussion on routes of administration is merely provided to illustrate exemplary embodiments and should not be construed as limiting the scope in any way.

Formulations suitable for oral administration can consist of (a) liquid solutions, such as an effective amount of the analog of the present disclosure dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the analog of the present disclosure in a flavor, usually sucrose and acacia or tragacanth, as well as pastilles comprising the analog of the present disclosure in an inert base, such as gelatin and glycerin, or sucrose and acacia, emulsions, gels, and the like containing, in addition to, such excipients as are known in the art.

The PTH peptides, PTHrP peptides (or related analogs or variants or chemical derivatives, fusion polypeptides, multimeric polypeptides, peptidomimetics, peptoids, retroinverso peptides) of the disclosure, alone or in combination with other suitable components, can be delivered via pulmonary administration and can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for nonpressured preparations, such as in a nebulizer or an atomizer. Such spray formulations also may be used to spray mucosa. In some embodiments, the PTH peptides, PTHrP peptides (or related analogs or variants or chemical derivatives, fusion polypeptides, multimeric polypeptides, peptidomimetics, peptoids, retroinverso peptides) are formulated into a powder blend or into microparticles or nanoparticles. Suitable pulmonary formulations are known in the art. See, e.g., Qian et al., Int J Pharm 366: 218-220 (2009); Adjei and Garren, Pharmaceutical Research, 7(6): 565-569 (1990); Kawashima et al., J Controlled Release 62(1-2): 279-287 (1999); Liu et al., Pharm Res 10(2): 228-232 (1993); International Patent Application Publication Nos. WO 2007/133747 and WO 2007/141411.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term, "parenteral" means not through the alimentary canal but by some other route such as subcutaneous, intramuscular, intraspinal, or intravenous. The PTH peptides, PTHrP peptides (or related analogs or variants or chemical derivatives, fusion polypeptides, multimeric polypeptides, peptidomimetics, peptoids, retroinverso peptides) of the present disclosure can be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-153-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the PTH peptides, PTHrP peptides (or related analogs or variants or chemical derivatives, fusion polypeptides, multimeric polypeptides, peptidomimetics, peptoids, retroinverso peptides) of the present disclosure in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Additionally, the PTH peptides, PTHrP peptides (or related analogs or variants or chemical derivatives, fusion polypeptides, multimeric polypeptides, peptidomimetics, peptoids, retroinverso peptides) of the present disclosures can be made into suppositories for rectal administration by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that, in addition to the above-described pharmaceutical compositions, the PTH peptides, PTHrP peptides (or related analogs or variants or chemical derivatives, fusion polypeptides, multimeric polypeptides, peptidomimetics, peptoids, retroinverso peptides) of the disclosure can be formulated as inclusion complexes, such as cyclodextrin inclusion complexes, or liposomes.

Dose

Pharmaceutical compositions within the scope of this invention include all compositions wherein the peptide or polypeptide analog is contained in an amount effective to achieve its intended purpose. While individual needs vary, determination of optimal ranges of effective amounts of each component is within the skill of the art. Typical dosages comprise 0.1 to 100 mg/kg/body weight.

For purposes of the disclosure, the amount or dose of the PTH peptides, PTHrP peptides (or related analogs or variants or chemical derivatives, fusion polypeptides, multimeric polypeptides, peptidomimetics, peptoids, retroinverso peptides) of the present disclosure administered should be sufficient to effect, e.g., a therapeutic or prophylactic response, in the subject or animal over a reasonable time frame. For example, the dose of the PTH peptides, PTHrP peptides (or related analogs or variants or chemical derivatives, fusion polypeptides, multimeric polypeptides, peptidomimetics, peptoids, retroinverso peptides) of the present disclosure should be sufficient to stimulate cAMP secretion from cells or accumulation in cells as described herein or sufficient to activate a PTH receptor in a cell, treat a subject having a disease or condition associated with bone loss, ameliorate a symptom associated with osteoporosis, retard the progression of osteoporosis, or regenerate bone, in a period of from about 1 to 4 minutes, 1 to 4 hours or 1 to 4 weeks or longer, e.g., 5 to 20 or more weeks, from the time of administration. In certain embodiments, the time period could be even longer. The dose will be determined by the efficacy of the particular PTH peptides, PTHrP peptides (or related analogs or variants or chemical derivatives, fusion polypeptides, multimeric polypeptides, peptidomimetics, peptoids, retroinverso peptides) of the present disclosure and the condition of the animal (e.g., human), as well as the body weight of the animal (e.g., human) to be treated.

Many assays for determining an administered dose are known in the art. For purposes herein, an assay, which comprises comparing the extent to which cAMP is stimulated by cells upon administration of a given dose of the PTH peptides, PTHrP peptides (or related analogs or variants or chemical derivatives, fusion polypeptides, multimeric polypeptides, peptidomimetics, peptoids, retroinverso peptides) of the present disclosure to a mammal among a set of mammals of which is each given a different dose of the PTH peptides, PTHrP peptides (or related analogs or variants or chemical derivatives, fusion polypeptides, multimeric polypeptides, peptidomimetics, peptoids, retroinverso peptides), could be used to determine a starting dose to be administered to a mammal. Methods of testing the extent to which cAMP production is stimulated are known in the art and include the method described herein in Example 1.

The dose of the PTH peptides, PTHrP peptides (or related analogs or variants or chemical derivatives, fusion polypeptides, multimeric polypeptides, peptidomimetics, peptoids, retroinverso peptides) of the present disclosure also will be determined by the existence, nature and extent of any adverse side effects that might accompany the administration of a particular analog of the present disclosure. Typically, the attending physician will decide the dosage of the PTH peptides, PTHrP peptides (or related analogs or variants or chemical derivatives, fusion polypeptides, multimeric polypeptides, peptidomimetics, peptoids, retroinverso peptides) of the present disclosure with which to treat each individual patient, taking into consideration a variety of factors, such as age, body weight, general health, diet, sex, PTH peptides, PTHrP peptides (or related analogs or variants or chemical derivatives, fusion polypeptides, multimeric polypeptides, peptidomimetics, peptoids, retroinverso peptides) of the present disclosure to be administered, route of administration, and the severity of the condition being treated. By way of example and not intending to limit the invention, the dose of the PTH peptides, PTHrP peptides (or related analogs or variants or chemical derivatives, fusion polypeptides, multimeric polypeptides, peptidomimetics, peptoids, retroinverso peptides) of the present disclosure can be about 0.0001 to about 1 g/kg body weight of the subject being treated/day, from about 0.0001 to about 0.001 g/kg body weight/day, or about 0.01 mg to about 1 g/kg body weight/day.

Targeted Forms

One of ordinary skill in the art will readily appreciate that the PTH peptides, PTHrP peptides (or related analogs or variants or chemical derivatives, fusion polypeptides, multimeric polypeptides, peptidomimetics, peptoids, retroinverso peptides) of the disclosure can be modified in any number of ways, such that the therapeutic or prophylactic efficacy of the PTH peptides, PTHrP peptides (or related analogs or variants or chemical derivatives, fusion polypeptides, multimeric polypeptides, peptidomimetics, peptoids, retroinverso peptides) of the present disclosures is increased through the modification. For instance, the PTH peptides, PTHrP peptides (or related analogs or variants or chemical derivatives, fusion polypeptides, multimeric polypeptides, peptidomimetics, peptoids, retroinverso peptides) of the present disclosure can be conjugated either directly or indirectly through a linker to a targeting moiety. The practice of conjugating compounds, e.g., PTH peptides, PTHrP peptides (or related analogs or variants or chemical derivatives, fusion polypeptides, multimeric polypeptides, peptidomimetics, peptoids, retroinverso peptides) described herein, to targeting moieties is known in the art. See, for instance, Wadhwa et al., *J Drug Targeting*, 3, 111-127 (1995) and U.S. Pat. No. 5,087,616. The term "targeting moiety" as used herein, refers to any molecule or agent that specifically recognizes and binds to a cell-surface receptor, such that the targeting moiety directs the delivery of the PTH peptides, PTHrP peptides (or related analogs or variants or chemical derivatives, fusion polypeptides, multimeric polypeptides, peptidomimetics, peptoids, retroinverso peptides) of the present disclosures to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups. The term "linker" in some embodiments refers to any agent or molecule that bridges the PTH peptides, PTHrP peptides (or related analogs or variants or chemical derivatives, fusion polypeptides, multimeric polypeptides, peptidomimetics, peptoids, retroinverso peptides) of the present disclosures to the targeting moiety. One of ordinary skill in the art recognizes that sites on the PTH peptides, PTHrP peptides (or related analogs or variants or chemical derivatives, fusion polypeptides, multimeric polypeptides, peptidomimetics, peptoids, retroinverso peptides) of the present disclosures, which are not necessary for the function of the analog of the present disclosures, are ideal sites for attaching a linker and/or a targeting moiety, provided that the linker and/or targeting moiety, once attached to the PTH peptides, PTHrP peptides (or related analogs or variants or chemical derivatives, fusion polypeptides, multimeric polypeptides, peptidomimetics, peptoids, retroinverso peptides) of the present disclosures, do(es) not interfere with the function of the PTH peptides, PTHrP peptides (or related analogs or variants or chemical derivatives, fusion polypeptides, multimeric polypeptides, peptidomimetics, peptoids, retroinverso peptides) of the present disclosures, i.e., the ability to stimulate cAMP secretion from cells, to treat osteoporosis or cancer.

Controlled Release Formulations

Alternatively, the PTH peptides, PTHrP peptides (or related analogs or variants or chemical derivatives, fusion polypeptides, multimeric polypeptides, peptidomimetics, peptoids, retroinverso peptides) described herein can be modified into a depot form, such that the manner in which the PTH peptides, PTHrP peptides (or related analogs or variants or chemical derivatives, fusion polypeptides, multimeric polypeptides, peptidomimetics, peptoids, retroinverso peptides) of the present disclosures is released into the body to which it is administered is controlled with respect to time and location within the body (see, for example, U.S. Pat. No. 4,450,150). Depot forms of PTH peptides, PTHrP peptides (or related analogs or variants or chemical derivatives, fusion polypeptides, multimeric polypeptides, peptidomimetics, peptoids, retroinverso peptides) of the present disclosures can be, for example, an implantable composition comprising the PTH peptides, PTHrP peptides (or related analogs or variants or chemical derivatives, fusion polypeptides, multimeric polypeptides, peptidomimetics, peptoids, retroinverso peptides) of the present disclosures and a porous or non-porous material, such as a polymer, wherein the PTH peptides, PTHrP peptides (or related analogs or variants or chemical derivatives, fusion polypeptides, multimeric polypeptides, peptidomimetics, peptoids, retroinverso peptides) of the present disclosures is encapsulated by or diffused throughout the material and/or degradation of the non-porous material. The depot is then implanted into the desired location within the body and the PTH peptides, PTHrP peptides (or related analogs or variants or chemical derivatives, fusion polypeptides, multimeric polypeptides, peptidomimetics, peptoids, retroinverso peptides) of the present disclosures are released from the implant at a predetermined rate.

The pharmaceutical composition in certain aspects is modified to have any type of in vivo release profile. In some aspects, the pharmaceutical composition is an immediate release, controlled release, sustained release, extended release, delayed release, or bi-phasic release formulation. Methods of formulating peptides for controlled release are known in the art. See, for example, Qian et al., *J Pharm* 374: 46-52 (2009) and International Patent Application Publication Nos. WO 2008/130158, WO2004/033036; WO2000/032218; and WO 1999/040942.

The instant compositions may further comprise, for example, micelles or liposomes, or some other encapsulated form, or may be administered in an extended release form to provide a prolonged storage and/or delivery effect. The disclosed pharmaceutical formulations may be administered according to any regime including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi-monthly.

Combinations

The PTH peptides, PTHrP peptides (or related analogs or variants or chemical derivatives, fusion polypeptides, multimeric polypeptides, peptidomimetics, peptoids, retroinverso peptides) of the present disclosures can be used in combination with another active ingredient. For example, the PTH peptides, PTHrP peptides (or related analogs or variants or chemical derivatives, fusion polypeptides, multimeric polypeptides, peptidomimetics, peptoids, retroinverso peptides) disclosed herein may be formulated with another anti-osteoporosis agent, including any of the following: bisphosphonates, such as alendronate (Fosamax), ibandronate (Boniva), risedronate (Actonel), and zoledronic acid (Reclast), which slow the rate of bone thinning and can lead to increased bone density; Raloxifene (Evista), a selective estrogen receptor modulator (SERM) which slows bone thinning and causes some increase in bone thickness; Calcitonin (Calcimar or Miacalcin), a naturally occurring hormone that helps regulate calcium levels in the body and is part of the bone-building process; Parathyroid hormone (teriparatide [Forteo]), administered by injection; estrogen (e.g., with or without progestin); testosterone (shots, gels, patches);

In some embodiments, the PTH peptides, PTHrP peptides (or related analogs or variants or chemical derivatives, fusion polypeptides, multimeric polypeptides, peptidomimetics, peptoids, retroinverso peptides) of the present disclosures is formulated in combination with an anti-cancer agent. Suitable anti-cancer agents are known in the art and include any of the following chemotherapeutics: platinum coordination compounds, topoisomerase inhibitors, antibiotics, antimitotic alkaloids and difluoronucleosides.

In some embodiments, the platinum coordination compound is cis-diamminediaquoplatinum(II)-ion; chloro(diethylenetriamine)-platinum(II)chloride; dichloro(ethylenediamine)-platinum(II), diammine(1,1-cyclobutanedicarboxylato)platinum(II) (carboplatin); spiroplatin; iproplatin; diammine(2-ethylmalonato)-platinum(II); ethylenediaminemalonatoplatinum(II); aqua(1,2-diaminodyclohexane)-sulfatoplatinum(II); (1,2-diaminocyclohexane)malonatoplatinum(II); (4-caroxyphthalato)(1,2-diaminocyclohexane)platinum(II); (1,2-diaminocyclohexane)-(isocitrato)platinum(II); (1,2-diaminocyclohexane)cis(pyruvato)platinum(II); (1,2-diaminocyclohexane)oxalatoplatinum(II); ormaplatin; and tetraplatin.

In some embodiments, cisplatin is the platinum coordination compound employed in the compositions and methods of the present invention. Cisplatin is commercially available under the name PLATINOL™ from Bristol Myers-Squibb Corporation and is available as a powder for constitution with water, sterile saline or other suitable vehicle. Other platinum coordination compounds suitable for use in the present invention are known and are available commercially and/or can be prepared by conventional techniques. Cisplatin, or cis-dichlorodiammineplatinum II, has been used successfully for many years as a chemotherapeutic agent in the treatment of various human solid malignant tumors. More recently, other diamino-platinum complexes have also shown efficacy as chemotherapeutic agents in the treatment of various human solid malignant tumors. Such diamino-platinum complexes include, but are not limited to, spiroplatinum and carboplatinum. Although cisplatin and other diamino-platinum complexes have been widely used as chemotherapeutic agents in humans, they have had to be delivered at high dosage levels that can lead to toxicity problems such as kidney damage.

In some embodiments, the chemotherapeutic agent is a topoisomerase inhibitor. Topoisomerases are enzymes that are capable of altering DNA topology in eukaryotic cells. They are critical for cellular functions and cell proliferation. Generally, there are two classes of topoisomerases in eukaryotic cells, type I and type II. Topoisomerase I is a monomeric enzyme of approximately 100,000 molecular weight. The enzyme binds to DNA and introduces a transient single-strand break, unwinds the double helix (or allows it to unwind), and subsequently reseals the break before dissociating from the DNA strand. Various topoisomerase inhibitors have recently shown clinical efficacy in the treatment of humans afflicted with ovarian, cancer, esophageal cancer or non-small cell lung carcinoma.

In some aspects, the topoisomerase inhibitor is camptothecin or a camptothecin analog. Camptothecin is a water-insoluble, cytotoxic alkaloid produced by Camptotheca accuminata trees indigenous to China and Nothapodytes foetida trees indigenous to India. Camptothecin exhibits tumor cell growth inhibiting activity against a number of tumor cells. Compounds of the camptothecin analog class are typically specific inhibitors of DNA topoisomerase I. By the term "inhibitor of topoisomerase" is meant any tumor cell growth inhibiting compound that is structurally related to camptothecin. Compounds of the camptothecin analog class include, but are not limited to; topotecan, irinotecan and 9-amino-camptothecin.

Uses

Without being bound to any particular theory, it is contemplated that the PTH peptides and PTHrP peptides described herein exhibit altered properties, as discussed herein for the first time, which altered properties confer increased therapeutic potential. In this regard, the invention provides methods of treating a disease or condition associated with undesired bone loss. The method comprises administering to a subject in need thereof a pharmaceutical composition as described herein in an amount effective to treat the subject.

The invention further provides a method of treating cancer in a subject, comprising administering to a subject in need thereof a pharmaceutical composition as described herein in an amount effective to treat the subject.

By the term "treating" is intended the administering to subjects of a pharmaceutical composition comprising a PTH or PTHrP peptide or polypeptide analog (variant or chemical derivative). The term "treating" as used herein, does not necessarily imply 100% or complete treatment. Rather, there are varying degrees of treatment of which one of ordinary skill in the art recognizes as having a potential benefit or therapeutic effect. In this respect, the inventive methods can provide any amount of any level of treatment of osteoporosis or cancer in a mammal. Furthermore, the treatment provided by the inventive method can include treatment of one or more conditions or symptoms of the disease or condition, e.g., osteoporosis or cancer, being treated, and/or can include the retarding of the progression of the disease or condition. For example, treating osteoporosis includes ameliorating a symptom associated with osteoporosis, retarding the progression of osteoporosis, and regenerating bone. Treating includes administering the agent to subjects at risk for developing osteoporosis or cancer prior to evidence of clinical disease, as well as subjects diagnosed with osteoporosis or cancer who have not yet been treated or who have been treated by other means. Thus, this invention is useful in preventing or inhibiting osteoporosis or cancer.

Accordingly, the invention further provides methods of ameliorating a symptom associated with osteoporosis. The symptom of osteoporosis in some embodiments is pain, backache, fractures of the spine, wrist, or hip, and height loss. The method comprises administering to a subject in need thereof a pharmaceutical composition as described herein in an amount effective to ameliorate a symptom associated with osteoporosis the subject.

The invention further provides methods of retarding the progression of osteoporosis. The method comprises administering to a subject in need thereof a pharmaceutical composition as described herein in an amount effective to retard the progression of osteoporosis. Progression (or regression) of osteoporosis may be monitored by methods known in the art, including, for example, dual X-ray absorptiometry (DXA or DEXA), ultrasound, and quantitative computed tomography (QCT).

The invention also provides methods of regenerating bone. The method comprises administering to a subject in need thereof a pharmaceutical composition as described herein in an amount effective to regenerate bone. Bone regeneration may be monitored by methods known herein, including, for example, measuring bone mineral density of the subject.

An effective amount or dose of a PTH or PTHrP peptide or polypeptide analog for treating bone loss, e.g., osteoporosis, or cancer is in the range of about 0.1 to 100 mg/kg/body weight. Effective doses may be determined, preferably by injecting cells, in vitro, or live animals, in vivo, in order to identify the optimal dose range using various of the methods described herein. The dosage administered will in part be dependent upon the health and weight of the recipient, the existence of other concurrent treatment, if any, frequency of treatment, and the nature of the effect desired.

The phrase "effective amount" or "amount effective" is used herein to mean an amount sufficient to treat or prevent, and preferably reduce by at least about 25 percent, more preferably by at least 50 percent, most preferably by at least 90 percent, a clinically significant change in a feature of pathology such as for example, elevated blood pressure, fever, or white cell count, as may attend its presence and activity As related to the present invention, the term may also mean an amount sufficient to ameliorate or reverse bone loss or cancer.

In some embodiments, the disease or condition associated with undesired bone loss is osteopenia or osteoporosis.

For purposes herein, the cancer can be any cancer. As used herein, the term "cancer" is meant any malignant growth or tumor caused by abnormal and uncontrolled cell division that may spread to other parts of the body through the lymphatic system or the blood stream. The cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor. Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

Subjects

As used herein the term "subject" refers to any multicellular living organism. In some embodiments, the subject is a mammal. The mammal can be any mammal including, but not limited to, mammals of the order Rodentia, such as mice and hamsters, and mammals of the order Logomorpha, such as rabbits. In some embodiments, the mammals are from the order Carnivora, including Felines (cats) and Canines (dogs). In some embodiments, the mammals are from the order Artiodactyla, including Bovines (cows) and Swines (pigs) or of the order Perssodactyla, including Equines (horses). In some embodiments, the mammals are of the order Primates, Ceboids, or Simoids (monkeys) or of the order Anthropoids (humans and apes). The preferred animal subject of the present invention is a mammal. The invention is particularly useful in the treatment of human subjects.

In addition to the above treatment methods, the PTH peptides and PTHrP peptides (as well as the variants, analogs, chemical derivatives, fusion polypeptides, or multimeric polypeptides, peptidomimetics, peptoids, retroinverso peptides) can be used to activate a PTH receptor in a cell. The method comprises administering to the cell a PTH peptide or PTHrP peptide (or variants, analogs, chemical derivatives, fusion polypeptides, or multimeric polypeptides, peptidomimetics, peptoids, retroinverso peptides thereof) such that the PTH receptor is activated.

In some embodiments, such methods are performed in vitro or ex vivo. The methods, in this regard, may be used to monitor the responsiveness of cells or tissues of a subject (e.g., a human) to the PTH peptides and PTHrP peptides (as well as the variants, analogs, chemical derivatives, fusion polypeptides, or multimeric polypeptides, peptidomimetics, peptoids, retroinverso peptides). In some embodiments, the methods are carried out for basic research purposes or clinical research purposes.

In some embodiments, such methods are performed in vivo, such that the cells is in a live animal and the PTH peptides and PTHrP peptides (as well as the variants, analogs, chemical derivatives, fusion polypeptides, or multimeric polypeptides, peptidomimetics, peptoids, retroinverso peptides) is administered to the live animal, e.g., human.

In some instances, the cell is an osteoblast. When the osteoblast is in a live animal, the method may be a therapeutic method. In embodiments in which the osteoblast is not in a live animal, the method may be performed for basic research or clinical research purposes.

In some embodiments, the cell is in a live animal and the cell is a lymphocyte or a white blood cell. Antibodies specific for the PTH peptides and PTHrP peptides (as well as the variants, analogs, chemical derivatives, fusion polypeptides, or multimeric polypeptides, peptidomimetics, peptoids, retroinverso peptides) may be produced by the live animal in this manner. Antibodies to the PTH peptides and PTHrP peptides (as well as the variants, analogs, chemical derivatives, fusion polypeptides, or multimeric polypeptides, peptidomimetics, peptoids, retroinverso peptides) are contemplated herein.

Kits

The invention further provides kits comprising any of the PTH peptides, PTHrP peptides, variants, analogs, chemical derivatives, fusion polypeptides, or multimeric polypeptides described herein and instructions for use. In some embodiments, the kit comprises instructions for administration of the PTH peptides, PTHrP peptides, variants, analogs, chemical derivatives, fusion polypeptides, or multimeric polypeptides to a subject, e.g., a human. In some embodiments, the instructions comprise instructions for administration to a subject having osteoporosis or cancer. In some embodiments, the kit comprises a device for administering the PTH peptides, PTHrP peptides, variants, analogs, chemical derivatives, fusion polypeptides, or multimeric polypeptides to a subject, e.g. syringe needle, pen device, jet injector or other needle-free injector. The kit may alternatively or in addition include one or more containers, e.g., vials, tubes, bottles, single or multi-chambered pre-filled syringes, cartridges, infusion pumps (external or implantable), jet injectors, pre-filled pen devices and the like, optionally pre-packaged with the PTH peptides, PTHrP peptides, variants, analogs, chemical derivatives, fusion polypeptides, multimeric polypeptides in a lyophilized form or in an aqueous solution.

Having now generally described the invention, the same will be more readily understood through reference to the following examples, which are provided by way of illustration, and are not intended to be limiting of the present invention, unless specified.

EXAMPLES

Example 1

Materials and Methods for Examples 2-5

Protein purification and peptide synthesis. The MBP-PTH1R ECD-(His)6 fusion protein containing residues 29-187 of PTH1R fused to the C-terminus of MBP was previously described (27). Isolated PTH1R ECD (residues 23-191) free of MBP and biotinylated at a single site in an N-terminal biotinylation tag was prepared as described in supplemental methods. Peptides for ECD-binding studies and crystallization were custom synthesized and HPLC-purified by SynBioSci (Livermore, Calif.). PTH/PTHrP(1-34) NH2 hybrid peptides were synthesized and HPLC-purified by the Massachusetts General Hospital Biopolymer Core facility. All peptides were C-terminally amidated unless indicated otherwise.

ECD-peptide binding assays. The binding of peptides to the MBP-PTH1R ECD-H6 fusion protein was assessed using an AlphaScreen assay (Perkin-Elmer). The reaction mixtures were incubated at room temperature and contained 5 µg/ml each of streptavidin-coated donor beads and nickel-chelate-coated acceptor beads, and 23 nM each of N-terminally biotinylated PTH(7-34)NH2 and MBP-PTH1R ECD-H6 in a buffer of 50 mM MOPS pH 7.4, 150 mM NaCl, and 7 mg/ml BSA. The biotinylated PTH and MBP-PTH1R ECD-H6 were separately pre-coupled for 1 hr to the streptavidin and nickel-chelate beads, respectively. The pre-coupling reactions were mixed, un-labeled competitor peptides were added as indicated, and the reactions were incubated 4 to 5 hrs to reach equilibrium. Photon counts were recorded in 384-well optiplates using an Envision 2104 plate reader (Perkin-Elmer). Prism 5.0 software (GraphPad Software, San Diego) was used to fit the data to a fixed-slope dose-response inhibition equation for determination of IC50 values. Real-time analysis of the binding of peptides to the isolated PTH1R ECD using the Octet Red system (ForteBio) was performed as described in below.

Crystallization, data collection, structure solution, and refinement. MBP-PTH1R ECD-H6 in 10 mM Tris-HCl, pH 7.5, 50 mM NaCl, 1 mM Maltose, and 1 mM EDTA was mixed with a synthetic PTHrP fragment (residues 12-34) at a 1:1.1 molar ratio (protein:peptide), incubated on ice for 30 min, and spin concentrated to 20 mg/ml for crystallization. Bipyramidal crystals were grown by the sitting drop vapor diffusion method at 20° C. with a reservoir solution of 7.5% PEG 2000, 13% PEG 400. The crystals were transferred into a cryoprotectant solution of 10% PEG 2000, 22% PEG 400, 50 mM NaCl, 1 mM EDTA by dialysis overnight and flash frozen by plunging into liquid nitrogen. A data set was collected from a single crystal at LS-CAT beamline 21-ID-F of the Advanced Photon Source (Argonne, Ill.) at a wavelength of 0.9785 Å and temperature of 100° K. The HKL2000 package (37) was used to process the data and the Scalepack intensities were converted to structure factor amplitudes with the CCP4 suite (38). The structure was solved by molecular replacement with Phaser (39) using separate search models for MBP and the PTH1R ECD from PDB coordinate file 3C4M (27). There is one MBP-PTH1R ECD:PTHrP(12-34) complex in the asymmetric unit. Iterative cycles of rebuilding in O (40) and restrained refinement with Refmac5 (41) completed the structure. TLS refinement (42) was included using two TLS groups corresponding to the MBP-maltose complex and the ECD-PTHrP complex. Structure validation with Procheck (43) indicated that 93.6% of the residues were in the most favored region of the Ramachandran plot and no residues were in the disallowed region. The data collection and refinement statistics are listed in Table S1. Analyses of solvent accessible surface area and shape complementarity were performed within the CCP4 suite. Structure figures were prepared with PyMol (44).

Receptor binding assay. Peptide binding to the G protein-uncoupled receptor (R0) and G protein-coupled receptor (RG) conformations in cell membranes was assessed as previously described (26).

cAMP assays. COS-1 cells obtained from American Type Culture Collection (Manassas, Va.) were cultured in Dulbecco's modified Eagle's medium supplemented with 10% fetal bovine serum in a 37° C./5% CO2 incubator. 500,000 cells were seeded in a 10 cm dish and transfected the following morning by the DEAE-dextran method with 3 µg pcDNA3.1 vector encoding hPTH1R. Approximately 40,000 transfected cells were seeded in each well of a 96-well plate 24 hr post-transfection. 48 hrs post-transfection the cells were washed twice with PBS, pH 7.4 and stimulated with peptide. For dose-response assay, the cells were stimulated for 30 min. at 37° C. with peptide in Krebs-Ringers-Hepes (KRH) buffer (25 mM Hepes, pH 7.4, 104 mM NaCl, 5 mM KCl, 2 mM CaCl2, 1 mM KH2PO4, 1.2 mM MgSO4) supplemented with 0.2% BSA, 0.01% soybean trypsin inhibitor, 0.1% bacitracin, and 2 mM 3-isobutyl-1-methylxanthine (IBMX). The reactions were stopped with cold 6% perchloric acid and the cell lysates were neutralized with KHCO3. cAMP was measured with a LANCE cAMP kit (Perkin-Elmer) according to the manufacturer's instructions. For ligand wash-out assay, the cells were stimulated for 10 min at room temperature with peptide (100 nM) in KRH buffer supplemented as above, but lacking IBMX. The cells were rinsed three times with buffer lacking IBMX, and at the indicated times after ligand wash-out the buffer was replaced with buffer containing IBMX for 5 min before stopping the reactions and assessing cAMP content as above. Curve-fitting was performed with Prism 5.0 software using a fixed-slope dose-response stimulation equation for the dose-response assay and a single phase exponential decay equation for the ligand wash-out assay.

Expression plasmid construction. A DNA fragment encoding PTH1R residues 23 to 191 with a C-terminal six histidine residue tag was PCR amplified from pcDNA3.1/PTH1R. The fragment was digested with BamHI and NotI restriction endonucleases and ligated into a pETDuet1 vector (Novagen) encoding maltose binding protein (MBP) followed by a thrombin cleavage site (Th) and a biotinylation tag sequence (GGLNDIFEAQKIEWHEDT; biotinylation site in bold) in multiple cloning site 1 and the BirA biotin ligase in multiple cloning site 2. The resulting vector co-expresses the MBP-Th-Biotin tag-PTH1R ECD-H6 fusion protein and BirA. The construct was verified by automated DNA sequencing of the coding regions.

MBP-Th-Biotin tag-PTH1R ECD fusion protein expression and purification. *E. coli* Origami B (DE3) cells (Novagen) were transformed with the expression plasmid and grown in 12 L LB medium at 37° C. to mid-log phase. The temperature was reduced to 16° C., biotin was added to 5 µM final concentration, and protein expression was induced with 0.4 mM IPTG for a total induction time of ~19 hrs. The cells were harvested and resuspended in 50 mM Tris-HCl pH 7.5, 150 mM NaCl, 10% glycerol, and 25 mM imidazole. The cells were lysed by homogenization at 10,000 psi and the resulting lysate was clarified by centrifugation. The supernatant was loaded directly on a 50 ml Ni2+ Chelating Sepharose column (GE Healthcare). The column was washed with 600 ml 50 mM Tris-HCl pH 7.5, 150 mM NaCl, 10% glycerol, and 72.5 mM imidazole and the fusion protein was eluted in buffer with 262.5 mM imidazole. The peak fractions were pooled and loaded on a 50 ml Amylose high flow column (New England Biolabs) equilibrated in 50 mM Tris-HCl pH 7.5, 150 mM NaCl, and 5% glycerol. The protein was eluted with a linear gradient of 0-10 mM maltose. The peak fractions were pooled, diluted to 1 mg/ml, and the sample was treated for 23 hrs at 20° C. with 1 mM reduced glutathione, 1 mM oxidized glutathione, and a 1:1 molar ratio of purified DsbC to MBP-Th-Biotin tag-PTH1R ECD-H6 to allow for disulfide bond shuffling. DsbC was purified as previously described (45). The disulfide shuffling reaction mixture was run over a 50 ml Ni2+ chelating sepharose column as above to remove the DsbC. The eluted fusion protein was concentrated, loaded on a 300 ml Superdex200 column (GE Healthcare), and the peak corresponding to the correctly folded protein was collected. Native gel electrophoresis of the purified sample suggested that the protein was ~50% biotinylated as evidenced by two distinct bands of slightly different mobility (data not shown). The protein concentration was determined by the method of Bradford (46).

Octet Red real-time analysis of peptide binding to the biotinylated PTH1R ECD. The interaction between biotinylated PTH1R ECD and PTH(1-34)NH2 and PTHrP(1-34)NH2 was analyzed by bio-layer interferometry technology using the Octet Red system (ForteBio). MBP was removed from the MBP-Th-Biotin tag-PTH1R ECD fusion protein by overnight digestion at 4° C. with human α-thrombin (Haematologic Technologies Inc.) at a 1:750 ratio (weight:weight) of protease to fusion protein. Complete cleavage was verified by SDS-PAGE (data not shown). High binding streptavidin sensors were incubated with the digestion reaction diluted to 2 µg/ml protein in KRH buffer supplemented with 2 mg/ml BSA, followed by a 10 µg/ml biocytin block, and three washes in KRH buffer supplemented with 2 mg/ml BSA to wash away non-biotinylated components of the digestion mixture and establish a baseline. The peptides were diluted in KRH buffer with 2 mg/ml BSA and their association and dissociation were monitored for 20 min each at 25° C. To account for non-specific binding, traces obtained with peptide and sensor tips lacking PTH1R ECD were subtracted from the traces obtained with the peptides and immobilized PTH1R ECD. In addition, a baseline drift was subtracted using a trace from a sensor tip that had immobilized PTH1R ECD, but no peptide. Octet Red analysis software was used to analyze the data.

Example 2

PTH and PTHrP Binding to the PTH1R ECD

The binding of PTH and PTHrP to the MBP-PTH1R ECD-H6 fusion protein in vitro was assessed using an AlphaScreen luminescent proximity assay (Perkin-Elmer). In this assay, N-terminally biotinylated PTH(7-34)NH2 was bound to streptavidin-coated donor beads and the fusion protein was bound to Nickel-chelate coated acceptor beads via the (His)6 tag. Association of the biotinylated PTH and the fusion protein brings the beads into proximity generating a luminescent signal. The inventors previously showed that PTH(15-34)NH2 competed the interaction with an IC50 value that was similar to the Kd value of ~1 µM determined by isothermal titration calorimetry (27). PTH(1-34)NH2 and PTH(12-34)NH2 both competed the AlphaScreen interaction with an IC50 value of ~1 µM (FIG. 1A) in agreement with the inventor's previous observations. However, PTH(1-34)OH bound the fusion protein with approximately 10-fold lower affinity than the C-terminally amidated peptide (FIG. 1A). This result is consistent with the crystal structure of the PTH1R ECD in complex with PTH(15-34)NH2 which showed that the C-terminal amide group forms two hydrogen bonds to the ECD (27). In contrast, PTHrP(12-34)NH2 and PTHrP(12-34)OH competed the interaction with similar IC50 values of ~2 µM (FIG. 1B), indicating that the C-terminal amide group of PTHrP is not important for ECD binding.

The inventors also examined the interaction of the peptides with the isolated PTH1R ECD by employing the Octet Red system (ForteBio) which uses bio-layer interferometry technology to monitor binding events in real-time. Isolated PTH1R ECD (residues 23-191) free of MBP and biotinylated at a single residue in a biotinylation tag sequence at the N-terminus of the protein was prepared as described in the Example 1. The biotinylated ECD was immobilized on the surface of streptavidin sensor tips and the binding of PTH(1-34)NH2 and PTHrP(1-34)NH2 free in solution was assessed. Steady-state analysis of the real-time binding curves (FIG. S1) indicated that PTH and PTHrP bound the ECD with Kd values of 2.8 µM and 0.99 µM, respectively (FIGS. 1C and 1D). The Kd value for PTH is similar to that obtained by others using Biacore technology (31). The binding data taken together indicate that PTH and PTHrP bind the PTH1R ECD with similar affinities, but suggest differences in the underlying biochemical mechanisms because C-terminal amidation affects the ability of PTH, but not PTHrP, to bind the ECD.

Example 3

Structural Basis for PTHrP Binding to the PTH1R ECD

To understand the structural basis underlying the differences in the PTH and PTHrP binding mechanisms, the inventors determined the crystal structure of the MBP-PTH1R ECD-H6 fusion protein in complex with PTHrP(12-34)NH2. The structure was solved by molecular replacement and refined to an R factor of 19.3% (Free R factor 23.3%) at 1.94 Å resolution (Table 2).

TABLE 2

|  | MBP-PTH1R ECD: PTHrP(12-34)[a] |
|---|---|
| Data collection | |
| Space group | P4$_1$2$_1$2 |
| Cell dimensions | |
| a, b, c (Å) | 84.04, 84.04, 164.46 |
| α, β, γ (°) | 90.0, 90.0, 90.0 |
| Resolution (Å) | 50.00-1.94 (2.01-1.94)[b] |
| R$_{merge}$ | 0.091 (0.443) |
| I/σI | 29.66 (2.25) |
| Completeness (%) | 91.2 (55.0)[c] |
| Redundancy | 17.0 (8.5) |
| Refinement | |
| Resolution (Å) | 50.00-1.94 |
| No. reflections | 38628 |
| R$_{work}$/R$_{free}$ | 19.3/23.3 |
| No. atoms | |
| Protein | 3701 |
| Ligand/ion | 214 |
| Water | 237 |
| Mean B-factors | |
| MBP | 42.7 |
| PTH1R ECD | 59.9 |
| PTHrP | 67.2 |
| Maltose | 31.9 |
| Water | 47.1 |
| R.m.s. deviations | |
| Bond lengths (Å) | 0.012 |
| Bond angles (°) | 1.264 |

Figures 2A, 2B, 2C, 2D:
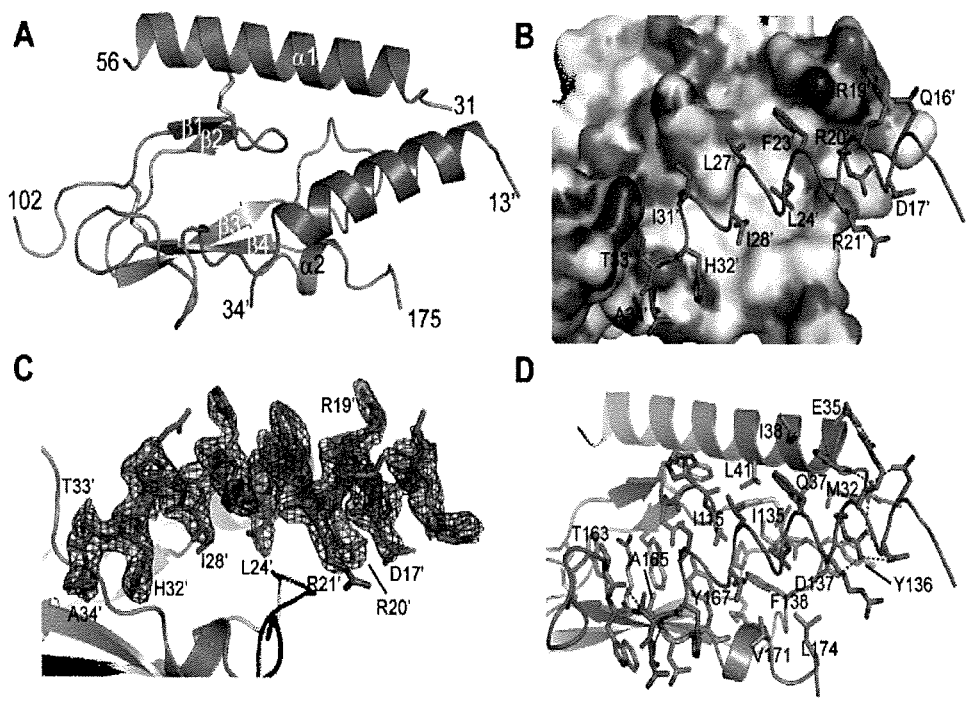
FIGS. 2A-2I show the structure of the PTH1R ECD in complex with PTHrP(12-34) and comparison to the PTH-bound PTH1R ECD.
Figures 2E, 2F, 2G, 2H, 2I:
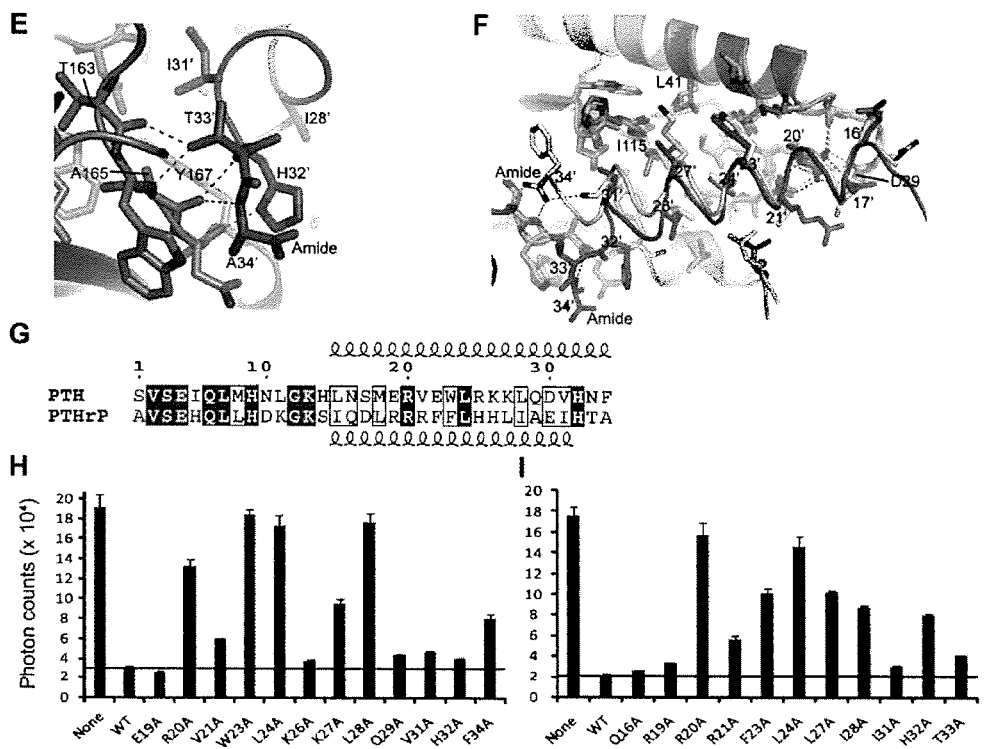

Electron density was observed for all PTH1R residues except 29-30, 57-101, 176-187, and the C-terminal (His)6 tag, which were excluded from the final model. The PTH1R ECD forms the conserved class B GPCR ECD fold previously observed (27), and PTHrP forms an amphipathic α-helix that binds to the hydrophobic groove of the ECD at the interface of the N-terminal α-helix, the two β-sheets, and the short, C-terminal α-helix (FIGS. 2A and 2B). Clear electron density was observed for PTHrP residues 13-34 (FIG. 2C). The interaction is mediated by hydrophobic interactions involving PTHrP residues F23', L24', L27', and I28', and an extensive network of hydrogen bonds (FIGS. 2B, 2D, and 2E). [Peptide residues are denoted with a prime to distinguish them from receptor residues.] R19' forms an intermolecular salt bridge with E35, but this may be caused by a crystal packing interaction that limits the mobility of R19' (not shown), as in the native protein R19' contacts the 7-TM domain of the receptor (32). The conserved R20' forms an intermolecular salt bridge with D137, an intermolecular hydrogen bond to the backbone carbonyl of M32, and intramolecular hydrogen bonds with the side chain of D17' that probably stabilize the helical conformation of the peptide (FIG. 2D). The PTHrP helix "unwinds" at the C-terminus after residue I31' permitting the formation of several additional intermolecular hydrogen bonds, including those between the δ nitrogen of H32' and the backbone amide nitrogen of Y167, between the side chain hydroxyl group of T33' and the backbone amide nitrogen of A165 and backbone carbonyl of T163, and between the backbone carbonyl of A165 and the backbone amide nitrogens of T33' and A34' (FIG. 2E). Consistent with our binding data in FIG. 1B, the C-terminal amide group of PTHrP does not form any interactions with the ECD.

Example 4

PTH and PTHrP Exhibit Different ECD-Binding Modes

Structural alignment of the PTHrP-ECD complex and the inventor's previously published PTH-ECD complex highlights the similarities and differences in the binding mechanisms of the two peptides (FIG. 2F). In both cases, the hydrophobic face of the amphipathic peptide binds the hydrophobic groove in the ECD and the interaction is anchored by the invariant residues R20' and L24' (FIG. 2G). The most notable differences in binding mode occur at the C-termini of the peptides. PTH forms a continuous α-helix from L15' to F34' where the C-terminal amide group forms important hydrogen bonds to the ECD. In contrast, the PTHrP helix extends from I15' to I31', after which it "unwinds", and the C-terminal amide group is not involved in receptor binding. The PTHrP helix curves gently such that its helical axis diverges from that of PTH after residue L24', apparently due to the differences in residues at positions 23', 27', 28', and 31' of the peptides (FIGS. 2F and 2G). The interface of the PTH-ECD complex buries 1883 Å2 of solvent accessible surface area compared to 1743 Å2 for the PTHrP-ECD complex. The surface complementarity between peptide and ECD as measured by the Sc value (33) is slightly higher for the PTH-ECD complex (Sc=0.782) than the PTHrP-ECD complex (Sc=0.726). Thus, the PTH peptide buries slightly more surface area and fits the ECD with slightly "tighter" complementarity than PTHrP. Nonetheless, the peptides exhibit similar affinities for the ECD, possibly as a consequence of the additional hydrogen bonds formed by residues 32-34 of PTHrP (FIG. 2E).

The receptor accommodates the different binding modes of the two peptides with subtle, yet significant changes. The ECD structures in the two complexes are very similar, exhibiting a RMSD of their C-α positions of 0.357 Å, but the side chains of residues L41 and I115 exhibit different conformations in the two structures (FIG. 2F). There appears to be coupling between L41 and I115 of the ECD and positions 23' and 27' of the peptides, respectively. In the PTHrP-bound structure L41 adopts the favored $\chi 1$=gauche(+), $\chi 2$=trans rotamer (34) enabling van der Waals contact between the δ1 methyl group of L41 and the phenyl ring of F23'. In contrast, in the PTH-bound structure L41 adopts the less favored $\chi 1$=trans, $\chi 2$=gauche(−) rotamer, permitting the receptor to accommodate the larger side chain of W23' while retaining van der Waals contact between the δ2 methyl group of L41 and the indole ring of W23'. This L41 rotamer toggle switch mechanism was predicted recently in an elegant study by Donnelly and colleagues (35). I115 adopts the same rotamer in the PTH- and PTHrP-bound structures, but the side chain shifts considerably inward towards the core of the ECD in the PTHrP-bound state, no doubt due to the curvature of the PTHrP helix and the shift in position of residue 27'. This I115 conformation is incompatible with the PTH-binding mode because the δ carbon of I115 and the γ2 carbon of V31' would sterically clash. Thus, the peptide binding site of the ECD exhibits plasticity to adopt the different binding modes of PTH and PTHrP by changing the conformation of residues L41 and I115.

To validate the different binding modes observed in the crystal structures, the inventors examined the contribution of specific PTH and PTHrP residues to ECD binding by assessing the ability of alanine-scan mutants of PTH(15-34)NH$_2$ and PTHrP(12-34)NH$_2$ to compete the interaction of biotinylated PTH with MBP-PTH1R ECD in the AlphaScreen assay. As shown previously (27), PTH residues R20', W23', L24', and L28' were most critical for ECD binding, with additional contributions provided by V21', K27', and F34' (FIG. 2H). PTHrP residues R20', R21', F23', L24', L27', I28', H32', and T33' were all important for ECD binding, with R20' and L24' providing the most critical contacts (FIG. 2I). Notably, F23' and I28' of PTHrP are not as critical for ECD binding as W23' and L28' of PTH. Conversely, L27' and H32' of PTHrP are more important for ECD binding than K27' and H32' of PTH. These in vitro binding results are completely consistent with the binding modes observed in the crystal structures.

Example 5

Binding of Hybrid PTH/PTHrP Peptides to the PTH1R ECD

The inventors sought to determine specifically which residues were responsible for the differing ECD-binding modes of PTH and PTHrP. The crystal structures suggest that the residues at positions 23', 27', 28', and 31' of the peptides largely determine their ECD-binding modes. The inventors reasoned that altering the residues at these positions in one peptide to the corresponding residues present in the other peptide might permit conversion between the PTH- and PTHrP-binding modes. This hypothesis was tested by assessing the binding of hybrid peptides containing swaps of the PTH/PTHrP residues at these four positions to the purified MBP-PTH1R ECD fusion protein in the AlphaScreen assay. The hybrid peptides were made in the PTH(15-34)NH$_2$ and PTHrP(12-34)NH$_2$ scaffolds and included peptides altered by a single swap at one of the four positions, a double swap at two of the four positions, or a quadruple swap at all four positions. Ideally, the quadruple mutants should adopt the binding conformation of the other peptide, retain normal ECD-binding affinity, and exhibit sensitivity to C-terminal amidation—or not—according to their binding mode.

The PTH(15-34)NH$_2$ peptide was relatively intolerant of the corresponding PTHrP residues at positions 23', 31', and to a lesser extent 28' as indicated by the diminished ECD-binding of the W23'F, L28'I, and V31'I singly mutant peptides (FIG. 3A). In contrast, the K27'L mutant retained normal binding and this alteration was able to rescue the defects of the W23'F, L28'I, and V31'I mutations in the W23'F/K27'L, K27'L/L28'I, and K27'L/V31'I doubly mutant peptides. The inclusion of all four swap mutations together in the W23'F/K27'L/L28'I/V31'I peptide resulted in somewhat diminished ECD-binding, suggesting that the differences in the PTH- and PTHrP-binding modes are determined by more than just these four positions, at least for PTH. The combined effect of swaps at all four positions in the PTH scaffold probably pushes PTH towards the PTHrP binding mode, but N33' and F34' of PTH may be incompatible with the PTHrP binding mode (FIG. 2E).

PTHrP(12-34)NH$_2$ exhibited normal ECD-binding when altered with the corresponding PTH residue at positions 23', 28', and 31', but diminished binding with the L27'K alteration (FIG. 3B). The defect of the L27'K alteration was fully rescued by the F23'W alteration and partially rescued by the I28'L or I31'V alterations in the F23'W/L27'K, L27'K/I28'L, and L27'K/I31'V doubly mutant peptides. The quadruply mutant PTHrP peptide exhibited normal binding to the ECD, consistent with the possibility that this peptide adopts the PTH-binding mode.

The most striking feature of the data in FIGS. 3A and 3B is the coupling of positions 23' and 27' that is evident for both peptides. In either scaffold the combination of Phe at position 23' and Lys at position 27' (F23'/K27') resulted in severely diminished ECD binding, while the W23'/K27', W23'/L27', and F23'/L27' combinations were without detriment. The simplest explanation is that the F23'/K27' combination does not bury as much hydrophobic surface area as the other combinations (FIGS. 3C and 3D). The W23'F alteration in PTH would result in less hydrophobic contact to the receptor because of the smaller Phe side chain, and this would be compensated by the additional van der Waals contacts available from a Leu at position 27' (FIG. 3C), explaining the rescue of the W23'F defect by the K27'L alteration. Similarly, the L27'K alteration in PTHrP would result in less hydrophobic contact to the receptor because, unlike Leu, Lys does not branch at the γ carbon (FIG. 3D). The L27'K defect could be compensated by the additional hydrophobic contacts available from a Trp at position 23'.

Example 6

Hybrid PTH/PTHrP Peptides Selective for the G-Protein-Coupled Receptor.

Previous studies indicated that the ECD-binding portion of PTH contributed to its strong binding to the G protein uncoupled receptor (R0) (23, 26). Since PTH and PTHrP exhibit similar affinities for the ECD (FIG. 1), the inventors wondered if the different ECD-binding modes contribute to their R0/RG selectivity differences. To address this question the inventors incorporated the swap mutations into the PTH (1-34)NH2 and PTHrP(1-34)NH2 scaffolds to facilitate analysis of peptide binding to the R0 and RG conformations of PTH1R in cell membranes. Experimentally, the R0 conformation is studied by including GTPγS in the reactions to uncouple receptor and G protein and the RG conformation is studied by co-expressing the receptor with a dominant negative form of Gαs (23, 25). If the differing ECD-binding modes contribute to R0/RG selectivity, then the PTHrP(1-34)NH2 [F23'W/L27'K/I28'L/I31'V] peptide should exhibit reduced RG selectivity (higher R0 affinity) compared to wt PTHrP(1-34) because our ECD binding data was consistent with the idea that this hybrid peptide adopts the PTH ECD-binding mode.

Figure 4A:
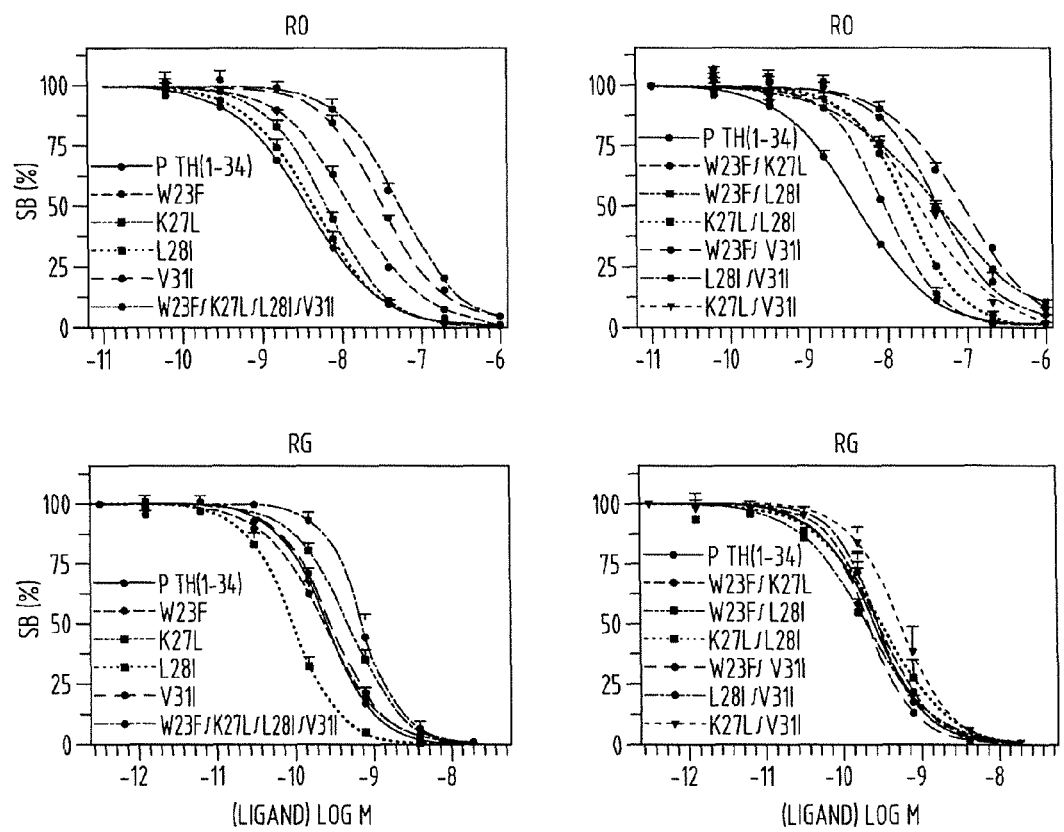
FIGS. 4A and 4B demonstrate the binding of hybrid PTH/PTHrP(1-34)NH2 peptides to R0 and RG states of PTH1R in cell membranes.
Figure 4B:
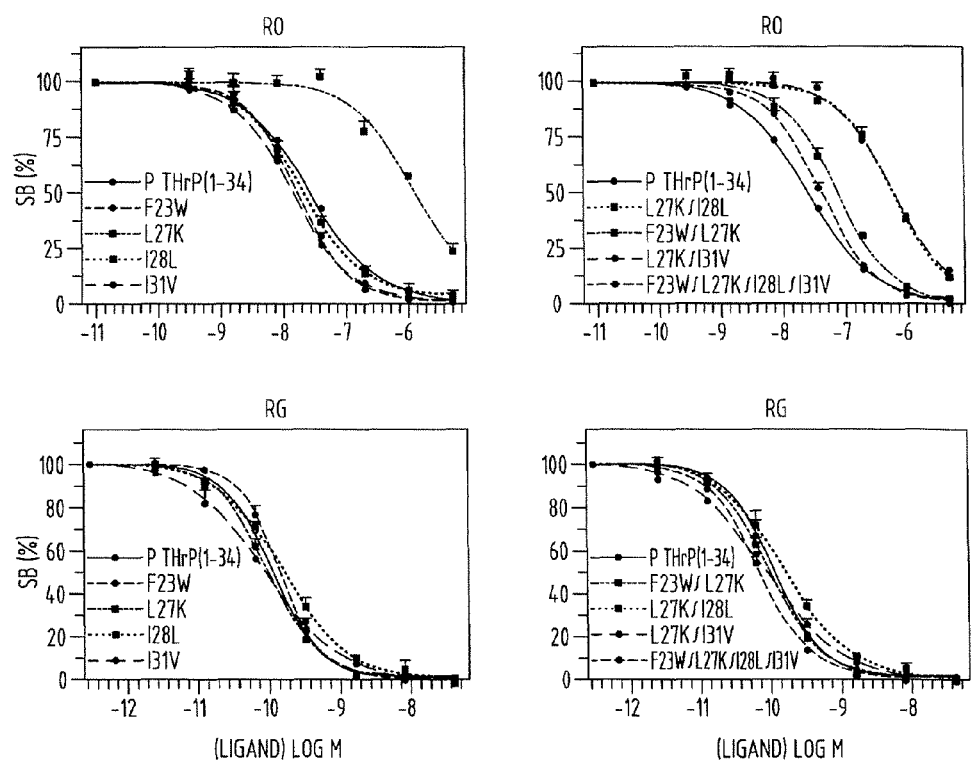

In agreement with previous studies, the wt PTH and PTHrP peptides bound RG with similar high affinity (IC50~0.3 nM for PTH and ~0.1 nM for PTHrP), and PTHrP was more RG-selective, exhibiting 245-fold lower affinity for R0 (IC50~27 nM), while PTH exhibited only ~14-fold lower affinity for R0 (IC50~4 nM) [FIG. 4A, 4B, and Table 3].

TABLE 3

| peptide | $IC_{50}$ Log M, n = 3 (nM) | | RO/RG | SEQ ID No. |
|---|---|---|---|---|
| | RO | RG | | |
| hPTH(1-34) | −8.5 ± 0.12 (3.9 ± 0.9) | −9.6 ± 0.16 (0.28 ± .09) | 13.9 | 9 |
| W23F | −7.9 ± 0.06 (13.5 ± 2.1) | −9.7 ± 0.03 (0.23 ± 0.01) | 59 | 57 |
| K27L | −8.2 ± 0.09 (6.4 ± 1.2) | −9.3 ± 0.13 (0.54 ± 0.15) | 11.9 | 10 |
| L28I | −8.4 ± 0.03 (4.5 ± 0.5) | −10.0 ± 0.07 (0.10 ± 0.02) | 45 | 58 |
| V31I | −7.5 ± 0.04 (34 ± 2.2) | −9.6 ± 0.15 (0.31 ± 0.10) | 110 | 59 |
| W23F/K27L/L28I/V31I | −7.3 ± 0.04 (53 ± 3.4) | −9.2 ± 0.14 (0.78 ± 0.27) | 68 | 60 |
| W23F/K27L | −8.1 ± 0.02 (8.7 ± 0.4) | −9.6 ± 0.18 (0.33 ± 0.13) | 26.4 | 61 |
| W23F/L28I | −7.4 ± 0.04 (38 ± 3.2) | −9.7 ± 0.10 (0.20 ± 0.04) | 190 | 62 |
| K27L/L28I | −7.8 ± 0.02 (16 ± 0.7) | −9.5 ± 0.20 (0.38 ± 0.16) | 42 | 63 |

TABLE 3-continued

| peptide | $IC_{50}$ Log M, n = 3 (nM) | | RO/RG | SEQ ID No. |
|---|---|---|---|---|
| | RO | RG | | |
| W23F/V31I | −7.1 ± 0.01 (81 ± 2.1) | −9.7 ± 0.12 (0.21 ± 0.06) | 386 | 64 |
| L28I/V31I | −7.4 ± 0.10 (42 ± 8.6) | −9.6 ± 0.13 (0.31 ± 0.10) | 135 | 65 |
| K27L/V31I | −7.6 ± 0.01 (25 ± 0.7) | −9.3 ± 0.23 (0.68 ± 0.33) | 36.8 | 66 |
| PTHrP(1-34) | −7.6 ± 0.02 (27 ± 1.4) | −10.0 ± 0.08 (0.11 ± 0.02) | 245 | 79 |
| F23W | −7.8 ± 0.02 (16 ± 0.9) | −9.8 ± 0.08 (0.15 ± 0.03) | 107 | 80 |
| L27K | −5.9 ± 0.02 (1214 ± 60) | −9.8 ± 0.15 (0.16 ± 0.05) | 7588 | 81 |
| I28L | −7.7 ± 0.06 (21 ± 2.5) | −10.0 ± 0.17 (0.11 ± 0.03) | 191 | 82 |
| I31V | −7.9 ± 0.07 (14 ± 2.2) | −9.8 ± 0.06 (0.15 ± 0.02) | 93 | 83 |
| F23W/L27K/I28L/I31V | −7.4 ± 0.05 (41 ± 4.2) | −10.1 ± 0.09 (0.07 ± 0.01) | 586 | 84 |
| F23W/L27K | −7.1 ± 0.05 (77 ± 9.3) | −10.0 ± 0.08 (0.10 ± 0.02) | 770 | 85 |
| L27K/I28L | −6.2 ± 0.06 (598 ± 84) | −9.8 ± 0.19 (0.17 ± 0.06) | 3518 | 86 |
| L27K/I31V | −6.2 ± 0.06 (624 ± 73) | −10.1 ± 0.24 (0.11 ± 0.04) | 5673 | 87 |

The PTHrP(1-34)NH2 [F23'W/L27'K/I28'L/I31'V] peptide—which probably adopts the PTH ECD-binding mode—exhibited slightly decreased R0 affinity (higher RG-selectivity) compared to wild-type PTHrP, suggesting that the different ECD binding modes do not contribute to R0/RG selectivity. In fact, all of the swap mutations that resulted in diminished ECD-binding also resulted in diminished R0 binding while having little or no effect on RG binding, and the extent to which R0 affinity was decreased correlated with ECD-binding ability (FIGS. 3 and 4 and Table 3). PTH(1-34)NH$_2$ [W23'F/V31'I] and PTHrP(1-34)NH$_2$ [L27'K] were most striking; both peptides exhibited poor ECD-binding and dramatically reduced R0 affinity while retaining normal RG affinity. PTHrP(1-34)NH$_2$ [L27'K] was particularly RG-selective, exhibiting a 7588-fold decreased affinity for R0 (IC50~1.2 μM) compared to RG (IC50~0.16 nM). The diminished R0 binding caused by swap alterations that reduced ECD-binding was rescued by additional swap alterations that restored ECD-binding (FIGS. 3 and 4). These results indicate that ECD affinity, rather than ECD-binding mode, is a key determinant of the R0/RG selectivity profile of PTH and PTHrP, and that RG-selectivity can be enhanced by decreasing ECD affinity. The increased RG-selectivity of wt PTHrP compared to wt PTH is probably largely determined by divergent residue 5 (23, 25) because the peptides have similar affinities for the ECD.

Figure 5A:
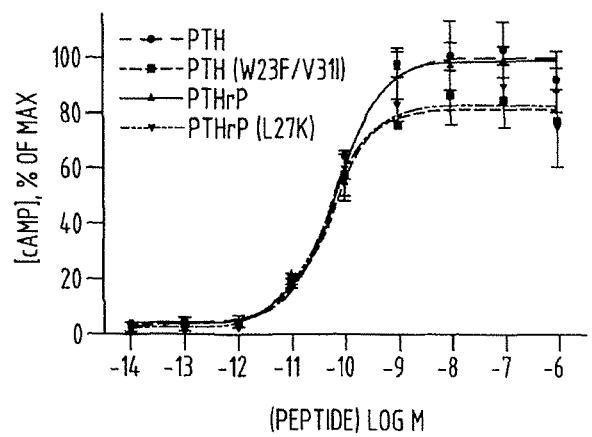
FIGS. 5A and 5B show signaling properties of RG-selective hybrid PTH/PTHrP(1-34)NH2 peptides.
Figure 5B:
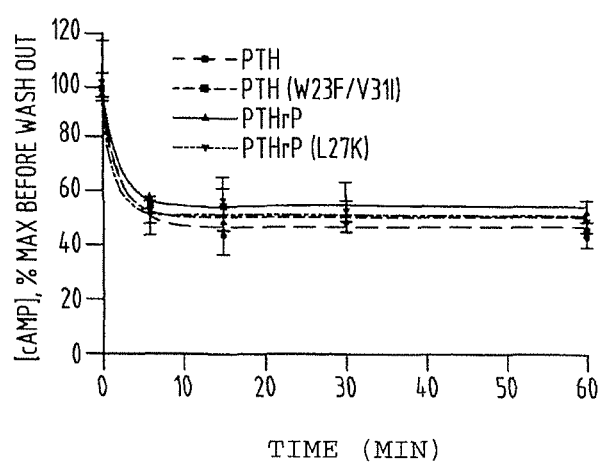
Figure 6A:
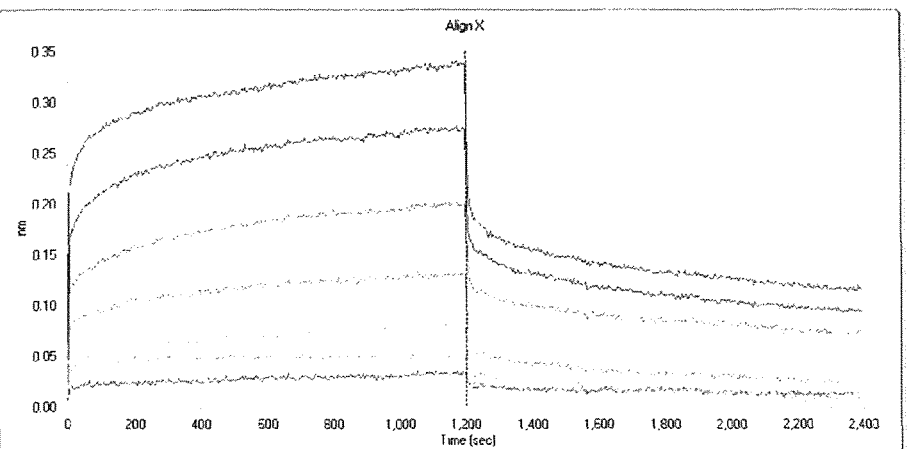
FIGS. 6A and 6B show Octet Red real-time analysis of the binding of PTH and PTHrP to the PTH1R ECD.
Figure 6B:
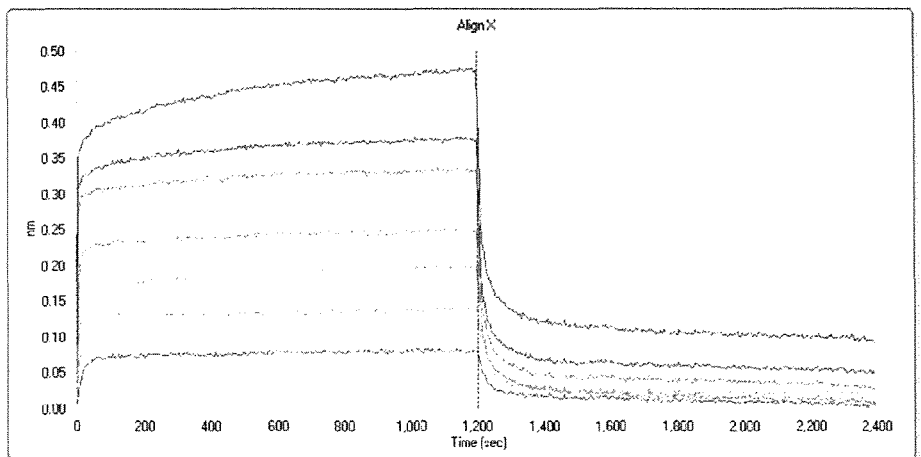

The most RG-selective PTH and PTHrP hybrid peptides were assessed for their ability to stimulate cAMP accumulation in COS cells transiently expressing PTH1R. PTH(1-34)NH2 [W23'F/V31'I] and PTHrP(1-34)NH2 [L27'K] induced cAMP responses with potencies that were essentially the same as the wt peptides, albeit with maximal cAMP levels ~80% of those obtained with the wt peptides (FIG. 5A). The reduced maximal response may reflect sub-stoichiometric G protein levels under these experimental conditions such that a fraction of the receptor always exists in the uncoupled state and is not activated by the RG-selective peptides. To examine the duration of cAMP signaling we employed a ligand washout protocol (26). The cells were subjected to a 10 min stimulation with peptide (100 nM) and cAMP signaling capacity at various times after ligand wash-out was assessed. The RG-selective PTH and PTHrP hybrid peptides exhibited shorter-lived responses than the wt peptides (FIG. 5B), suggesting that the hybrid peptides have a more pulsatile action at the receptor.

xample 7

PTH Analogs and Luciferase Assays

Figure 7A:
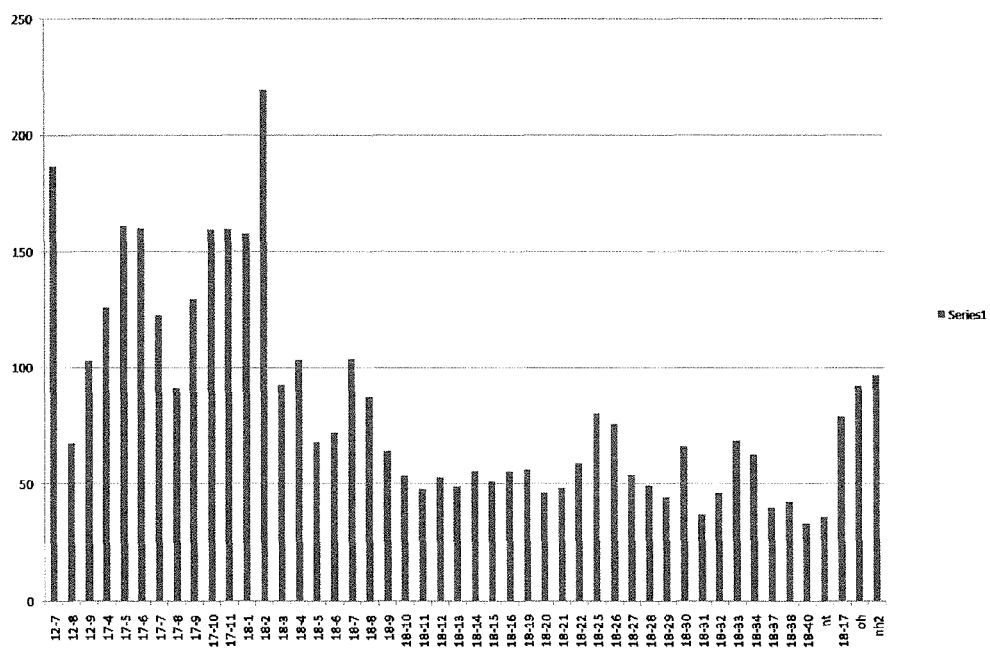
FIGS. 7A and 7B show the results of luciferase assays of PTH analogs. Each of the PTH analogs has an identifier that is given as: ##-##-##-##-SBSL.
Figure 7B:
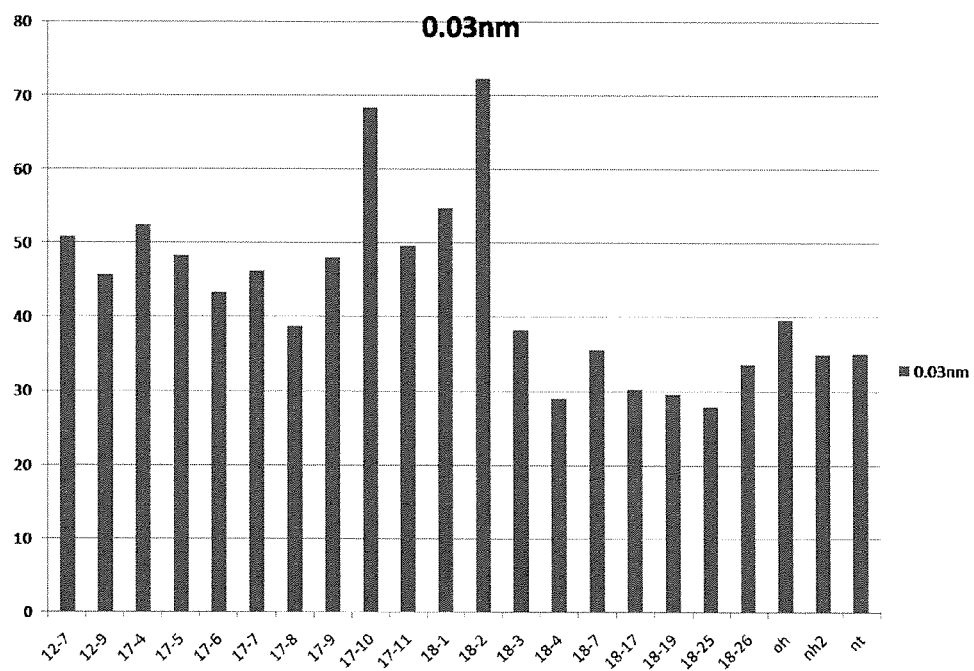

The inventors designed a series of PTH analogs with better potency and selectivity (FIGS. 7A and 7B). Each of the PTH analogs has an identifier that is given as: ##-##-##-##-SBSL. Such PTH peptides or polypeptides consist of a PTH peptide (1-34) with an amino acid substitution at one or more of amino acid positions 12, 14, 16, 17, and 27; and some of the analogs including a disulfide bond from a D-cysteine substitution at position 19 and a cysteine substitution at position 22, or cysteine substitutions at positions 22 and 25 (see, SEQ ID NOs. 1-52) as follows:

TABLE 4

D17(SEQ ID NO. 1):
SVSEIQLMHNLGKHLNDMERVEWLRKKLQDVHNF-CONH2
07-12-17-04-SBSL

N17(SEQ ID NO. 2):
SVSEIQLMHNLGKHLNNMERVEWLRKKLQDVHNF-CONH2
07-12-17-05-SBSL

F14N17(SEQ ID NO. 3):
SVSEIQLMHNLGKFLNNMERVEWLRKKLQDVHNF-CONH2
07-12-17-06-SBSL

V12F14N17(SEQ ID NO. 4):
SVSEIQLMHNLVKFLNNMERVEWLRKKLQDVHNF-CONH2
07-12-17-07-SBSL

V12F14T16N17(SEQ ID NO. 5):
SVSEIQLMHNLVKFLTNMERVEWLRKKLQDVHNF-CONH2
07-12-17-08-SBSL

A12F14N17(SEQ ID NO. 6):
SVSEIQLMHNLAKFLNNMERVEWLRKKLQDVHNF-CONH2
07-12-17-09-SBSL

A12L14N17(SEQ ID NO. 7):
SVSEIQLMHNLAKLLNNMERVEWLRKKLQDVHNF-CONH2
07-12-17-10-SBSL

L14N17(SEQ ID NO. 8):
SVSEIQLMHNLGKLLNNMERVEWLRKKLQDVHNF-CONH2
07-12-17-11-SBSL

PTH(1-34)OH(SEQ ID NO. 9)
SVSEIQLMHNLGKHLNSMERVEWLRKKLQDVHNF-COOH
07-12-12-06-SBSL

PTH(1-34)[K27L]NH2(SEQ ID NO. 10)
SVSEIQLMHNLGKHLNSMERVEWLRKLLQDVHNF-CONH2
07-12-12-07-SBSL

PTH(1-34)[K27L/dC19-C22]NH2(SEQ ID NO. 11)
SVSEIQLMHNLGKHLNSM(dC)RVCWLRKLLQDVHNF-CONH2
(intramolecular disulfide bond of D-amino acid
C19 "dC19" and C22 with L27)
07-12-12-08-SBSL PTH(1-34)[K27L/C22-C25]NH2(SEQ ID NO. 12)
SVSEIQLMHNLGKHLNSMERVCWLCKLLQDVHNF-CONH2
(intramolecular disulfide bond of C22 and C25
with L27)
07-12-12-08-SBSL TABLE 4-continued

L27D17(SEQ ID NO. 13):
SVSEIQLMHNLGKHLNDMERVEWLRKLLQDVHNF-CONH2
07-12-18-01-SBSL

L27N17(SEQ ID NO. 14):
SVSEIQLMHNLGKHLNNMERVEWLRKLLQDVHNF-CONH2
07-12-18-02-SBSL

L27F14N17(SEQ ID NO. 15):
SVSEIQLMHNLGKFLNNMERVEWLRKLLQDVHNF-CONH2
07-12-18-03-SBSL

L27V12F14N17(SEQ ID NO. 16):
SVSEIQLMHNLVKFLNNMERVEWLRKLLQDVHNF-CONH2
07-12-18-04-SBSL

L27V12F14T16N17(SEQ ID NO. 17):
SVSEIQLMHNLVKFLTNMERVEWLRKLLQDVHNF-CONH2
07-12-18-05-SBSL

L27A12F14N17(SEQ ID NO. 18):
SVSEIQLMHNLAKFLNNMERVEWLRKLLQDVHNF-CONH2
07-12-18-06-SBSL

L27A12L14N17(SEQ ID NO. 19):
SVSEIQLMHNLAKLLNNMERVEWLRKLLQDVHNF-CONH2
07-12-18-07-SBSL

L27L14N17(SEQ ID NO. 20):
SVSEIQLMHNLGKLLNNMERVEWLRKLLQDVHNF-CONH2
07-12-18-08-SBSL

The peptides below have a disulfide bond between
C22 and C25 with L27:

(C22-C25)L27D17(SEQ ID NO. 21):
SVSEIQLMHNLGKHLNDMERVCWLCKLLQDVHNF-CONH2
07-12-18-09-SBSL (C22-C25)L27N17(SEQ ID NO. 22):
SVSEIQLMHNLGKHLNNMERVCWLCKLLQDVHNF-CONH2
07-12-18-10-SBSL (C22-C25)L27F14N17(SEQ ID NO. 23):
SVSEIQLMHNLGKFLNNMERVCWLCKLLQDVHNF-CONH2
07-12-18-11-SBSL (C22-C25)L27V12F14N17(SEQ ID NO. 24):
SVSEIQLMHNLVKFLNNMERVCWLCKLLQDVHNF-CONH2
07-12-18-12-SBSL (C22-C25)L27V12F14T16N17(SEQ ID NO. 25):
SVSEIQLMHNLVKFLTNMERVCWLCKLLQDVHNF-CONH2
07-12-18-13-SBSL (C22-C25)L27A12F14N17(SEQ ID NO. 26):
SVSEIQLMHNLAKFLNNMERVCWLCKLLQDVHNF-CONH2
07-12-18-14-SBSL (C22-C25)L27A12L14N17(SEQ ID NO. 27):
SVSEIQLMHNLAKLLNNMERVCWLCKLLQDVHNF-CONH2
07-12-18-15-SBSL (C22-C25)L27L14N17(SEQ ID NO. 28):
SVSEIQLMHNLGKLLNNMERVCWLCKLLQDVHNF-CONH2
07-12-18-16-SBSL

The peptides below have a disulfide bond between
C22 and C25 with K27:

(C22-C25)K27D17(SEQ ID NO. 29):
SVSEIQLMHNLGKHLNDMERVCWLCKKLQDVHNF-CONH2
07-12-18-17-SBSL (C22-C25)K27N17(SEQ ID NO. 30):
SVSEIQLMHNLGKHLNNMERVCWLCKKLQDVHNF-CONH2
07-12-18-18-SBSL (C22-C25)K27F14N17(SEQ ID NO. 31):
SVSEIQLMHNLGKFLNNMERVCWLCKKLQDVHNF-CONH2
07-12-18-19-SBSL

TABLE 4-continued (C22-C25)K27V12F14N17(SEQ ID NO. 32):
SVSEIQLMHNLVKFLNNMERVCWLCKKLQDVHNF-CONH2
07-12-18-20-SBSL (C22-C25)K27V12F14T16N17(SEQ ID NO. 33):
SVSEIQLMHNLVKFLTNMERVCWLCKKLQDVHNF-CONH2
07-12-18-21-SBSL (C22-C25)K27A12F14N17(SEQ ID NO. 34):
SVSEIQLMHNLAKFLNNMERVCWLCKKLQDVHNF-CONH2
07-12-18-22-SBSL (C22-C25)K27A12L14N17(SEQ ID NO. 35):
SVSEIQLMHNLAKLLNNMERVCWLCKKLQDVHNF-CONH2
07-12-18-23-SBSL (C22-C25)K27L14N17(SEQ ID NO. 36):
SVSEIQLMHNLGKLLNNMERVCWLCKKLQDVHNF-CONH2
07-12-18-24-SBSL The peptides below have a disulfide bond between
D-amino acid C19 (dC19) and C22 with L27:

(dC19-C22)L27D17(SEQ ID NO. 37):
SVSEIQLMHNLGKHLNDM(dC)RVCWLRKLLQDVHNF-CONH2
07-12-18-25-SBSL (dC19-C22)L27N17(SEQ ID NO. 38):
SVSEIQLMHNLGKHLNNM(dC)RVCWLRKLLQDVHNF-CONH2
07-12-18-26-SBSL (dC19-C22)L27F14N17(SEQ ID NO. 39):
SVSEIQLMHNLGKFLNNM(dC)RVCWLRKLLQDVHNF-CONH2
07-12-18-27-SBSL (dC19-C22)L27V12F14N17(SEQ ID NO. 40):
SVSEIQLMHNLVKFLNNM(dC)RVCWLRKLLQDVHNF-CONH2
07-12-18-28-SBSL (dC19-C22)L27V12F14T16N17(SEQ ID NO. 41):
SVSEIQLMHNLVKFLTNM(dC)RVCWLRKLLQDVHNF-CONH2
07-12-18-29-SBSL (dC19-C22)L27A12F14N17(SEQ ID NO. 42):
SVSEIQLMHNLAKFLNNM(dC)RVCWLRKLLQDVHNF-CONH2
07-12-18-30-SBSL (dC19-C22)L27A12L14N17(SEQ ID NO. 43):
SVSEIQLMHNLAKLLNNM(dC)RVCWLRKLLQDVHNF-CONH2
07-12-18-31-SBSL (dC19-C22)L27L14N17(SEQ ID NO. 44):
SVSEIQLMHNLGKLLNNM(dC)RVCWLRKLLQDVHNF-CONH2
07-12-18-32-SBSL

The peptides below have a disulfide bond between
D-amino acid C19 (dC19) and C22 with K27:

(dC19-C22)K27D17(SEQ ID NO. 45):
SVSEIQLMHNLGKHLNDM(dC)RVCWLRKKLQDVHNF-CONH2
07-12-18-33-SBSL (dC19-C22)K27N17(SEQ ID NO. 46):
SVSEIQLMHNLGKHLNNM(dC)RVCWLRKKLQDVHNF-CONH2
07-12-18-34-SBSL (dC19-C22)K27F14N17(SEQ ID NO. 47):
SVSEIQLMHNLGKFLNNM(dC)RVCWLRKKLQDVHNF-CONH2
07-12-18-35-SBSL (dC19-C22)K27V12F14N17(SEQ ID NO. 48):
SVSEIQLMHNLVKFLNNM(dC)RVCWLRKKLQDVHNF-CONH2
07-12-18-36-SBSL (dC19-C22)K27V12F14T16N17(SEQ ID NO. 49):
SVSEIQLMHNLVKFLTNM(dC)RVCWLRKKLQDVHNF-CONH2
07-12-18-37-SBSL

TABLE 4-continued (dC19-C22)K27A12F14N17(SEQ ID NO. 50):
SVSEIQLMHNLAKFLNNM(dC)RVCWLRKKLQDVHNF-CONH2
07-12-18-38-SBSL (dC19-C22)K27A12L14N17(SEQ ID NO. 51):
SVSEIQLMHNLAKLLNNM(dC)RVCWLRKKLQDVHNF-CONH2
07-12-18-39-SBSL (dC19-C22)K27L14N17(SEQ ID NO. 52):
SVSEIQLMHNLGKLLNNM(dC)RVCWLRKKLQDVHNF-CONH2
07-12-18-40-SBSL Cell Culture for PTH Analog Luciferase Assays:

AD-293 cells (Stratagene) were maintained in alpha-MEM supplemented with 10% FBS at 37° C. under 5% CO2 and at 95% humidity.

PTH Analog Luciferase Assay:

AD293 cells (stratagene) were plated into 24-well dishes 24 hr before co-transfection with CRE-luciferase (pGL4.29/CRE-luc2p, promega, 200 ng/well), pcDNA-PTH1R (10 ng/well) and pHRLTK (Renilla luciferase, 5 ng/well) using Lipofectamine2000 (Invitrogen) according to the manufacture's protocol. The medium in cell culture was replaced by OPTI-MEM without FBS during transfection. Various concentrations of PTH analogs (0.1 nM or 0.03 nM) were then added to the culture medium 24 hr following transfection and Luciferase activity in transfected cells was determined with Dual-luciferase assay kit (promega) in 4 hr. See FIGS. 7A and 7B).

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the spirit and scope of the invention.

REFERENCES

The following references have been cited throughout the present disclosures according to the number indicated in the listing below.

1. Juppner, H., Abou-Samra, A. B., Freeman, M., Kong, X. F., Schipani, E., Richards, J., Kolakowski, L. F., Jr., Hock, J., Potts, J. T., Jr., Kronenberg, H. M., et al. (1991) A G protein-linked receptor for parathyroid hormone and parathyroid hormone-related peptide. *Science* (New York, N.Y. 254, 1024-1026.
2. Gardella, T. J. & Juppner, H. (2000) Interaction of PTH and PTHrP with their receptors. Reviews in endocrine & metabolic disorders 1, 317-329.
3. Gensure, R. C., Gardella, T. J., & Juppner, H. (2005) Parathyroid hormone and parathyroid hormone-related peptide, and their receptors. Biochemical and biophysical research communications 328, 666-678.
4. Murray, T. M., Rao, L. G., Divieti, P., & Bringhurst, F. R. (2005) Parathyroid hormone secretion and action: evidence for discrete receptors for the carboxyl-terminal region and related biological actions of carboxyl-terminal ligands. Endocrine reviews 26, 78-113.
5. Potts, J. T. (2005) Parathyroid hormone: past and present. The Journal of endocrinology 187, 311-325.
6. Potts, J. T. & Gardella, T. J. (2007) Progress, paradox, and potential: parathyroid hormone research over five decades. Annals of the New York Academy of Sciences 1117, 196-208.

7. Jilka, R. L. (2007) Molecular and cellular mechanisms of the anabolic effect of intermittent PTH. Bone 40, 1434-1446.
8. Neer, R. M., Arnaud, C. D., Zanchetta, J. R., Prince, R., Gaich, G. A., Reginster, J. Y., Hodsman, A. B., Eriksen, E. F., Ish-Shalom, S., Genant, H. K., et al. (2001) Effect of parathyroid hormone (1-34) on fractures and bone mineral density in postmenopausal women with osteoporosis. The New England journal of medicine 344, 1434-1441.
9. Burtis, W. J., Wu, T., Bunch, C., Wysolmerski, J. J., Insogna, K. L., Weir, E. C., Broadus, A. E., & Stewart, A. F. (1987) Identification of a novel 17,000-dalton parathyroid hormone-like adenylate cyclase-stimulating protein from a tumor associated with humoral hypercalcemia of malignancy. The Journal of biological chemistry 262, 7151-7156.
10. Moseley, J. M., Kubota, M., Diefenbach-Jagger, H., Wettenhall, R. E., Kemp, B. E., Suva, L. J., Rodda, C. P., Ebeling, P. R., Hudson, P. J., Zajac, J. D., et al. (1987) Parathyroid hormone-related protein purified from a human lung cancer cell line. Proceedings of the National Academy of Sciences of the United States of America 84, 5048-5052.
11. Suva, L. J., Winslow, G. A., Wettenhall, R. E., Hammonds, R. G., Moseley, J. M., Diefenbach-Jagger, H., Rodda, C. P., Kemp, B. E., Rodriguez, H., Chen, E. Y., et al. (1987) A parathyroid hormone-related protein implicated in malignant hypercalcemia: cloning and expression. Science (New York, N.Y. 237, 893-896.
12. Klein, R. F., Strewler, G. J., Leung, S. C., & Nissenson, R. A. (1987) Parathyroid hormone-like adenylate cyclase-stimulating activity from a human carcinoma is associated with bone-resorbing activity. Endocrinology 120, 504-511.
13. Karaplis, A. C., Luz, A., Glowacki, J., Bronson, R. T., Tybulewicz, V. L., Kronenberg, H. M., & Mulligan, R. C. (1994) Lethal skeletal dysplasia from targeted disruption of the parathyroid hormone-related peptide gene. Genes & development 8, 277-289.
14. Lanske, B., Karaplis, A. C., Lee, K., Luz, A., Vortkamp, A., Pirro, A., Karperien, M., Defize, L. H., Ho, C., Mulligan, R. C., et al. (1996) PTH/PTHrP receptor in early development and Indian hedgehog-regulated bone growth. Science (New York, N.Y. 273, 663-666.
15. Kronenberg, H. M. (2006) PTHrP and skeletal development. Annals of the New York Academy of Sciences 1068, 1-13.
16. Horwitz, M. J., Tedesco, M. B., Gundberg, C., Garcia-Ocana, A., & Stewart, A. F. (2003) Short-term, high-dose parathyroid hormone-related protein as a skeletal anabolic agent for the treatment of postmenopausal osteoporosis. The Journal of clinical endocrinology and metabolism 88, 569-575.
17. Plotkin, H., Gundberg, C., Mitnick, M., & Stewart, A. F. (1998) Dissociation of bone formation from resorption during 2-week treatment with human parathyroid hormone-related peptide-(1-36) in humans: potential as an anabolic therapy for osteoporosis. The Journal of clinical endocrinology and metabolism 83, 2786-2791.
18. Yang, D., Singh, R., Divieti, P., Guo, J., Bouxsein, M. L., & Bringhurst, F. R. (2007) Contributions of parathyroid hormone (PTH)/PTH-related peptide receptor signaling pathways to the anabolic effect of PTH on bone. Bone 40, 1453-1461.
19. Bergwitz, C., Gardella, T. J., Flannery, M. R., Potts, J. T., Jr., Kronenberg, H. M., Goldring, S. R., & Juppner, H. (1996) Full activation of chimeric receptors by hybrids between parathyroid hormone and calcitonin. Evidence for a common pattern of ligand-receptor interaction. The Journal of biological chemistry 271, 26469-26472.
20. Luck, M. D., Carter, P. H., & Gardella, T. J. (1999) The (1-14) fragment of parathyroid hormone (PTH) activates intact and amino-terminally truncated PTH-1 receptors. Molecular endocrinology (Baltimore, Md. 13, 670-680.
21. Marx, U. C., Adermann, K., Bayer, P., Forssmann, W. G., & Rosch, P. (2000) Solution structures of human parathyroid hormone fragments hPTH(1-34) and hPTH (1-39) and bovine parathyroid hormone fragment bPTH (1-37). Biochemical and biophysical research communications 267, 213-220.
22. Weidler, M., Marx, U. C., Seidel, G., Schafer, W., Hoffmann, E., Esswein, A., & Rosch, P. (1999) The structure of human parathyroid hormone-related protein (1-34) in near-physiological solution. FEBS letters 444, 239-244.
23. Dean, T., Vilardaga, J. P., Potts, J. T., Jr., & Gardella, T. J. (2008) Altered selectivity of parathyroid hormone (PTH) and PTH-related protein (PTHrP) for distinct conformations of the PTH/PTHrP receptor. Molecular endocrinology (Baltimore, Md. 22, 156-166.
24. Dean, T., Linglart, A., Mahon, M. J., Bastepe, M., Juppner, H., Potts, J. T., Jr., & Gardella, T. J. (2006) Mechanisms of ligand binding to the parathyroid hormone (PTH)/PTH-related protein receptor: selectivity of a modified PTH(1-15) radioligand for GalphaS-coupled receptor conformations. Molecular endocrinology (Baltimore, Md. 20, 931-943.
25. Hoare, S. R., Gardella, T. J., & Usdin, T. B. (2001) Evaluating the signal transduction mechanism of the parathyroid hormone 1 receptor. Effect of receptor-G-protein interaction on the ligand binding mechanism and receptor conformation. The Journal of biological chemistry 276, 7741-7753.
26. Okazaki, M., Ferrandon, S., Vilardaga, J. P., Bouxsein, M. L., Potts, J. T., Jr., & Gardella, T. J. (2008) Prolonged signaling at the parathyroid hormone receptor by peptide ligands targeted to a specific receptor conformation. Proceedings of the National Academy of Sciences of the United States of America 105, 16525-16530.
27. Pioszak, A. A. & Xu, H. E. (2008) Molecular recognition of parathyroid hormone by its G protein-coupled receptor. Proceedings of the National Academy of Sciences of the United States of America 105, 5034-5039.
28. Parthier, C., Kleinschmidt, M., Neumann, P., Rudolph, R., Manhart, S., Schlenzig, D., Fanghanel, J., Rahfeld, J. U., Demuth, H. U., & Stubbs, M. T. (2007) Crystal structure of the incretin-bound extracellular domain of a G protein-coupled receptor. Proceedings of the National Academy of Sciences of the United States of America 104, 13942-13947.
29. Pioszak, A. A., Parker, N. R., Suino-Powell, K., & Xu, H. E. (2008) Molecular recognition of corticotropin-releasing factor by its G-protein-coupled receptor CRFR1. The Journal of biological chemistry 283, 32900-32912.
30. Runge, S., Thogersen, H., Madsen, K., Lau, J., & Rudolph, R. (2008) Crystal structure of the ligand-bound glucagon-like peptide-1 receptor extracellular domain. The Journal of biological chemistry 283, 11340-11347.
31. Grauschopf, U., Lilie, H., Honold, K., Wozny, M., Reusch, D., Esswein, A., Schafer, W., Rucknagel, K. P., & Rudolph, R. (2000) The N-terminal fragment of human parathyroid hormone receptor 1 constitutes a hormone binding domain and reveals a distinct disulfide pattern. Biochemistry 39, 8878-8887.
32. Gensure, R. C., Shimizu, N., Tsang, J., & Gardella, T. J. (2003) Identification of a contact site for residue 19 of parathyroid hormone (PTH) and PTH-related protein analogs in transmembrane domain two of the type 1 PTH receptor. Molecular endocrinology (Baltimore, Md. 17, 2647-2658.
33. Lawrence, M. C. & Colman, P. M. (1993) Shape complementarity at protein/protein interfaces. Journal of molecular biology 234, 946-950.
34. Penel, S. & Doig, A. J. (2001) Rotamer strain energy in protein helices—quantification of a major force opposing protein folding. Journal of molecular biology 305, 961-968.
35. Mann, R., Wigglesworth, M. J., & Donnelly, D. (2008) Ligand-receptor interactions at the parathyroid hormone receptors: subtype binding selectivity is mediated via an interaction between residue 23 on the ligand and residue 41 on the receptor. Molecular pharmacology 74, 605-613.
36. Hoare, S. R., Clark, J. A., & Usdin, T. B. (2000) Molecular determinants of tuberoinfundibular peptide of 39 residues (TIP39) selectivity for the parathyroid hormone-2 (PTH2) receptor. N-terminal truncation of TIP39 reverses PTH2 receptor/PTH1 receptor binding selectivity. The Journal of biological chemistry 275, 27274-27283.
37. Otwinowski, Z. & Minor, W. (1997) Processing of X-ray diffraction data collected in oscillation mode. Methods in enzymology 276 (Pt A), 307-326.
38. (1994) The CCP4 suite: programs for protein crystallography. Acta crystallographica 50, 760-763.
39. McCoy, A. J., Grosse-Kunstleve, R. W., Adams, P. D., Winn, M. D., Storoni, L. C., & Read, R. J. (2007) Phaser Crystallographic Software. Journal of Applied Crystallography 40, 658-674.
40. Kleywegt, G. J. & Jones, T. A. (1997) Model building and refinement practice. Methods in enzymology 277, 208-230.
41. Murshudov, G. N., Vagin, A. A., & Dodson, E. J. (1997) Refinement of macromolecular structures by the maximum-likelihood method. Acta crystallographica 53, 240-255.
42. Winn, M. D., Isupov, M. N., & Murshudov, G. N. (2001) Use of TLS parameters to model anisotropic displacements in macromolecular refinement. Acta crystallographica 57, 122-133.
43. Laskowski, R. A., MacArthur, M. W., Moss, D. S., & Thornton, J. M. (1993) PROCHECK: a program to check the stereochemical quality of protein structures. Journal of Applied Crystallography 26, 283-291.
44. DeLano, W. (2002) The PyMol Molecular Graphics System. DeLano Scientific, Palo Alto, Calif., USA.
45. Pioszak, A. A. & Xu, H. E. (2008) Proceedings of the National Academy of Sciences of the United States of America 105, 5034-5039.
46. Bradford, M. M. (1976) Analytical biochemistry 72, 248-254.

---

What is claimed is:

1. An isolated Parathyroid Hormone-related Protein (PTHrP) peptide or analog thereof comprising amino acids 12-34 of SEQ ID NO: 79 with an amino acid substitution at one, two, or three of positions 27, 20, 21, 24, 28, and 33 of SEQ ID NO: 79.

2. The PTHrP peptide or analog of claim 1, wherein the PTHrP peptide or analog exhibits decreased affinity for the G protein-uncoupled conformation (R0) of PTH1R, as compared to the affinity of wild-type PTHrP (SEQ ID NO: 79) for the R0 conformation of PTH1R, wherein the PTHrP peptide or analog retains binding to the G protein-coupled conformation (RG) of PTH1R, and wherein the PTHrP peptide or analog stimulates cyclic AMP (cAMP) accumulation in cells.

3. The PTHrP peptide or analog of claim 2, wherein the amino acid at one, two, or three of positions 27, 20, 21, 24, 28, and 33 of SEQ ID NO: 79 is replaced with the amino acid at the corresponding position of SEQ ID NO: 9.

4. The PTHrP peptide or analog of claim 1, further comprising amino acids 1-34 of SEQ ID NO: 79 with an amino acid substitution at one, two, three, or four of positions 27, 20, 21, 24, 28, and 33 of SEQ ID NO: 79.

5. The PTHrP peptide or analog of claim 4, wherein the amino acid sequence is any of SEQ ID NOs: 81, 82, 85, 86, 88, 93-94 and 96-98, and 101.

6. The PTHrP peptide or analog of claim 1, wherein the PTHrP peptide or analog exhibits a shorter-lived cAMP response compared to the cAMP response of wild-type PTHrP (SEQ ID NO: 79).

7. The PTHrP peptide or analog of claim 1, wherein the PTHrP peptide or analog comprises SEQ ID NO: 81.

8. The PTHrP peptide or analog of claim 1, wherein the PTHrP peptide comprises an amino acid substitution at position 27 of SEQ ID NO: 79.

9. The PTHrP peptide or analog of claim 1, comprising an Ala at one, two, or three of positions 27, 20, 21, 24, 28, and 33.

10. A chemical derivative comprising a PTHrP peptide or analog of claim 1 and a chemical moiety which is not a part of wild-type PTHrP (SEQ ID NO: 79).

11. A fusion polypeptide comprising (a) a PTHrP peptide or analog of claim 1, (b) optionally, a linker region, and (c) a second polypeptide linked to the PTHrP peptide or analog, or to the linker region, wherein the second polypeptide is not natively linked to the PTHrP peptide or analog.

12. A multimeric peptide comprising a basic peptidic sequence repeated from about two to about 100 times, wherein the basic peptidic sequence is the amino acid sequence of the PTHrP peptide or analog of claim 1, and optionally comprising a spacer.

13. A pharmaceutical composition comprising a PTHrP peptide or analog of claim 1.

14. A kit for treating osteoporosis comprising a PTHrP peptide or analog according to claim 1, and instructions for administration thereof to a subject having osteoporosis.

15. A method for activating a PTH receptor in a cell, comprising administering to the cell the PTHrP peptide or analog of claim 1, such that the PTHrP peptide or analog causes the PTH receptor to be activated.

16. The method of claim 15, wherein the cell is an osteoblast.

17. The method of claim 15, wherein the cell is in a live animal and the PTHrP peptide or analog is administered to the live animal.

18. The method of claim 17, wherein the live animal is a human.

19. The method of claim 17, wherein the PTHrP peptide or analog is administered by oral delivery or injection.

20. A method of treating a subject having a disease or condition associated with undesired bone loss, comprising administering to the subject the pharmaceutical composition of claim 13 in an amount and dosing regime effective to treat the subject.

21. The method of claim 20, wherein the subject is a human.

22. The method of claim 20, wherein the disease or condition is osteoporosis.

23. A method of ameliorating a symptom associated with osteoporosis in a subject in need thereof, comprising administering to the subject the pharmaceutical composition of claim 13 in an amount and dosing regime effective to ameliorate a symptom associated with osteoporosis in the subject.

24. A method of retarding the progression of osteoporosis in a subject in need thereof, comprising administering to the subject the pharmaceutical composition of claim 13 in an amount and dosing regime effective to retard the progression of osteoporosis in the subject.

25. A method of regenerating bone in a subject in need thereof, comprising administering to the subject the pharmaceutical composition of claim 13 in an amount and dosing regime effective to regenerate bone in the subject.

26. An isolated Parathyroid Hormone-related Protein (PTHrP) peptide or analog thereof comprising amino acids 12-34 of SEQ ID NO: 79 with an amino acid substitution at (a) one or two of positions 27 and 28 of SEQ ID NO: 79 or (b) two, three, or four of positions 27, 23, 28, and 31 of SEQ ID NO: 79.

27. The PTHrP peptide or analog of claim 26, further comprising amino acids 1-34 of SEQ ID NO: 79 with an amino acid substitution at (a) one or two of positions 27 and 28 of SEQ ID NO: 79 or (b) two, three, or four of positions 27, 23, 28, and 31 of SEQ ID NO: 79.

28. The PTHrP peptide or analog of claim 26 wherein the amino acid substitution at (a) position 28 of SEQ ID NO: 79 is a conservative substitution or (b) two or three of positions 23, 28, and 31 of SEQ ID NO: 79 is a conservative substitution.

29. The PTHrP peptide or analog of claim 26, wherein the amino acid at (a) one or two, of positions 27 and 28 of SEQ ID NO: 79 is replaced with the amino acid at the corresponding position of SEQ ID NO: 9 or (b) two, three, or four of positions 27, 23, 28, and 31 of SEQ ID NO: 79 is replaced with the amino acid at the corresponding position of SEQ ID NO: 9.

30. The PTHrP peptide or analog of claim 26, further comprising (a) a chemical moiety which is not a part of wild-type PTHrP (SEQ ID NO: 79), (b) a linker region and a second polypeptide linked to the PTHrP peptide, or to the linker region, wherein the second polypeptide is not natively linked to the PTHrP peptide, or (c) a spacer and a basic peptidic sequence repeated from about one to about 100 times, wherein the basic peptidic sequence is the amino acid sequence of the PTHrP peptide or analog of claim 1.

31. An isolated Parathyroid Hormone-related Protein (PTHrP) peptide or analog comprising amino acids 1-34 of SEQ ID NO: 79, wherein the amino acid sequence is any of SEQ ID NOs: 83, 84, 87, 89, 90, 99, or 100.

* * * * *

SEQUENCE LISTING

```
<160> NUMBER OF SEQ ID NOS: 101

<210> SEQ ID NO 1
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 1

Ser Val Ser Glu Ile Gln Leu Met His Asn Leu Gly Lys His Leu Asn
1               5                   10                  15

Asp Met Glu Arg Val Glu Trp Leu Arg Lys Lys Leu Gln Asp Val His
            20                  25                  30

Asn Phe

<210> SEQ ID NO 2
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 2

Ser Val Ser Glu Ile Gln Leu Met His Asn Leu Gly Lys His Leu Asn
1               5                   10                  15

Asn Met Glu Arg Val Glu Trp Leu Arg Lys Lys Leu Gln Asp Val His
            20                  25                  30

Asn Phe
```

```
<210> SEQ ID NO 3
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 3

Ser Val Ser Glu Ile Gln Leu Met His Asn Leu Gly Lys Phe Leu Asn
1               5                   10                  15

Asn Met Glu Arg Val Glu Trp Leu Arg Lys Lys Leu Gln Asp Val His
            20                  25                  30

Asn Phe

<210> SEQ ID NO 4
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 4

Ser Val Ser Glu Ile Gln Leu Met His Asn Leu Val Lys Phe Leu Asn
1               5                   10                  15

Asn Met Glu Arg Val Glu Trp Leu Arg Lys Lys Leu Gln Asp Val His
            20                  25                  30

Asn Phe

<210> SEQ ID NO 5
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 5

Ser Val Ser Glu Ile Gln Leu Met His Asn Leu Val Lys Phe Leu Thr
1               5                   10                  15

Asn Met Glu Arg Val Glu Trp Leu Arg Lys Lys Leu Gln Asp Val His
            20                  25                  30

Asn Phe

<210> SEQ ID NO 6
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 6

Ser Val Ser Glu Ile Gln Leu Met His Asn Leu Ala Lys Phe Leu Asn
1               5                   10                  15

Asn Met Glu Arg Val Glu Trp Leu Arg Lys Lys Leu Gln Asp Val His
            20                  25                  30

Asn Phe

<210> SEQ ID NO 7
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 7
```

```
Ser Val Ser Glu Ile Gln Leu Met His Asn Leu Ala Lys Leu Leu Asn
1               5                   10                  15

Asn Met Glu Arg Val Glu Trp Leu Arg Lys Lys Leu Gln Asp Val His
            20                  25                  30

Asn Phe

<210> SEQ ID NO 8
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 8

Ser Val Ser Glu Ile Gln Leu Met His Asn Leu Gly Lys Leu Leu Asn
1               5                   10                  15

Asn Met Glu Arg Val Glu Trp Leu Arg Lys Lys Leu Gln Asp Val His
            20                  25                  30

Asn Phe

<210> SEQ ID NO 9
<211> LENGTH: 34
<212> TYPE: PRT
<213> ORGANISM: Homo sapiens
<220> FEATURE:
<221> NAME/KEY: MISC_FEATURE
<223> OTHER INFORMATION: Protein fragment including amino acids 1-34 of
      parathyroid hormone

<400> SEQUENCE: 9

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 10
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 10

Ser Val Ser Glu Ile Gln Leu Met His Asn Leu Gly Lys His Leu Asn
1               5                   10                  15

Ser Met Glu Arg Val Glu Trp Leu Arg Lys Leu Leu Gln Asp Val His
            20                  25                  30

Asn Phe

<210> SEQ ID NO 11
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (19)..(19)
<223> OTHER INFORMATION: This is the dextrorotary form of cysteine

<400> SEQUENCE: 11

Ser Val Ser Glu Ile Gln Leu Met His Asn Leu Gly Lys His Leu Asn
```

```
                1               5                  10                 15
Ser Met Cys Arg Val Cys Trp Leu Arg Lys Leu Leu Gln Asp Val His
            20                 25                 30

Asn Phe

<210> SEQ ID NO 12
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 12

Ser Val Ser Glu Ile Gln Leu Met His Asn Leu Gly Lys His Leu Asn
1               5                  10                 15

Ser Met Glu Arg Val Cys Trp Leu Cys Lys Leu Leu Gln Asp Val His
            20                 25                 30

Asn Phe

<210> SEQ ID NO 13
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 13

Ser Val Ser Glu Ile Gln Leu Met His Asn Leu Gly Lys His Leu Asn
1               5                  10                 15

Asp Met Glu Arg Val Glu Trp Leu Arg Lys Leu Leu Gln Asp Val His
            20                 25                 30

Asn Phe

<210> SEQ ID NO 14
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 14

Ser Val Ser Glu Ile Gln Leu Met His Asn Leu Gly Lys His Leu Asn
1               5                  10                 15

Asn Met Glu Arg Val Glu Trp Leu Arg Lys Leu Leu Gln Asp Val His
            20                 25                 30

Asn Phe

<210> SEQ ID NO 15
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 15

Ser Val Ser Glu Ile Gln Leu Met His Asn Leu Gly Lys Phe Leu Asn
1               5                  10                 15

Asn Met Glu Arg Val Glu Trp Leu Arg Lys Leu Leu Gln Asp Val His
            20                 25                 30

Asn Phe
```

```
<210> SEQ ID NO 16
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 16

Ser Val Ser Glu Ile Gln Leu Met His Asn Leu Val Lys Phe Leu Asn
1               5                   10                  15

Asn Met Glu Arg Val Glu Trp Leu Arg Lys Leu Leu Gln Asp Val His
            20                  25                  30

Asn Phe

<210> SEQ ID NO 17
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 17

Ser Val Ser Glu Ile Gln Leu Met His Asn Leu Val Lys Phe Leu Thr
1               5                   10                  15

Asn Met Glu Arg Val Glu Trp Leu Arg Lys Leu Leu Gln Asp Val His
            20                  25                  30

Asn Phe

<210> SEQ ID NO 18
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 18

Ser Val Ser Glu Ile Gln Leu Met His Asn Leu Ala Lys Phe Leu Asn
1               5                   10                  15

Asn Met Glu Arg Val Glu Trp Leu Arg Lys Leu Leu Gln Asp Val His
            20                  25                  30

Asn Phe

<210> SEQ ID NO 19
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 19

Ser Val Ser Glu Ile Gln Leu Met His Asn Leu Ala Lys Leu Leu Asn
1               5                   10                  15

Asn Met Glu Arg Val Glu Trp Leu Arg Lys Leu Leu Gln Asp Val His
            20                  25                  30

Asn Phe

<210> SEQ ID NO 20
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 20
```

```
Ser Val Ser Glu Ile Gln Leu Met His Asn Leu Gly Lys Leu Leu Asn
1               5                   10                  15

Asn Met Glu Arg Val Glu Trp Leu Arg Lys Leu Leu Gln Asp Val His
            20                  25                  30

Asn Phe
```

<210> SEQ ID NO 21
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 21

```
Ser Val Ser Glu Ile Gln Leu Met His Asn Leu Gly Lys His Leu Asn
1               5                   10                  15

Asp Met Glu Arg Val Cys Trp Leu Cys Lys Leu Leu Gln Asp Val His
            20                  25                  30

Asn Phe
```

<210> SEQ ID NO 22
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 22

```
Ser Val Ser Glu Ile Gln Leu Met His Asn Leu Gly Lys His Leu Asn
1               5                   10                  15

Asn Met Glu Arg Val Cys Trp Leu Cys Lys Leu Leu Gln Asp Val His
            20                  25                  30

Asn Phe
```

<210> SEQ ID NO 23
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 23

```
Ser Val Ser Glu Ile Gln Leu Met His Asn Leu Gly Lys Phe Leu Asn
1               5                   10                  15

Asn Met Glu Arg Val Cys Trp Leu Cys Lys Leu Leu Gln Asp Val His
            20                  25                  30

Asn Phe
```

<210> SEQ ID NO 24
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 24

```
Ser Val Ser Glu Ile Gln Leu Met His Asn Leu Val Lys Phe Leu Asn
1               5                   10                  15

Asn Met Glu Arg Val Cys Trp Leu Cys Lys Leu Leu Gln Asp Val His
            20                  25                  30

Asn Phe
```

<210> SEQ ID NO 25
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 25

Ser Val Ser Glu Ile Gln Leu Met His Asn Leu Val Lys Phe Leu Thr
1               5                   10                  15

Asn Met Glu Arg Val Cys Trp Leu Cys Lys Leu Leu Gln Asp Val His
            20                  25                  30

Asn Phe

<210> SEQ ID NO 26
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 26

Ser Val Ser Glu Ile Gln Leu Met His Asn Leu Ala Lys Phe Leu Asn
1               5                   10                  15

Asn Met Glu Arg Val Cys Trp Leu Cys Lys Leu Leu Gln Asp Val His
            20                  25                  30

Asn Phe

<210> SEQ ID NO 27
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 27

Ser Val Ser Glu Ile Gln Leu Met His Asn Leu Ala Lys Leu Leu Asn
1               5                   10                  15

Asn Met Glu Arg Val Cys Trp Leu Cys Lys Leu Leu Gln Asp Val His
            20                  25                  30

Asn Phe

<210> SEQ ID NO 28
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 28

Ser Val Ser Glu Ile Gln Leu Met His Asn Leu Gly Lys Leu Leu Asn
1               5                   10                  15

Asn Met Glu Arg Val Cys Trp Leu Cys Lys Leu Leu Gln Asp Val His
            20                  25                  30

Asn Phe

<210> SEQ ID NO 29
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 29

Ser Val Ser Glu Ile Gln Leu Met His Asn Leu Gly Lys His Leu Asn
1               5                   10                  15

Asp Met Glu Arg Val Cys Trp Leu Cys Lys Lys Leu Gln Asp Val His
            20                  25                  30

Asn Phe

<210> SEQ ID NO 30
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 30

Ser Val Ser Glu Ile Gln Leu Met His Asn Leu Gly Lys His Leu Asn
1               5                   10                  15

Asn Met Glu Arg Val Cys Trp Leu Cys Lys Lys Leu Gln Asp Val His
            20                  25                  30

Asn Phe

<210> SEQ ID NO 31
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 31

Ser Val Ser Glu Ile Gln Leu Met His Asn Leu Gly Lys Phe Leu Asn
1               5                   10                  15

Asn Met Glu Arg Val Cys Trp Leu Cys Lys Lys Leu Gln Asp Val His
            20                  25                  30

Asn Phe

<210> SEQ ID NO 32
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 32

Ser Val Ser Glu Ile Gln Leu Met His Asn Leu Val Lys Phe Leu Asn
1               5                   10                  15

Asn Met Glu Arg Val Cys Trp Leu Cys Lys Lys Leu Gln Asp Val His
            20                  25                  30

Asn Phe

<210> SEQ ID NO 33
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 33

Ser Val Ser Glu Ile Gln Leu Met His Asn Leu Val Lys Phe Leu Thr
1               5                   10                  15

Asn Met Glu Arg Val Cys Trp Leu Cys Lys Lys Leu Gln Asp Val His
            20                  25                  30

Asn Phe

<210> SEQ ID NO 34
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 34

Ser Val Ser Glu Ile Gln Leu Met His Asn Leu Ala Lys Phe Leu Asn
1               5                   10                  15

Asn Met Glu Arg Val Cys Trp Leu Cys Lys Lys Leu Gln Asp Val His
            20                  25                  30

Asn Phe

<210> SEQ ID NO 35
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 35

Ser Val Ser Glu Ile Gln Leu Met His Asn Leu Ala Lys Leu Leu Asn
1               5                   10                  15

Asn Met Glu Arg Val Cys Trp Leu Cys Lys Lys Leu Gln Asp Val His
            20                  25                  30

Asn Phe

<210> SEQ ID NO 36
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 36

Ser Val Ser Glu Ile Gln Leu Met His Asn Leu Gly Lys Leu Leu Asn
1               5                   10                  15

Asn Met Glu Arg Val Cys Trp Leu Cys Lys Lys Leu Gln Asp Val His
            20                  25                  30

Asn Phe

<210> SEQ ID NO 37
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (19)..(19)
<223> OTHER INFORMATION: This is the dextrorotary form of cysteine

<400> SEQUENCE: 37

Ser Val Ser Glu Ile Gln Leu Met His Asn Leu Gly Lys His Leu Asn
1               5                   10                  15

Asp Met Cys Arg Val Cys Trp Leu Arg Lys Leu Leu Gln Asp Val His
            20                  25                  30

Asn Phe

```
<210> SEQ ID NO 38
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (19)..(19)
<223> OTHER INFORMATION: This is the dextrorotary form of cysteine

<400> SEQUENCE: 38

Ser Val Ser Glu Ile Gln Leu Met His Asn Leu Gly Lys His Leu Asn
1               5                   10                  15

Asn Met Cys Arg Val Cys Trp Leu Arg Lys Leu Leu Gln Asp Val His
            20                  25                  30

Asn Phe

<210> SEQ ID NO 39
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (19)..(19)
<223> OTHER INFORMATION: This is the dextrorotary form of cysteine

<400> SEQUENCE: 39

Ser Val Ser Glu Ile Gln Leu Met His Asn Leu Gly Lys Phe Leu Asn
1               5                   10                  15

Asn Met Cys Arg Val Cys Trp Leu Arg Lys Leu Leu Gln Asp Val His
            20                  25                  30

Asn Phe

<210> SEQ ID NO 40
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (19)..(19)
<223> OTHER INFORMATION: This is the dextrorotary form of cysteine

<400> SEQUENCE: 40

Ser Val Ser Glu Ile Gln Leu Met His Asn Leu Val Lys Phe Leu Asn
1               5                   10                  15

Asn Met Cys Arg Val Cys Trp Leu Arg Lys Leu Leu Gln Asp Val His
            20                  25                  30

Asn Phe

<210> SEQ ID NO 41
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (19)..(19)
<223> OTHER INFORMATION: This is the dextrorotary form of cysteine

<400> SEQUENCE: 41

Ser Val Ser Glu Ile Gln Leu Met His Asn Leu Val Lys Phe Leu Thr
```

```
1               5                  10                 15
Asn Met Cys Arg Val Cys Trp Leu Arg Lys Leu Leu Gln Asp Val His
            20                  25                 30

Asn Phe

<210> SEQ ID NO 42
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (19)..(19)
<223> OTHER INFORMATION: This is the dextrorotary form of cysteine

<400> SEQUENCE: 42

Ser Val Ser Glu Ile Gln Leu Met His Asn Leu Ala Lys Phe Leu Asn
1               5                  10                 15

Asn Met Cys Arg Val Cys Trp Leu Arg Lys Leu Leu Gln Asp Val His
            20                  25                 30

Asn Phe

<210> SEQ ID NO 43
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (19)..(19)
<223> OTHER INFORMATION: This is the dextrorotary form of cysteine

<400> SEQUENCE: 43

Ser Val Ser Glu Ile Gln Leu Met His Asn Leu Ala Lys Leu Leu Asn
1               5                  10                 15

Asn Met Cys Arg Val Cys Trp Leu Arg Lys Leu Leu Gln Asp Val His
            20                  25                 30

Asn Phe

<210> SEQ ID NO 44
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (19)..(19)
<223> OTHER INFORMATION: This is the dextrorotary form of cysteine

<400> SEQUENCE: 44

Ser Val Ser Glu Ile Gln Leu Met His Asn Leu Gly Lys Leu Leu Asn
1               5                  10                 15

Asn Met Cys Arg Val Cys Trp Leu Arg Lys Leu Leu Gln Asp Val His
            20                  25                 30

Asn Phe

<210> SEQ ID NO 45
<211> LENGTH: 34
<212> TYPE: PRT
<213> ORGANISM: Artificial Sequence
<220> FEATURE:
<223> OTHER INFORMATION: Human Mutated Peptide
```

```
<220> FEATURE:
<221> NAME/KEY: MISC_FEATURE
<222> LOCATION: (19)..(19)
<223> OTHER INFORMATION: This is the dextrorotary form of cysteine

<400> SEQUENCE: 45

Ser Val Ser Glu Ile Gln Leu Met His Asn Leu Gly Lys His Leu Asn
1               5                   10                  15

Asp Met Cys Arg Val Cys Trp Leu Arg Lys Lys Leu Gln Asp Val His
            20                  25                  30

Asn Phe

<210> SEQ ID NO 46
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (19)..(19)
<223> OTHER INFORMATION: This is the dextrorotary form of cysteine

<400> SEQUENCE: 46

Ser Val Ser Glu Ile Gln Leu Met His Asn Leu Gly Lys His Leu Asn
1               5                   10                  15

Asn Met Cys Arg Val Cys Trp Leu Arg Lys Lys Leu Gln Asp Val His
            20                  25                  30

Asn Phe

<210> SEQ ID NO 47
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (19)..(19)
<223> OTHER INFORMATION: This is the dextrorotary form of cysteine

<400> SEQUENCE: 47

Ser Val Ser Glu Ile Gln Leu Met His Asn Leu Gly Lys Phe Leu Asn
1               5                   10                  15

Asn Met Cys Arg Val Cys Trp Leu Arg Lys Lys Leu Gln Asp Val His
            20                  25                  30

Asn Phe

<210> SEQ ID NO 48
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (19)..(19)
<223> OTHER INFORMATION: This is the dextrorotary form of cysteine

<400> SEQUENCE: 48

Ser Val Ser Glu Ile Gln Leu Met His Asn Leu Val Lys Phe Leu Asn
1               5                   10                  15

Asn Met Cys Arg Val Cys Trp Leu Arg Lys Lys Leu Gln Asp Val His
            20                  25                  30

Asn Phe
```

<210> SEQ ID NO 49
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (19)..(19)
<223> OTHER INFORMATION: This is the dextrorotary form of cysteine

<400> SEQUENCE: 49

Ser Val Ser Glu Ile Gln Leu Met His Asn Leu Val Lys Phe Leu Thr
1               5                   10                  15

Asn Met Cys Arg Val Cys Trp Leu Arg Lys Lys Leu Gln Asp Val His
            20                  25                  30

Asn Phe

<210> SEQ ID NO 50
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (19)..(19)
<223> OTHER INFORMATION: This is the dextrorotary form of cysteine

<400> SEQUENCE: 50

Ser Val Ser Glu Ile Gln Leu Met His Asn Leu Ala Lys Phe Leu Asn
1               5                   10                  15

Asn Met Cys Arg Val Cys Trp Leu Arg Lys Lys Leu Gln Asp Val His
            20                  25                  30

Asn Phe

<210> SEQ ID NO 51
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (19)..(19)
<223> OTHER INFORMATION: This is the dextrorotary form of cysteine

<400> SEQUENCE: 51

Ser Val Ser Glu Ile Gln Leu Met His Asn Leu Ala Lys Leu Leu Asn
1               5                   10                  15

Asn Met Cys Arg Val Cys Trp Leu Arg Lys Lys Leu Gln Asp Val His
            20                  25                  30

Asn Phe

<210> SEQ ID NO 52
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (19)..(19)
<223> OTHER INFORMATION: This is the dextrorotary form of cysteine

<400> SEQUENCE: 52

```
Ser Val Ser Glu Ile Gln Leu Met His Asn Leu Gly Lys Leu Leu Asn
1               5                   10                  15

Asn Met Cys Arg Val Cys Trp Leu Arg Lys Lys Leu Gln Asp Val His
            20                  25                  30

Asn Phe
```

<210> SEQ ID NO 53
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (12)..(12)
<223> OTHER INFORMATION: Can be either glycine, valine, or alanine
<220> FEATURE:
<221> NAME/KEY: MISC_FEATURE
<222> LOCATION: (14)..(14)
<223> OTHER INFORMATION: Can be either histidine, phenylalanine, or
      leucine
<220> FEATURE:
<221> NAME/KEY: MISC_FEATURE
<222> LOCATION: (16)..(16)
<223> OTHER INFORMATION: Can be either asparagine or threonine
<220> FEATURE:
<221> NAME/KEY: MISC_FEATURE
<222> LOCATION: (17)..(17)
<223> OTHER INFORMATION: Can be either aspartate or asparagine

<400> SEQUENCE: 53

```
Ser Val Ser Glu Ile Gln Leu Met His Asn Leu Xaa Lys Xaa Leu Xaa
1               5                   10                  15

Xaa Met Glu Arg Val Glu Trp Leu Arg Lys Lys Leu Gln Asp Val His
            20                  25                  30

Asn Phe
```

<210> SEQ ID NO 54
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (19)..(19)
<223> OTHER INFORMATION: Can be either glutamate or the dextrorotary
      form of cysteine.
<220> FEATURE:
<221> NAME/KEY: MISC_FEATURE
<222> LOCATION: (22)..(22)
<223> OTHER INFORMATION: Can be either glutamate or cysteine
<220> FEATURE:
<221> NAME/KEY: MISC_FEATURE
<222> LOCATION: (25)..(25)
<223> OTHER INFORMATION: Can be either arginine or cysteine

<400> SEQUENCE: 54

```
Ser Val Ser Glu Ile Gln Leu Met His Asn Leu Gly Lys His Leu Asn
1               5                   10                  15

Ser Met Xaa Arg Val Xaa Trp Leu Xaa Lys Leu Leu Gln Asp Val His
            20                  25                  30

Asn Phe
```

<210> SEQ ID NO 55
<211> LENGTH: 34
<212> TYPE: PRT
<213> ORGANISM: Artificial Sequence

```
<220> FEATURE:
<223> OTHER INFORMATION: Human Mutated Peptide
<220> FEATURE:
<221> NAME/KEY: MISC_FEATURE
<222> LOCATION: (12)..(12)
<223> OTHER INFORMATION: Can be either glycine, valine, or alanine
<220> FEATURE:
<221> NAME/KEY: MISC_FEATURE
<222> LOCATION: (14)..(14)
<223> OTHER INFORMATION: Can be either histidine, phenylalanine, or
      leucine
<220> FEATURE:
<221> NAME/KEY: MISC_FEATURE
<222> LOCATION: (16)..(16)
<223> OTHER INFORMATION: Can be either asparagine or threonine
<220> FEATURE:
<221> NAME/KEY: MISC_FEATURE
<222> LOCATION: (17)..(17)
<223> OTHER INFORMATION: Can be either serine, aspartate, or asparagine
<220> FEATURE:
<221> NAME/KEY: MISC_FEATURE
<222> LOCATION: (19)..(19)
<223> OTHER INFORMATION: Can be either glutamate or the dextrorotary
      form of cysteine
<220> FEATURE:
<221> NAME/KEY: MISC_FEATURE
<222> LOCATION: (22)..(22)
<223> OTHER INFORMATION: Can be either glutamate or cysteine
<220> FEATURE:
<221> NAME/KEY: MISC_FEATURE
<222> LOCATION: (25)..(25)
<223> OTHER INFORMATION: Can be either arginine or cysteine

<400> SEQUENCE: 55

Ser Val Ser Glu Ile Gln Leu Met His Asn Leu Xaa Lys Xaa Leu Xaa
1               5                   10                  15

Xaa Met Xaa Arg Val Xaa Trp Leu Xaa Lys Leu Leu Gln Asp Val His
            20                  25                  30

Asn Phe

<210> SEQ ID NO 56
<211> LENGTH: 34
<212> TYPE: PRT
<213> ORGANISM: Artificial Sequence
<220> FEATURE:
<223> OTHER INFORMATION: Human Mutated Peptide
<220> FEATURE:
<221> NAME/KEY: MISC_FEATURE
<222> LOCATION: (12)..(12)
<223> OTHER INFORMATION: Can be either glycine, valine, or alanine
<220> FEATURE:
<221> NAME/KEY: MISC_FEATURE
<222> LOCATION: (14)..(14)
<223> OTHER INFORMATION: Can be either histidine, phenylalanine, or
      leucine
<220> FEATURE:
<221> NAME/KEY: MISC_FEATURE
<222> LOCATION: (16)..(16)
<223> OTHER INFORMATION: Can be either asparagine or threonine
<220> FEATURE:
<221> NAME/KEY: MISC_FEATURE
<222> LOCATION: (17)..(17)
<223> OTHER INFORMATION: Can be either aspartate or asparagine
<220> FEATURE:
<221> NAME/KEY: MISC_FEATURE
<222> LOCATION: (19)..(19)
<223> OTHER INFORMATION: Can be either glutamate or the dextrorotary
      form of cysteine
<220> FEATURE:
<221> NAME/KEY: MISC_FEATURE
<222> LOCATION: (22)..(22)
<223> OTHER INFORMATION: Can be either glutamate or cysteine
<220> FEATURE:
<221> NAME/KEY: MISC_FEATURE
<222> LOCATION: (25)..(25)
<223> OTHER INFORMATION: Can be either arginine or cysteine
```

<400> SEQUENCE: 56

Ser Val Ser Glu Ile Gln Leu Met His Asn Leu Xaa Lys Xaa Leu Xaa
1               5                   10                  15

Xaa Met Xaa Arg Val Xaa Trp Leu Xaa Lys Lys Leu Gln Asp Val His
            20                  25                  30

Asn Phe

<210> SEQ ID NO 57
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 57

Ser Val Ser Glu Ile Gln Leu Met His Asn Leu Gly Lys His Leu Asn
1               5                   10                  15

Ser Met Glu Arg Val Glu Phe Leu Arg Lys Lys Leu Gln Asp Val His
            20                  25                  30

Asn Phe

<210> SEQ ID NO 58
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 58

Ser Val Ser Glu Ile Gln Leu Met His Asn Leu Gly Lys His Leu Asn
1               5                   10                  15

Ser Met Glu Arg Val Glu Trp Leu Arg Lys Lys Ile Gln Asp Val His
            20                  25                  30

Asn Phe

<210> SEQ ID NO 59
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 59

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Ile His
            20                  25                  30

Asn Phe

<210> SEQ ID NO 60
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 60

Ser Val Ser Glu Ile Gln Leu Met His Asn Leu Gly Lys His Leu Asn
1               5                   10                  15

Ser Met Glu Arg Val Glu Phe Leu Arg Lys Leu Ile Gln Asp Ile His
            20                  25                  30

Asn Phe

<210> SEQ ID NO 61
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 61

Ser Val Ser Glu Ile Gln Leu Met His Asn Leu Gly Lys His Leu Asn
1               5                   10                  15

Ser Met Glu Arg Val Glu Phe Leu Arg Lys Leu Leu Gln Asp Val His
            20                  25                  30

Asn Phe

<210> SEQ ID NO 62
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 62

Ser Val Ser Glu Ile Gln Leu Met His Asn Leu Gly Lys His Leu Asn
1               5                   10                  15

Ser Met Glu Arg Val Glu Phe Leu Arg Lys Lys Ile Gln Asp Val His
            20                  25                  30

Asn Phe

<210> SEQ ID NO 63
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 63

Ser Val Ser Glu Ile Gln Leu Met His Asn Leu Gly Lys His Leu Asn
1               5                   10                  15

Ser Met Glu Arg Val Glu Trp Leu Arg Lys Leu Ile Gln Asp Val His
            20                  25                  30

Asn Phe

<210> SEQ ID NO 64
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 64

Ser Val Ser Glu Ile Gln Leu Met His Asn Leu Gly Lys His Leu Asn
1               5                   10                  15

Ser Met Glu Arg Val Glu Phe Leu Arg Lys Lys Leu Gln Asp Ile His
            20                  25                  30

Asn Phe

<210> SEQ ID NO 65
<211> LENGTH: 34
<212> TYPE: PRT
<213> ORGANISM: Artificial Sequence -continued

```
<220> FEATURE:
<223> OTHER INFORMATION: Human Mutated Peptide

<400> SEQUENCE: 65

Ser Val Ser Glu Ile Gln Leu Met His Asn Leu Gly Lys His Leu Asn
1               5                   10                  15

Ser Met Glu Arg Val Glu Trp Leu Arg Lys Ile Gln Asp Ile His
            20                  25                  30

Asn Phe

<210> SEQ ID NO 66
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 66

Ser Val Ser Glu Ile Gln Leu Met His Asn Leu Gly Lys His Leu Asn
1               5                   10                  15

Ser Met Glu Arg Val Glu Trp Leu Arg Lys Leu Leu Gln Asp Ile His
            20                  25                  30

Asn Phe

<210> SEQ ID NO 67
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 67

Ser Val Ser Glu Ile Gln Leu Met His Asn Leu Gly Lys His Leu Asn
1               5                   10                  15

Ser Met Ala Arg Val Glu Trp Leu Arg Lys Lys Leu Gln Asp Val His
            20                  25                  30

Asn Phe

<210> SEQ ID NO 68
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 68

Ser Val Ser Glu Ile Gln Leu Met His Asn Leu Gly Lys His Leu Asn
1               5                   10                  15

Ser Met Glu Ala Val Glu Trp Leu Arg Lys Lys Leu Gln Asp Val His
            20                  25                  30

Asn Phe

<210> SEQ ID NO 69
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 69

Ser Val Ser Glu Ile Gln Leu Met His Asn Leu Gly Lys His Leu Asn
1               5                   10                  15
```

```
Ser Met Glu Arg Ala Glu Trp Leu Arg Lys Lys Leu Gln Asp Val His
            20                  25                  30

Asn Phe

<210> SEQ ID NO 70
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 70

Ser Val Ser Glu Ile Gln Leu Met His Asn Leu Gly Lys His Leu Asn
1               5                   10                  15

Ser Met Glu Arg Val Glu Ala Leu Arg Lys Lys Leu Gln Asp Val His
            20                  25                  30

Asn Phe

<210> SEQ ID NO 71
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 71

Ser Val Ser Glu Ile Gln Leu Met His Asn Leu Gly Lys His Leu Asn
1               5                   10                  15

Ser Met Glu Arg Val Glu Trp Ala Arg Lys Lys Leu Gln Asp Val His
            20                  25                  30

Asn Phe

<210> SEQ ID NO 72
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 72

Ser Val Ser Glu Ile Gln Leu Met His Asn Leu Gly Lys His Leu Asn
1               5                   10                  15

Ser Met Glu Arg Val Glu Trp Leu Arg Ala Lys Leu Gln Asp Val His
            20                  25                  30

Asn Phe

<210> SEQ ID NO 73
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 73

Ser Val Ser Glu Ile Gln Leu Met His Asn Leu Gly Lys His Leu Asn
1               5                   10                  15

Ser Met Glu Arg Val Glu Trp Leu Arg Lys Ala Leu Gln Asp Val His
            20                  25                  30

Asn Phe

<210> SEQ ID NO 74
<211> LENGTH: 34
```

```
<212> TYPE: PRT
<213> ORGANISM: Artificial Sequence
<220> FEATURE:
<223> OTHER INFORMATION: Human Mutated Peptide

<400> SEQUENCE: 74

Ser Val Ser Glu Ile Gln Leu Met His Asn Leu Gly Lys His Leu Asn
1               5                   10                  15

Ser Met Glu Arg Val Glu Trp Leu Arg Lys Lys Ala Gln Asp Val His
                20                  25                  30

Asn Phe

<210> SEQ ID NO 75
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 75

Ser Val Ser Glu Ile Gln Leu Met His Asn Leu Gly Lys His Leu Asn
1               5                   10                  15

Ser Met Glu Arg Val Glu Trp Leu Arg Lys Lys Leu Ala Asp Val His
                20                  25                  30

Asn Phe

<210> SEQ ID NO 76
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 76

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Ala His
                20                  25                  30

Asn Phe

<210> SEQ ID NO 77
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 77

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val Ala
                20                  25                  30

Asn Phe

<210> SEQ ID NO 78
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 78

Ser Val Ser Glu Ile Gln Leu Met His Asn Leu Gly Lys His Leu Asn
```

```
                1               5                  10                  15
Ser Met Glu Arg Val Glu Trp Leu Arg Lys Lys Leu Gln Asp Val His
            20                  25                  30

Asn Ala

<210> SEQ ID NO 79
<211> LENGTH: 34
<212> TYPE: PRT
<213> ORGANISM: Homo Sapiens
<220> FEATURE:
<221> NAME/KEY: MISC_FEATURE
<223> OTHER INFORMATION: Protein fragment including amino acids 1-34 of
      parathyroid hormone-related protein

<400> SEQUENCE: 79

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala

<210> SEQ ID NO 80
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 80

Ala Val Ser Glu His Gln Leu Leu His Asp Lys Gly Lys Ser Ile Gln
1               5                   10                  15

Asp Leu Arg Arg Arg Phe Trp Leu His His Leu Ile Ala Glu Ile His
            20                  25                  30

Thr Ala

<210> SEQ ID NO 81
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 81

Ala Val Ser Glu His Gln Leu Leu His Asp Lys Gly Lys Ser Ile Gln
1               5                   10                  15

Asp Leu Arg Arg Arg Phe Phe Leu His His Lys Ile Ala Glu Ile His
            20                  25                  30

Thr Ala

<210> SEQ ID NO 82
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 82

Ala Val Ser Glu His Gln Leu Leu His Asp Lys Gly Lys Ser Ile Gln
1               5                   10                  15

Asp Leu Arg Arg Arg Phe Phe Leu His His Leu Leu Ala Glu Ile His
            20                  25                  30

Thr Ala
```

<210> SEQ ID NO 83
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 83

```
Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Val His
                20                  25                  30

Thr Ala
```

<210> SEQ ID NO 84
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 84

```
Ala Val Ser Glu His Gln Leu Leu His Asp Lys Gly Lys Ser Ile Gln
1               5                   10                  15

Asp Leu Arg Arg Arg Phe Trp Leu His His Lys Leu Ala Glu Val His
                20                  25                  30

Thr Ala
```

<210> SEQ ID NO 85
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 85

```
Ala Val Ser Glu His Gln Leu Leu His Asp Lys Gly Lys Ser Ile Gln
1               5                   10                  15

Asp Leu Arg Arg Arg Phe Trp Leu His His Lys Ile Ala Glu Ile His
                20                  25                  30

Thr Ala
```

<210> SEQ ID NO 86
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 86

```
Ala Val Ser Glu His Gln Leu Leu His Asp Lys Gly Lys Ser Ile Gln
1               5                   10                  15

Asp Leu Arg Arg Arg Phe Phe Leu His His Lys Leu Ala Glu Ile His
                20                  25                  30

Thr Ala
```

<210> SEQ ID NO 87
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 87

Ala Val Ser Glu His Gln Leu Leu His Asp Lys Gly Lys Ser Ile Gln
1               5                   10                  15

Asp Leu Arg Arg Arg Phe Phe Leu His His Lys Ile Ala Glu Val His
            20                  25                  30

Thr Ala

<210> SEQ ID NO 88
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 88

Ala Val Ser Glu His Gln Leu Leu His Asp Lys Gly Lys Ser Ile Gln
1               5                   10                  15

Asp Leu Arg Arg Arg Phe Trp Leu His His Leu Leu Ala Glu Ile His
            20                  25                  30

Thr Ala

<210> SEQ ID NO 89
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 89

Ala Val Ser Glu His Gln Leu Leu His Asp Lys Gly Lys Ser Ile Gln
1               5                   10                  15

Asp Leu Arg Arg Arg Phe Trp Leu His His Leu Ile Ala Glu Val His
            20                  25                  30

Thr Ala

<210> SEQ ID NO 90
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 90

Ala Val Ser Glu His Gln Leu Leu His Asp Lys Gly Lys Ser Ile Gln
1               5                   10                  15

Asp Leu Arg Arg Arg Phe Phe Leu His His Leu Leu Ala Glu Val His
            20                  25                  30

Thr Ala

<210> SEQ ID NO 91
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 91

Ala Val Ser Glu His Gln Leu Leu His Asp Lys Gly Lys Ser Ile Ala
1               5                   10                  15

Asp Leu Arg Arg Arg Phe Phe Leu His His Leu Ile Ala Glu Ile His
            20                  25                  30

Thr Ala

<210> SEQ ID NO 92
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 92

Ala Val Ser Glu His Gln Leu Leu His Asp Lys Gly Lys Ser Ile Gln
1               5                   10                  15

Asp Leu Ala Arg Arg Phe Phe Leu His His Leu Ile Ala Glu Ile His
            20                  25                  30

Thr Ala

<210> SEQ ID NO 93
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 93

Ala Val Ser Glu His Gln Leu Leu His Asp Lys Gly Lys Ser Ile Gln
1               5                   10                  15

Asp Leu Arg Ala Arg Phe Phe Leu His His Leu Ile Ala Glu Ile His
            20                  25                  30

Thr Ala

<210> SEQ ID NO 94
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 94

Ala Val Ser Glu His Gln Leu Leu His Asp Lys Gly Lys Ser Ile Gln
1               5                   10                  15

Asp Leu Arg Arg Ala Phe Phe Leu His His Leu Ile Ala Glu Ile His
            20                  25                  30

Thr Ala

<210> SEQ ID NO 95
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 95

Ala Val Ser Glu His Gln Leu Leu His Asp Lys Gly Lys Ser Ile Gln
1               5                   10                  15

Asp Leu Arg Arg Arg Phe Ala Leu His His Leu Ile Ala Glu Ile His
            20                  25                  30

Thr Ala

<210> SEQ ID NO 96
<211> LENGTH: 34
<212> TYPE: PRT
<213> ORGANISM: Artificial Sequence -continued

```
<220> FEATURE:
<223> OTHER INFORMATION: Human Mutated Peptide

<400> SEQUENCE: 96

Ala Val Ser Glu His Gln Leu Leu His Asp Lys Gly Lys Ser Ile Gln
1               5                   10                  15

Asp Leu Arg Arg Arg Phe Phe Ala His His Leu Ile Ala Glu Ile His
            20                  25                  30

Thr Ala

<210> SEQ ID NO 97
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 97

Ala Val Ser Glu His Gln Leu Leu His Asp Lys Gly Lys Ser Ile Gln
1               5                   10                  15

Asp Leu Arg Arg Arg Phe Phe Leu His His Ala Ile Ala Glu Ile His
            20                  25                  30

Thr Ala

<210> SEQ ID NO 98
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 98

Ala Val Ser Glu His Gln Leu Leu His Asp Lys Gly Lys Ser Ile Gln
1               5                   10                  15

Asp Leu Arg Arg Arg Phe Phe Leu His His Leu Ala Ala Glu Ile His
            20                  25                  30

Thr Ala

<210> SEQ ID NO 99
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 99

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ala His
            20                  25                  30

Thr Ala

<210> SEQ ID NO 100
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 100

Ala Val Ser Glu His Gln Leu Leu His Asp Lys Gly Lys Ser Ile Gln
1               5                   10                  15
```

-continued

```
Asp Leu Arg Arg Arg Phe Phe Leu His His Leu Ile Ala Glu Ile Ala
            20                  25                  30

Thr Ala

<210> SEQ ID NO 101
<211> LENGTH: 34
<212> TYPE: PRT
<213> ORGANISM: Artificial Sequence
<220> FEATURE:
<223> OTHER INFORMATION: Human Mutated Peptide

<400> SEQUENCE: 101

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Ala Ala
```